(12) United States Patent
Taylor et al.

(10) Patent No.: US 7,288,065 B1
(45) Date of Patent: Oct. 30, 2007

(54) ACCESS PLATFORM FOR INTERNAL MAMMARY DISSECTION

(75) Inventors: Charles S. Taylor, San Francisco, CA (US); William N. Aldrich, Redwood City, CA (US); Federico J. Benetti, Santa Fe (AR); Richard S. Ginn, San Jose, CA (US); Dwight P. Morejohn, Davis, CA (US); Brent Regan, Davis, CA (US); Eugene E. Reis, San Jose, CA (US); Ivan Sepetka, Los Altos, CA (US); William F. Witt, Palo Alto, CA (US)

(73) Assignee: CardioThoracic System, Inc., San Jose, CA (US)

( * ) Notice: Subject to any disclaimer, the term of this patent is extended or adjusted under 35 U.S.C. 154(b) by 0 days.

(21) Appl. No.: 09/480,828

(22) Filed: Jan. 10, 2000

Related U.S. Application Data

(63) Continuation of application No. 09/385,812, filed on Aug. 30, 1999, now abandoned, which is a continuation of application No. 08/903,516, filed on Jul. 30, 1997, now Pat. No. 5,944,736, which is a continuation of application No. 08/787,748, filed on Jan. 27, 1997, now abandoned, which is a continuation-in-part of application No. 08/619,903, filed on Mar. 20, 1996, now Pat. No. 5,976,171, which is a continuation-in-part of application No. 08/604,161, filed on Feb. 20, 1996, now Pat. No. 5,730,757.

(51) Int. Cl.
  *A61B 17/04* (2006.01)
  *A61B 1/32* (2006.01)
  *A61M 29/00* (2006.01)

(52) U.S. Cl. .................... 600/232; 600/231; 600/224; 600/233; 606/198

(58) Field of Classification Search ................ 606/198, 606/207, 201; 600/231–235, 201, 213, 210, 600/214, 224
See application file for complete search history.

(56) References Cited

U.S. PATENT DOCUMENTS 4,048,987 A  9/1977  Hurson .................. 128/20

(Continued)

FOREIGN PATENT DOCUMENTS

| GB | 168216 | 9/1921 |
| GB | 2 267 | 12/1993 |

OTHER PUBLICATIONS

Pilling Surgical Instruments, A Rusch International Company, Brochure.

(Continued)

*Primary Examiner*—(Jackie) Tan-Uyen Ho
*Assistant Examiner*—Melissa Ryckman
(74) *Attorney, Agent, or Firm*—Law Office of Alan W. Cannon

(57) ABSTRACT

An access platform having a first and a second blade interconnected to a spreader member that laterally drives the blades apart or together and a sternal pad interconnected to a blade. The superior blade is preferably pivotally coupled to the spreader member such that it naturally rises as the blades are separated. Alternatively, a vertical displacement member is operably interconnected to a blade and the spreader member and is used to vertically displace the interconnected superior blade and, thus, increase a surgeon's working space and visual access for the dissection of an internal mammary artery. A tissue retractor is interconnected to the blades to draw the soft tissue around an incision away from the surgeon's working area.

26 Claims, 62 Drawing Sheets

U.S. PATENT DOCUMENTS

| | | | | |
|---|---|---|---|---|
| 4,049,000 | A | 9/1977 | Williams | 128/276 |
| 4,434,791 | A | 3/1984 | Darnell | 128/20 |
| 4,627,421 | A | 12/1986 | Symbas et al. | 128/20 |
| 4,702,230 | A | 10/1987 | Pelta | 128/20 |
| 4,726,356 | A | 2/1988 | Santilli et al. | 128/20 |
| 4,747,395 | A | 5/1988 | Brief | 128/20 |
| 4,829,985 | A | 5/1989 | Couetil | 128/20 |
| 4,852,552 | A | 8/1989 | Chaux | 128/20 |
| 4,865,019 | A | 9/1989 | Phillips | 128/20 |
| 4,884,559 | A | 12/1989 | Collins | 128/17 |
| 4,971,037 | A | 11/1990 | Pelta | 128/20 |
| 4,991,566 | A | 2/1991 | Shulman et al. | |
| 4,993,862 | A | 2/1991 | Pelta | 403/59 |
| 5,025,779 | A | 6/1991 | Bugge | 128/20 |
| 5,052,373 | A | 10/1991 | Michelson | 128/20 |
| RE34,150 | E | 12/1992 | Santilli et al. | 128/20 |
| 5,167,223 | A | 12/1992 | Koros et al. | 128/20 |
| 5,363,841 | A * | 11/1994 | Coker | 600/211 |
| 5,554,101 | A | 9/1996 | Matula et al. | |
| 5,722,935 | A | 3/1998 | Christian | |
| 5,730,757 | A | 3/1998 | Benetti et al. | |
| 5,755,660 | A | 5/1998 | Tyagi | |
| 5,820,555 | A | 10/1998 | Watkins, III et al. | |
| 5,882,299 | A | 3/1999 | Rastegar et al. | 128/898 |
| 5,908,382 | A | 6/1999 | Koros et al. | 600/215 |
| 5,944,736 | A | 8/1999 | Taylor et al. | |
| 5,976,171 | A | 11/1999 | Taylor | |
| 5,984,867 | A | 11/1999 | Deckman et al. | 600/231 |
| 6,159,231 | A | 12/2000 | Looney et al. | |
| 6,478,734 | B1 | 11/2002 | Taylor et al. | |
| 6,602,189 | B1 | 8/2003 | Benetti et al. | |

OTHER PUBLICATIONS

Delacroix-Chevalier Surgical Instruments, IMA Savings Packages Brochure.

Ancalmo, N., and J.L. Ochsner: A Modified Sternal Retractor, Ann. Thorac. Surg. 21 (1976) 174.

Beg, R.A., H. Naraghipour, E.B. Kay, and P. Rullo: Internal Mammary Retractor, Ann. Thorac. Surg. 39 (1985) 286-287.

Chaux, A., and C. Blanche: A New Concept in Sternal Retraction: Applications for Internal Mammary Artery Dissection and Valve Replacement, Ann. Thorac. Surg. 42 (1986) 473-474.

McKeown, P.P., J. Crew, E.S. Hanna, and R. Jones: A Modified Sternal Retractor for Exposure of the Internal Mammary Artery, Ann. Thorac. Surg. 32 (1981) 619.

Vincent, J.G.: A Compact Single Post Internal Mammary Artery Dissection Retractor, Eur. J. Cardio-Thor. Surg. 3 (1989) 276-277.

Campalani, G., M.D., et al., A new self-retaining internal mammary artery retractor, J. Cardiovas. Surg. 28, 1987 Pittman, John, M.D., et al., Improved Visualization of the Internal Mammary Artery With a New Retractor System, Ann. Thorac. Surg. (1989;48:869-70).

Angelini, G. D., M.D., et al., A Fiber-Optic Retractor for Harvesting the Internal Mammary Artery, Ann. Thorac. Surg. (1990;50:314-5).

Phillips, Steven J., M.D., et al., A versatile retractor for use in harvesting the internal mammary artery and performing standard cardiac operations, J. Thorac. Cardiovasc. Surg. (1989;97:633-5).

Itoh, Toshiaki, M.D., et al., New Modification of a Mammary Artery Retractor, Ann. Thorac. Surg. (1994;57:1670-1).

Roux, D., M.D., et al., Internal mammary artery dissection: A three dimensional sternal retractor, J. Cardiovasc. Surg. (1989;30:996-7).

USSC Cardiovascular Thora-Lift™, United States Surgical Corporation, Norwalk, Connecticut, Product Brochure.

Pittman, J. et al., "Improved Visualization of the Internal Mammary Artery With a New Retractor System" Ann, Thorac. Surgery (1989; 48:869-70).

* cited by examiner

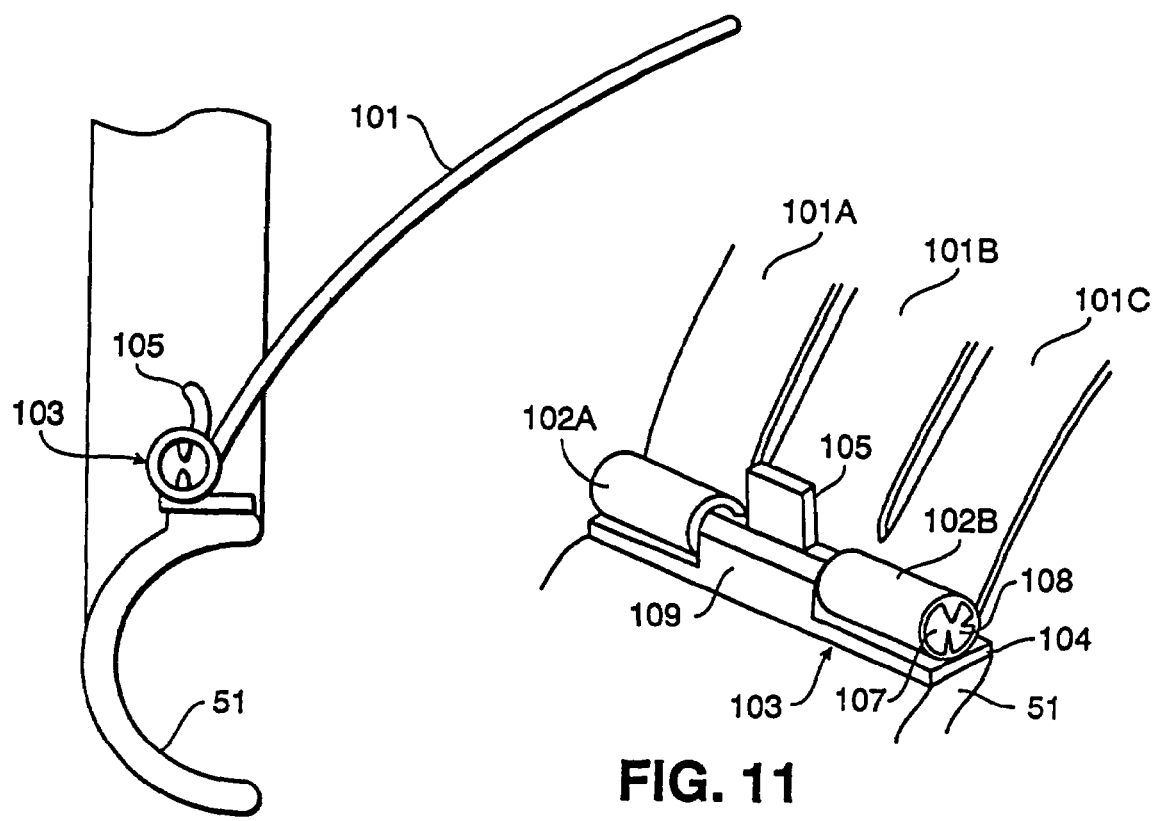
FIG. 10
FIG. 11
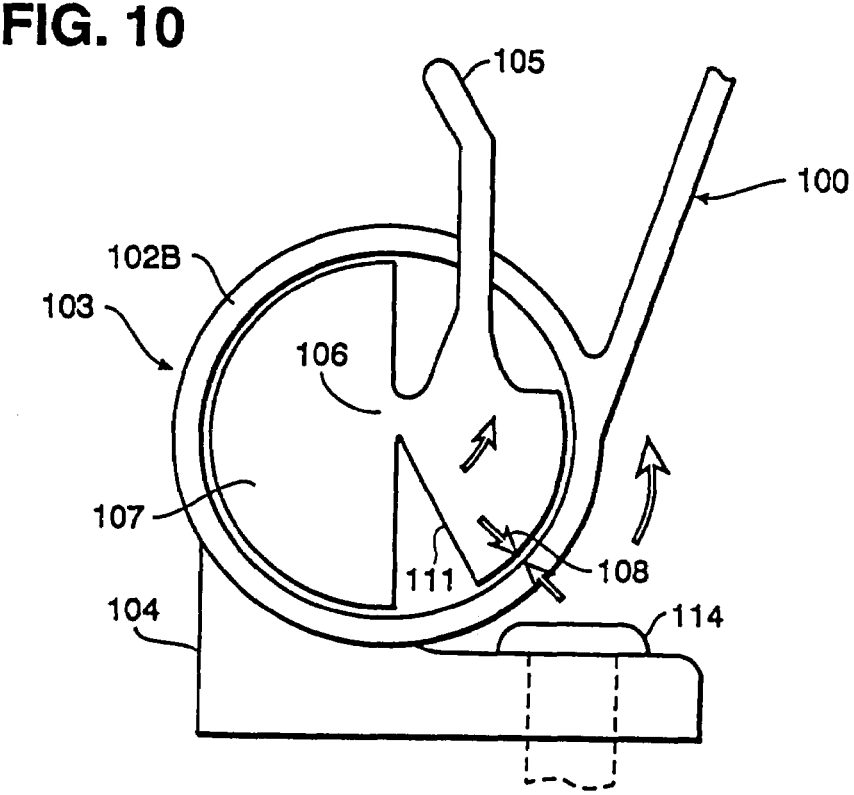
FIG. 12

ACCESS PLATFORM FOR INTERNAL MAMMARY DISSECTION

This application is a continuation of application Ser. No. 09/385,812, filed Aug. 30, 1999 now abandoned, which in turn is a continuation of Ser. No. 08/903,516, filed on Jul. 30, 1997, now issued as U.S. Pat. No. 5,944,736, which in turn is a continuation of Ser. No. 08/787,748, filed on Jan. 27, 1997, now abandoned, which in turn is a continuation-in-part of application Ser. No. 08/619,903, filed on Mar. 20, 1996, now issued as U.S. Pat. No. 5,976,171, which in turn is a continuation-in-part of application Ser. No. 08/604,161, filed on Feb. 20, 1996, now issued as U.S. Pat. No. 5,730,757, the disclosures of which are incorporated herein by reference as if set forth in full.

DESCRIPTION

1. Field of the Invention

This invention relates to retractors, and more particularly to an access platform that facilitates access to the interior of the chest cavity during surgical procedures.

2. Background of the Invention

Diseases of the cardiovascular system affect millions of people each year and are a leading cause of death in the United States and throughout the world. The cost to society from such diseases is enormous both in terms of lives lost and the cost of treating cardiac disease patients through surgery. A particularly prevalent form of cardiovascular disease is a reduction in the blood supply to the heart caused by atherosclerosis or other conditions that create a restriction in blood flow at a critical point in the cardiovascular system leading to the heart. In many cases, a blockage or restriction in the blood flow leading to the heart can be treated by a surgical procedure known as a Coronary Artery Bypass Graft (CABG) procedure, which is more commonly known as a "heart bypass" operation. In the CABG procedure, the surgeon either removes a portion of a vein from another part of the body to use as a graft and installs the graft at points that bypass the obstruction to restore normal blood flow to the heart or detaches one end of an artery and connects that end past the obstruction while leaving the other end attached to the arterial supply to restore normal blood flow to the heart.

Although the CABG procedure has become relatively common, i.e., heart bypass surgery is performed in one of every thousand persons in the United States, the procedure is lengthy and traumatic and can damage the heart, the central nervous system, and the blood supply. In a conventional CABG procedure, the surgeon cuts off the blood flow to the heart and then stops the heart from beating in order to install the graft. Thus, in order to perform the conventional CABG procedure, the surgeon must make a long incision down the middle of the chest, saw through the entire length of the sternum, spread the two halves of the sternum apart, and then perform several procedures necessary to attach the patient to a cardiopulmonary bypass machine to continue the circulation of oxygenated blood to the rest of the body while the graft is sewn in place.

The CABG procedure further requires that a connection for the flow of blood be established between two points that "by pass" a diseased area and restore an adequate blood flow. Typically, one end of a graft is sewn to the aorta, while the other end of the graft is sewn to a coronary artery, such as the left anterior descending (LAD) artery that provides blood flow to the main muscles of the heart. This procedure is known as a "free bypass graft." Alternatively, the internal mammary artery (IMA) pedicle is dissected off of the chest wall, while still attached to its arterial supply, and attached to the LAD past the obstruction. This procedure is known as an "in situ bypass graft."

In an in situ bypass graft, the IMA must be dissected from its connective tissue until there is sufficient slack in the IMA to insure that the graft does not kink after it is installed. The IMAs, left and right, extend from the subclavian arteries in the neck to the diaphragm and run along the backside of the rib cage adjacent the sternum. During a conventional in situ bypass graft, typically the left half of the sternum is raised to increase the surgeon's access to the left IMA (LIMA) and the heart. A device used for this type of sternal retraction is disclosed in United Kingdom Patent Application No. GB 2267827 A, "A device for Internal Mammary artery dissection."

Although several efforts have been made to make the CABG procedure less invasive and less traumatic, most techniques still require cardiac bypass and cardioplegia (stoppage of the heart). The safety and efficacy of CABG procedure could be improved if the surgeon could avoid the need to stop the heart from beating during the procedure, thereby eliminating the need to connect the patient to a cardiopulmonary bypass machine to sustain the patient's life during the CABG procedure and, thus, eliminate the need for the lengthy and traumatic surgical procedures necessary to connect the patient to a cardiopulmonary bypass machine. In recent years, a small number of surgeons have begun performing CABG procedures using surgical techniques especially developed to enable surgeons to perform the CABG procedure while the heart is still beating. In such procedures, there is no need for any form of cardiopulmonary bypass, no need to perform the extensive surgical procedures necessary to connect the patient to a cardiopulmonary bypass machine, cardioplegia is rendered unnecessary, the surgery is much less invasive and traumatic, and the entire procedure can typically be achieved through one or two comparatively small incisions (thoracotomies) in the chest.

Despite these advantages, the beating-heart CABG procedure is not widely practiced, in part, because of the difficulty in performing the necessary surgical procedures with conventional instruments while the heart is still beating. If specially designed instruments were available so that the CABG procedure could more easily be performed on the beating heart, the beating-heart CABG procedure would be more widely practiced and the treatment of cardiovascular disease would be improved in a significant part of the cardiovascular disease patient population.

Since the "beating-heart" CABG procedure is performed while the heart muscle is continuing to beat or contract, an anastomosis is difficult to perform because the blood continues to flow and the heart continues to move while the surgeon is attempting to sew the graft in place. The surgical procedure necessary to install the graft requires placing a series of sutures through several extremely small vessels that continue to move during the procedure. The sutures must become fully placed so that the graft is firmly in place and does not leak. It is also important that the procedure be performed rapidly because the blood flow through the artery may be interrupted or reduced during the procedure to allow the graft to be installed. This can cause ischemia, which should be minimized. Also, the surgeon's working space and visual access are limited because the surgeon may be working through a small incision in the chest or may be viewing the procedure on a video monitor, such that the site of the surgery is viewed via a surgical scope.

The "beating-heart" CABG procedure could be greatly improved if the surgeon's working space and visual access to the heart and the IMA were increased and improved. Current methods to increase and improve the surgeon's working space and visual access include laterally spreading or retracting the ribs with a conventional rib spreader/retractor, and then vertically displacing one of the retracted ribs relative to the other retracted rib to create a "tunnel" under the rib cage. To vertically displace one of the retracted ribs, some force external to the rib spreader must be applied to the rib. Typically, a surgeon's assistant will push or pull upwardly on the rib with a device having a rib blade inserted under the rib. However, the surgeon's assistant must then hold the rib in a vertically displaced position for the duration of the IMA dissection, resulting in an undesirable addition of another set of hands around the surgical area.

Another method used by surgeons to vertically displace the retracted rib is to insert a rib blade under the retracted rib and then attach the rib blade to a winch located above the patient. The winch is then operated to pull upwardly on the rib and hold it in a vertically displaced position. However, it is not at all uncommon for the patient to be raised off the operating table by the winch. This is undesirable because if the rib begins to crack or break, the weight of the patient's body will cause the rib to continue to break until the patient reaches the operating table.

While using these methods to vertically displace one of the retracted ribs, it may be desirable to further increase a surgeon's working space and visual access by depressing the sternum or the other retracted rib. However, depression of the sternum or the other retracted rib undesirably adds further sets of hands around the surgical site.

Furthermore, these methods and devices tend to limit where the thoracotomy can be performed. For example, if the thoracotomy is performed on the lateral side of the chest, the conventional rib spreader would tend to "stand-up" vertically from the ribs it is retracting such that it would intrude on the surgeon's working space. In addition, if a winch is used to offset the ribs, the lifting action of the winch will tend to rotate the patient to an undesirable and often unstable position for performing the IMA.

Equally important to improving the "beating heart" CABG procedure, is the ability to retract the soft tissue around the incision in the chest to draw the soft tissue away from the surgeon's working area. However, none of the methods or devices described above provide the ability to perform soft tissue retraction.

Thus, in view of the shortcomings of these devices and methods for increasing a surgeon's working space and visual access during a "beating-heart" CABG procedure, it would be desirable to have a device that is capable of laterally spreading the ribs and vertically displacing opposing retracted ribs relative to each other, that is capable of depressing the sternum, that is self-contained such that the force necessary to spread and vertically displace the ribs, and the force necessary to depress the sternum, is applied by the access platform itself rather than through additional external devices, that does not limit the location where a thoracotomy can be performed, and that is capable of soft tissue retraction.

SUMMARY OF THE INVENTION

The access platform of the present invention serves to facilitate the dissection of an internal mammary artery (IMA), including both proximal and distal dissection, and access to the heart during a "beating heart" Coronary Artery Bypass Graft (CABG) procedure by increasing the surgeon's working space and visual access. The access platform of the present invention is preferably capable of laterally spreading the ribs, vertically displacing the oppositely retracted ribs relative to each other and depressing the sternum to cause a "tunnel" effect under the retracted ribs. Moreover, it is preferably self-contained such that the force necessary to spread and vertically displace the ribs is applied by the access platform itself rather than through additional external devices. The access platform preferably comprises first and second blades interconnected to a spreader member that laterally drives the blades apart or together, a sternal pad interconnected to the blades, and a vertical displacement member interconnected to a blade and the spreader member. The vertical displacement member may preferably be bi-directional to cause the interconnected blade to be vertically displaced in either direction and, thus, increases the surgeon's working space and visual access to the IMA.

In addition, the access platform preferably includes an integrated tissue retractor, a hinged connector interconnected to the blades and the spreader member, and a port interconnected to the blades. The tissue retractor advantageously draws the soft tissue around an incision away from the surgeon's working area. The port advantageously provides a mount for a heart stabilizer, a scope for IMA take down, an IMA clamp, an IMA holder or other tools necessary for a "beating heart" CABG procedure. The hinged connector advantageously pivots the access platform away from the surgeon's working area.

In other embodiments, the superior blade is preferably pivotally mounted to the spreader member at a pivot point above the blade. The superior blade is naturally lifted as a spreading force from the inferior blade is transmitted to the superior blade through the pivot. The sternal pad may preferably be rotatably coupled to the superior blades.

In further embodiments, bladeless embodiments comprising tubular or hollow conically shaped bodies provide access to a patient's chest cavity.

It is an object of the present invention to provide an improved access platform.

Another object of the present invention is to provide an improved tissue retractor.

Further objects and advantages of the present invention will become apparent from a consideration of the drawings and the ensuing description.

BRIEF DESCRIPTION OF THE DRAWINGS

FIG. 10 is a side view of the tissue retractor assembly shown in FIG. 7 and including a positioning assembly.

FIG. 11 is an isometric view of the tissue retractor and positioning assembly in FIG. 8.

FIG. 12 is a partial side detail view of the positioning assembly in FIG. 8.

DESCRIPTION OF THE PREFERRED EMBODIMENT

Figure 1:
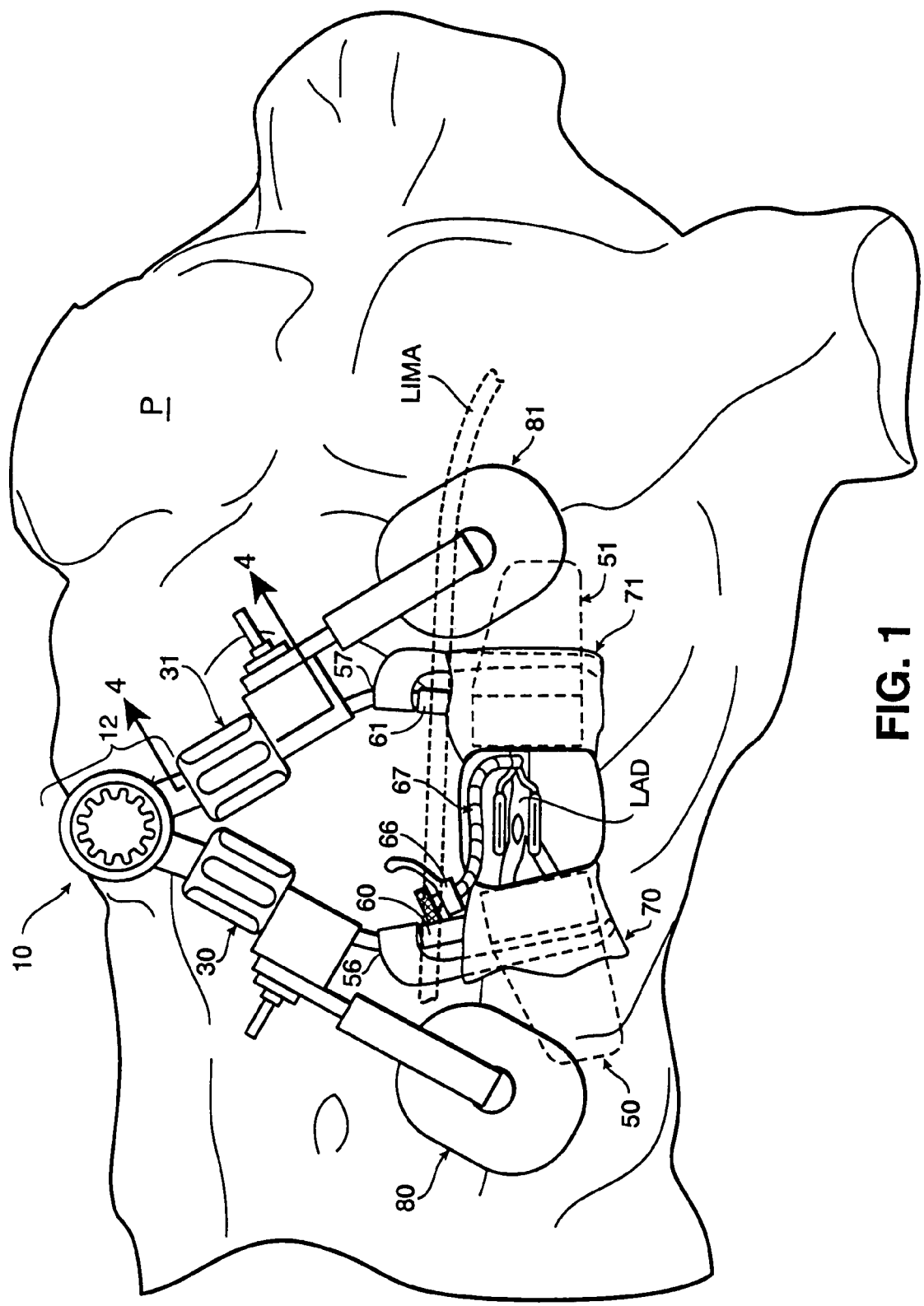
FIG. 1 is a top view of an embodiment of an access platform of the present invention disposed over the chest of a patient.

Referring now in detail to the drawings, therein illustrated are novel embodiments of an access platform that facilitates the dissection of an internal mammary artery (IMA), including both proximal and distal dissection, and access to the heart during a "beating heart" Coronary Artery Bypass Graph (CABG) procedure by increasing the surgeon's working space and visual access. The drawings illustrate various embodiments that at times incorporate some of the same or similar structures. Thus, where the same or similar structure appears in several drawings, and when practical, the structure is labeled using the same reference numeral on each drawing.

Turning to FIG. 1, the access platform 10 incorporating a preferred embodiment of the present invention, is shown disposed over the outline of a patient's chest P. An incision in the patient's chest P adjacent to the LIMA (shown in phantom) exposes an LAD artery on the exterior of the patient's heart. Preferably, the access platform 10 comprises a pair of blades 50 and 51, a pair of support pads 80 and 81, a pair of tissue retractors 70 and 71, a pair of torsional members 30 and 31, and a spreader member 12. The torsional members 30 and 31 and the spreader member 12 preferably extend away from the blades 50 and 51 and the tissue retractors 70 and 71 and, thus, the chest incision, in a plane relatively parallel to the patient's chest. As a result, the access platform 10 advantageously maintains a low profile that remains substantially clear of the surgeon's working space.

Figure 2:
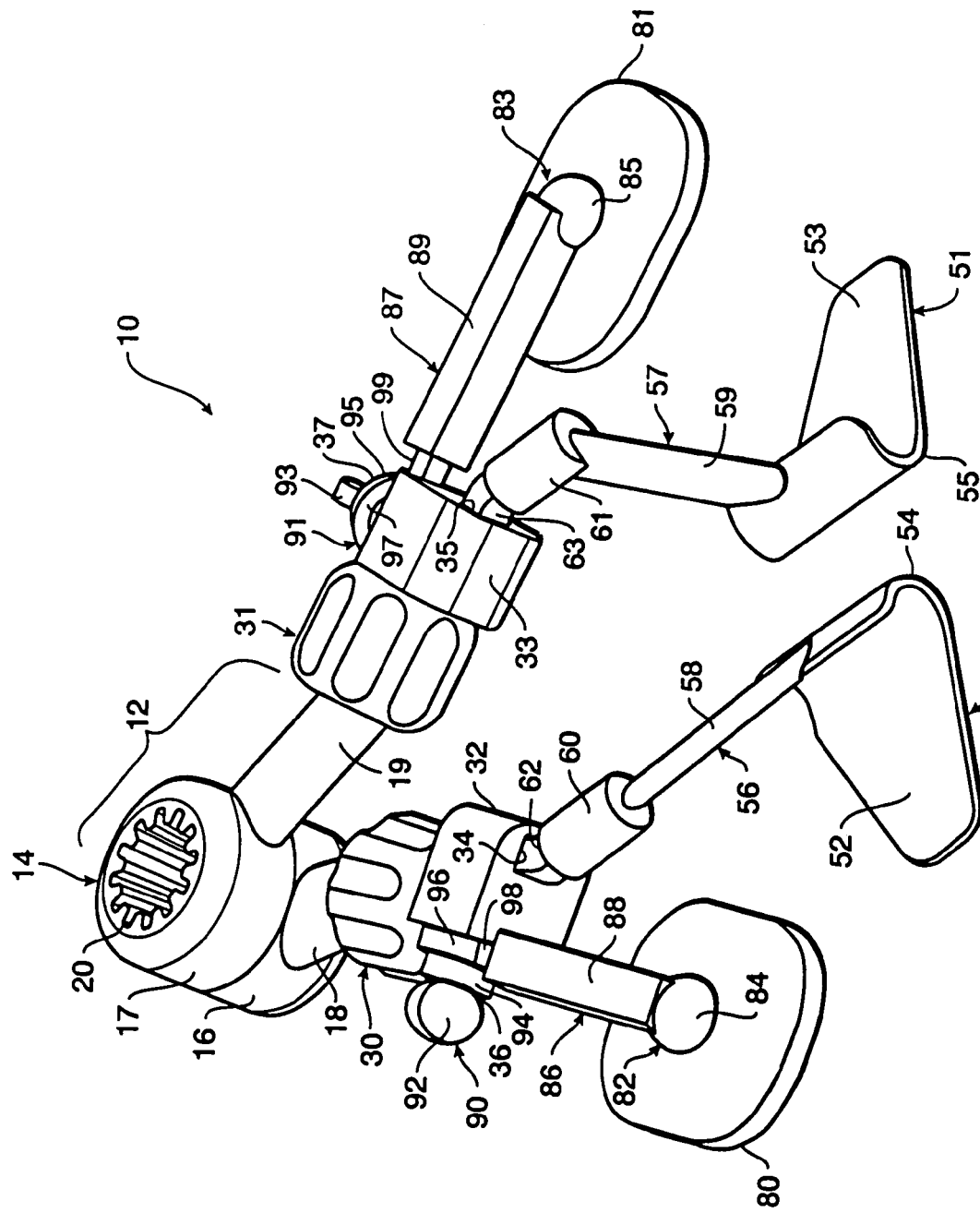
FIG. 2 is an isometric view of the access platform shown in FIG. 1 less the tissue retractor elements.

Referring to FIG. 2, the components of the access platform 10 are shown less the tissue retractors 70 and 71. The spreader member 12 preferably comprises a rotatable hub 14 including operably coupled upper and lower hub halves 17 and 16. A pair of spreader arms 19 and 18 extend from the upper and lower hub halves 17 and 16, respectively, and connect to the torsional members 31 and 30, respectively. Preferably, the hub 14 includes a harmonic gear drive 20 used to rotate the upper hub half 17 relative to the lower hub half 16 and, thus, spread or close the spreader arms 18 and 19 to retract or relax the patient's ribs.

Figure 3:
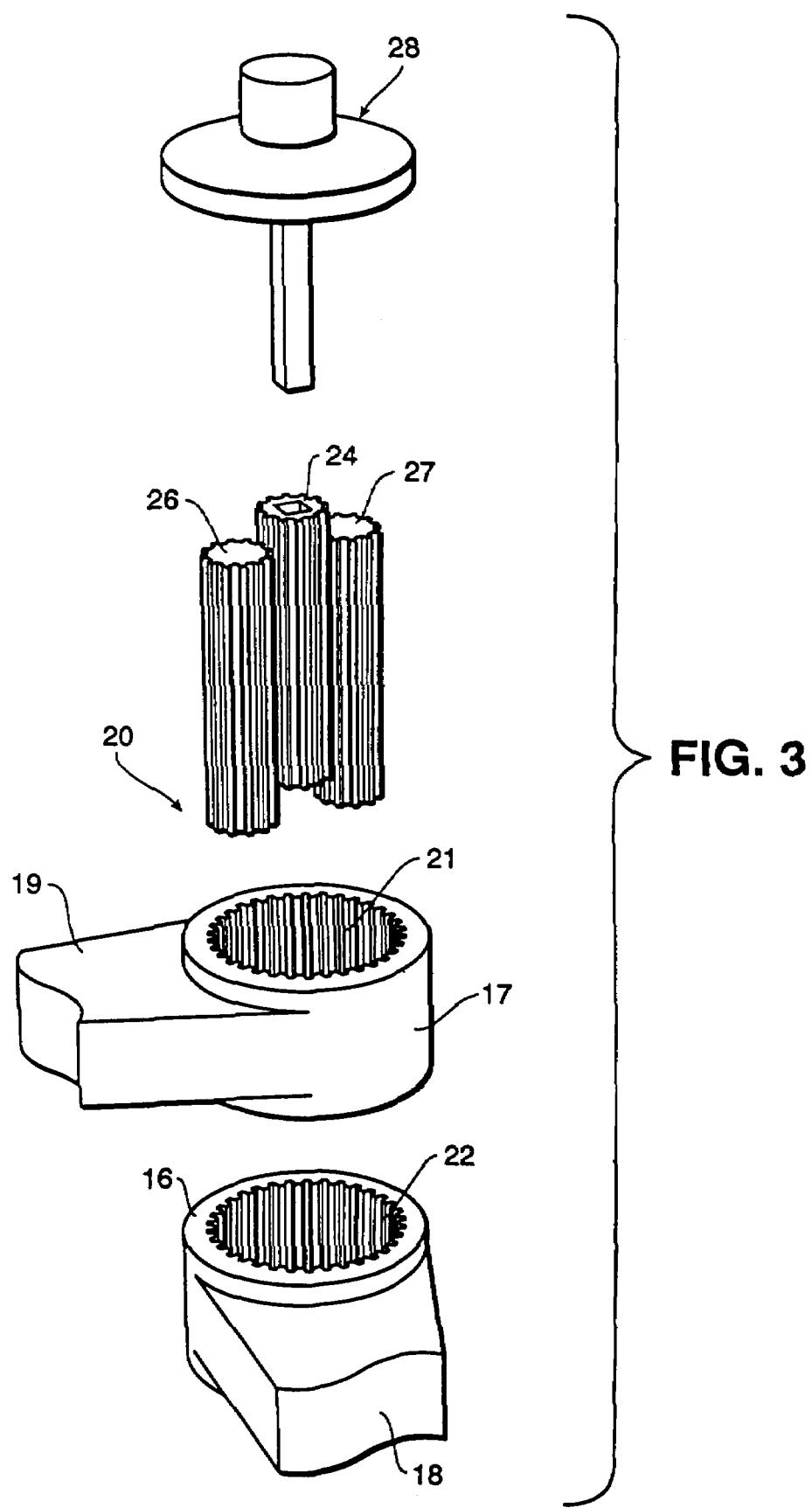
FIG. 3 is an exploded isometric view of a harmonic gear drive assembly of the access platform in FIG. 1.

Turning to FIG. 3, the harmonic gear drive 20 comprises ring gears 21 and 22, a pinion 24, idler gears 26 and 27, and a drive hub 28. The ring gears 21 and 22 are formed on the inner walls of the upper and lower hub halves 17 and 16, respectively. The idler gears 26 and 27 are operably connected to the pinion 24 and ring gears 21 and 22. Preferably, the effective gear ratios between the ring gears 21 and 22 are in the range of about 20-40:1, and the gear ratio between the pinion 24 and the ring gears 21 and 22 are in the range of about 3-5:1. Thus, only a relatively low torque is needed to turn the drive hub 28, which is connected to the pinion 24, to drive the ring gears 21 and 22 at a relatively high torque to rotate the upper hub 17 relative to the lower hub 16 to spread the spreader arms 18 and 19 and a patient's ribs apart.

Alternatives to the harmonic gear drive 20 include the use of a ratchet mechanism, a wrap spring mechanism or a lock nut mechanism (not shown) with the hub 14. Thus, a wrench or special tool can be attached to the upper hub half 17 to rotate it relative to the lower hub half 16 while the operator holds onto the spreader arm 18 or the lower hub half 16 with another wrench or special tool. Once the upper hub half 17 and spreader arm 19 are rotated to a desired position relative to the lower hub half 16 and spreader arm 18, the ratchet or wrap spring mechanism prevents reverse rotation of the upper hub half 17. If a lock nut mechanism is used, a lock nut is simply tightened to prevent reverse rotation after the upper hub half 17 is rotated relative to the lower hub half 16 to a desired position. Other alternatives, such as a lead-screw mechanism or worm gear mechanism, are discussed in detail below.

Referring to FIG. 2, the blades 50 and 51 preferably include elongated vanes 52 and 53, which slide beneath a plurality of the patient's ribs, and recessed arcuate throats 54 and 55 that receive the patient's ribs that are adjacent to the chest incision. The benefits of the recessed throats 54 and 55 and the elongated vanes 52 and 53 will be discussed below with regard to the operation of the access platform 10.

Blade arms 56 and 57 interconnect the blades 50 and 51 to the rest of the access platform 10. The blade arms 56 and 57 comprise stems 62 and 63 received in sockets 34 and 35 in torque bases 32 and 33. The sockets 34 and 35 and the stems 62 and 63 are constructed such that the blade arms 56 and 57 are releasably connected to the torque bases 32 and 33. The stems 62 and 63, which extend relatively horizontally from the torque bases 32 and 33, include pivot sections 60 and 61 extending therefrom. Branches 58 and 59 extend outwardly and downwardly away from the pivot sections 60 and 61 and are attached to the throats 54 and 55 of the blades 50 and 51. This blade arm construction advantageously directs the bulk of the access platform 10 away from the surgeon's working area.

The support pads 80 and 81 are connected to adjustable arms 86 and 87 by swivel connectors 82 and 83 that are preferably constructed as ball and socket type connectors 84 and 85. The adjustable arms 86 and 87 preferably include external shafts 88 and 89 slidably received over and operably connected to internal shafts 98 and 99. The external shafts 88 and 89 are preferably operably connected to the internal shafts 98 and 99 via a ratchet lever mechanism (not shown). The internal shafts 98 and 99 of the adjustable arms 86 and 87 are further connected to lock positioners 90 and 91. The lock positioners 90 and 91, which are attached to the torque bases 32 and 33, comprise a ratchet or a wrap spring type mechanism (not shown) or, alternatively, comprise opposing face gears 94 and 96, 95 and 97. Tabs 92 and 93 rotate and cooperate with cammed or serrated surfaces 36 and 37 on the outer face of the outer face gears 94 and 95 to engage and disengage the opposing face gears 94 and 96, 95 and 97. Thus, when the tabs 92 and 93 are rotated to disengage the face gears 94 and 96, 95 and 97, the support pads 80 and 81 can be rotated to a desired position. Once the support pads 80 and 81 are in position, the tabs 92 and 93 are rotated to engage the face gears 94 and 96, 95 and 97 and, thus, lock the support pads 80 and 81 in place.

The torsional members 30 and 31 are operably connected to the torque bases 32 and 33 and the spreader arms 18 and 19 to enable the access platform 10 to both laterally retract and vertically displace a patient's ribs. Thus, the torsional members 30 and 31 enable the access platform 10 to be advantageously self-contained such that the force necessary to spread and vertically displace a patient's ribs, and the force necessary to depress the patient's sternum, is applied by the access platform 10 itself rather than through additional external devices.

Figure 4:
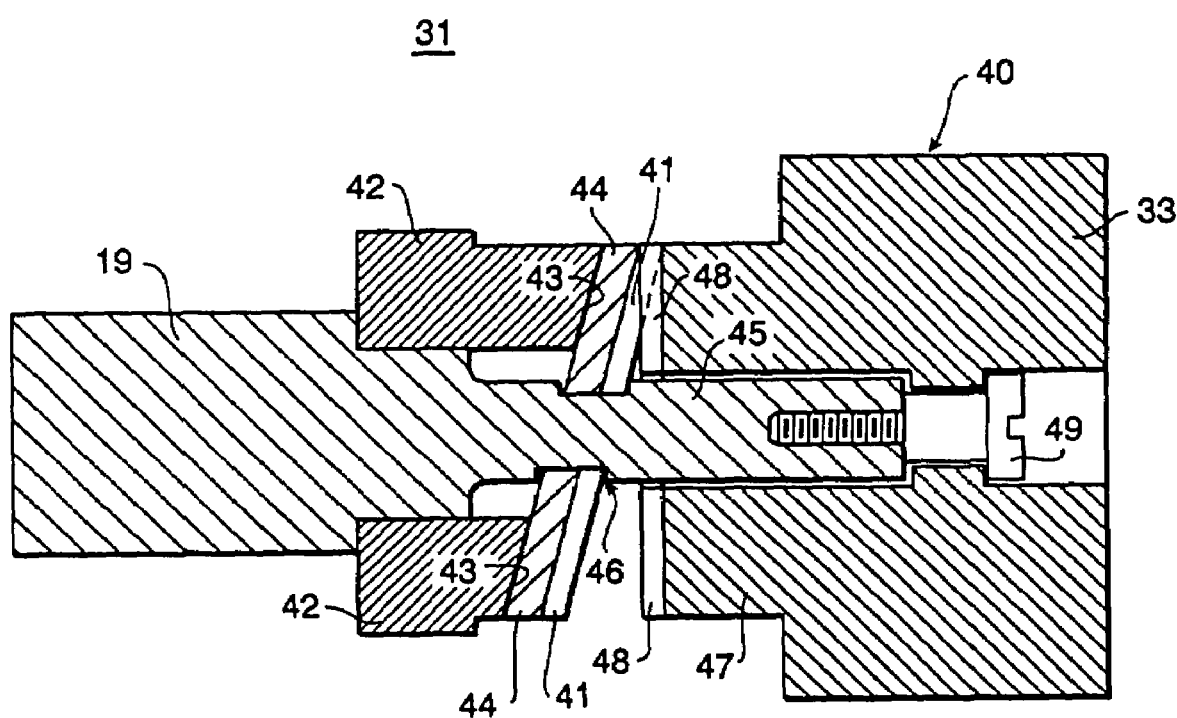
FIG. 4 is a cross-sectional view of a reduction gear assembly in the torsional element of the access platform taken along line 4-4 in FIG. 1.

The torsional members 30 and 31 preferably comprise a reduction gear assembly 40 (see FIG. 4). The reduction gear assembly 40, as shown for torsional member 31, comprises a drive nut 42 rotatably captured on the end of the shaft of the spreader arm 19, a first shaft 45 axially extending from the spreader arm 19, and a second shaft 47 extending from the torque base 33. The second shaft 47 is rotatably captured over the first shaft 45 by a shoulder screw 49.

The drive nut 42 preferably has a beveled face 43 that is adjacent to an end of the second shaft 47. A wobble plate 44 mounted on the first shaft 45 interposes the drive nut 42 and the second shaft 47. The wobble plate 44 is captured in splines 46 on the first shaft 45 to prevent the wobble plate 44 from rotating relative to the first shaft 45. The splines 46, however, do not restrict the wobble plate's 44 wobble motion.

The wobble plate 44 and the second shaft 47 include opposing operably connected face gears 41 and 48, respectively. The face gear 41 on the wobble plate 44 only meshes fully at one point with the face gear 48 on the second shaft 47 as the wobble plate 44 wobbles from the rotation of the drive nut 42. Thus, the interaction between the face gears 41 and 48 creates a gear ratio between the drive nut 42 and the second shaft 47 that is preferably in the range of about 60-80:1. Accordingly, only a relatively low torque is necessary to turn the drive nut 42 to rotate the second shaft 47, in either direction and, thus, rotate the torque base 32 and 33 with a torque necessary to vertically displace a patient's ribs with blades 50 and 51 and to depress a patient's sternum with the support pads 80 and 81.

Alternatively, the torsional members 30 and 31 could comprise a ratchet mechanism, a wrap spring mechanism or a lock nut mechanism (not shown) wherein a wrench or a special tool could be used to rotate the torque bases 32 and 33 to a desired position. Once the torque bases 32 and 33 are rotated to their desired positions, they are prevented from reverse rotation by the ratchet, wrap spring or lock nut mechanisms.

Figure 5:
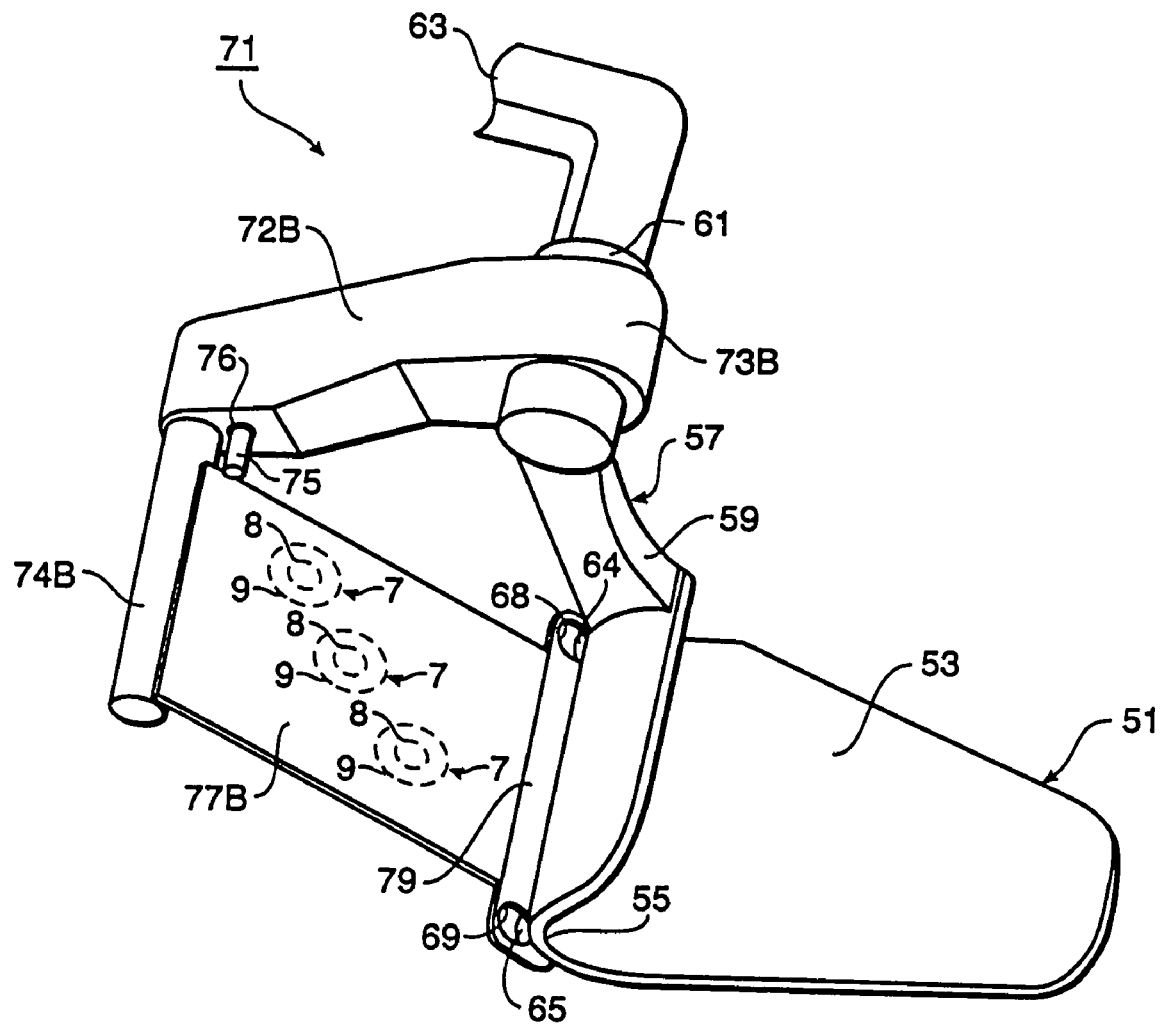
FIG. 5 is an isometric view of a blade, a blade arm and a tissue retractor assembly for an access platform.
Figure 6:
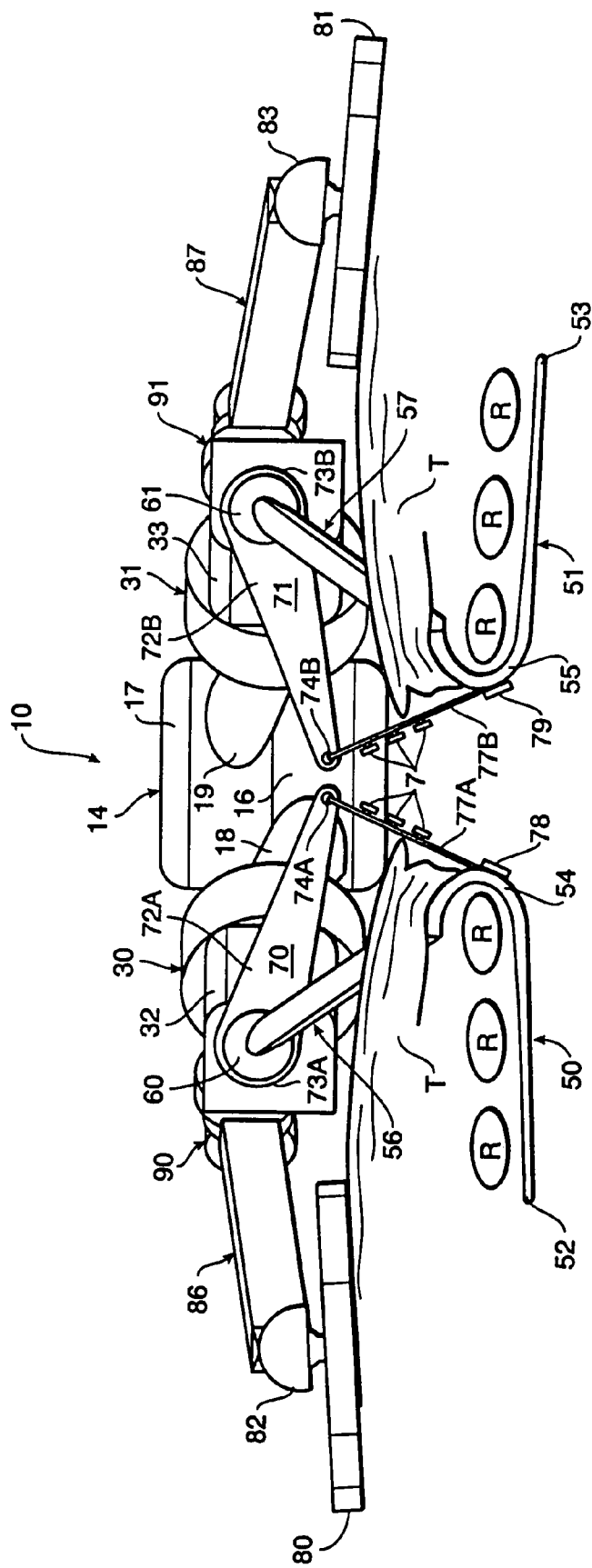
FIG. 6 is a front view of the access platform with the tissue retractors disengaged.
Figure 7:
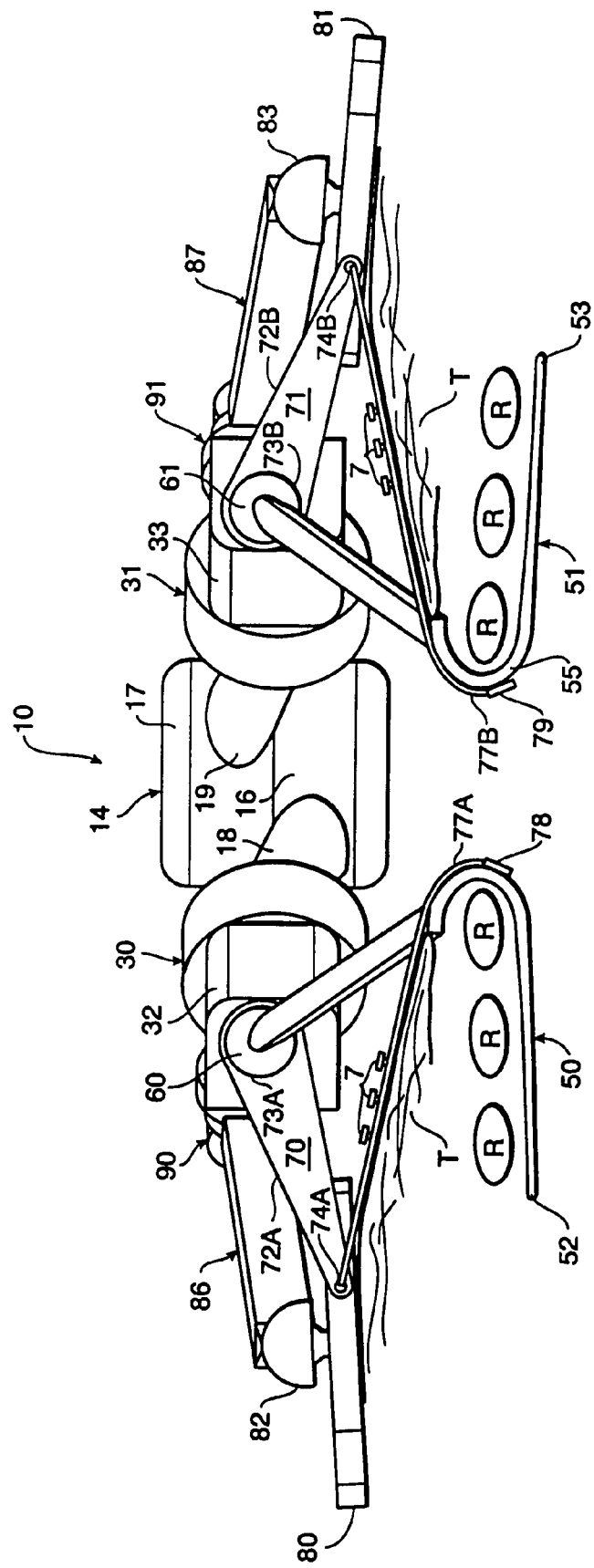
FIG. 7 is a front view of the access platform with the tissue retractors engaged.

Turning to FIGS. 5-7, the tissue retractors 70 and 71 comprise arms 72A and 72B extending from hubs 73A and 73B, respectively. The hubs 73A and 73B are rotatably mounted on the pivots 60 and 61 of the blade arms 56 and 57. At an end opposite to the hubs 73A and 73B, spindles 74A and 74B extend from the arms 72A and 72B. Elastic sheets 77A and 77B, preferably constructed from natural latex rubber, attach at one end to the spindles 74A and 74B, and at the opposite end to attachment plates 78 and 79. Slots 68 and 69 in the attachment plates 78 and 79 enable the attachment plates 78 and 79 to connect to the blades 50 and 51 by communicating with hooks 64 and 65 extending from the blades 50 and 51. As shown in FIG. 5, a locking pin 75 is attached in a parallel manner to the spindle 74B. The locking pin 75 communicates with a recess 76 in the arm 72B such that the spindle 74B can be rotated to take up excess slack in the elastic sheet 77B and, then, locked in place by mating the locking pin 75 with the recess 76. A locking pin (not shown) is similarly attached to the spindle 74A and a recess (not shown) is similarly formed in the arm 72A. Alternatively, the arms 72A and 72B would include a plurality of recesses (not shown) for greater adjustability.

The tissue retractors 70 and 71 include a plurality of low profile button cleats 7 formed in the top surface of the elastic sheets 77A and 77B. The cleats 7 include a stem 8 that extends upwardly from the elastic sheets 77A and 77B and a cap 9 that attaches to the stem 8. In operation, the surgeon can anchor sutures to the cleats 7 instead of anchoring the sutures to the patient's chest as is typically the case.

Figure 8:
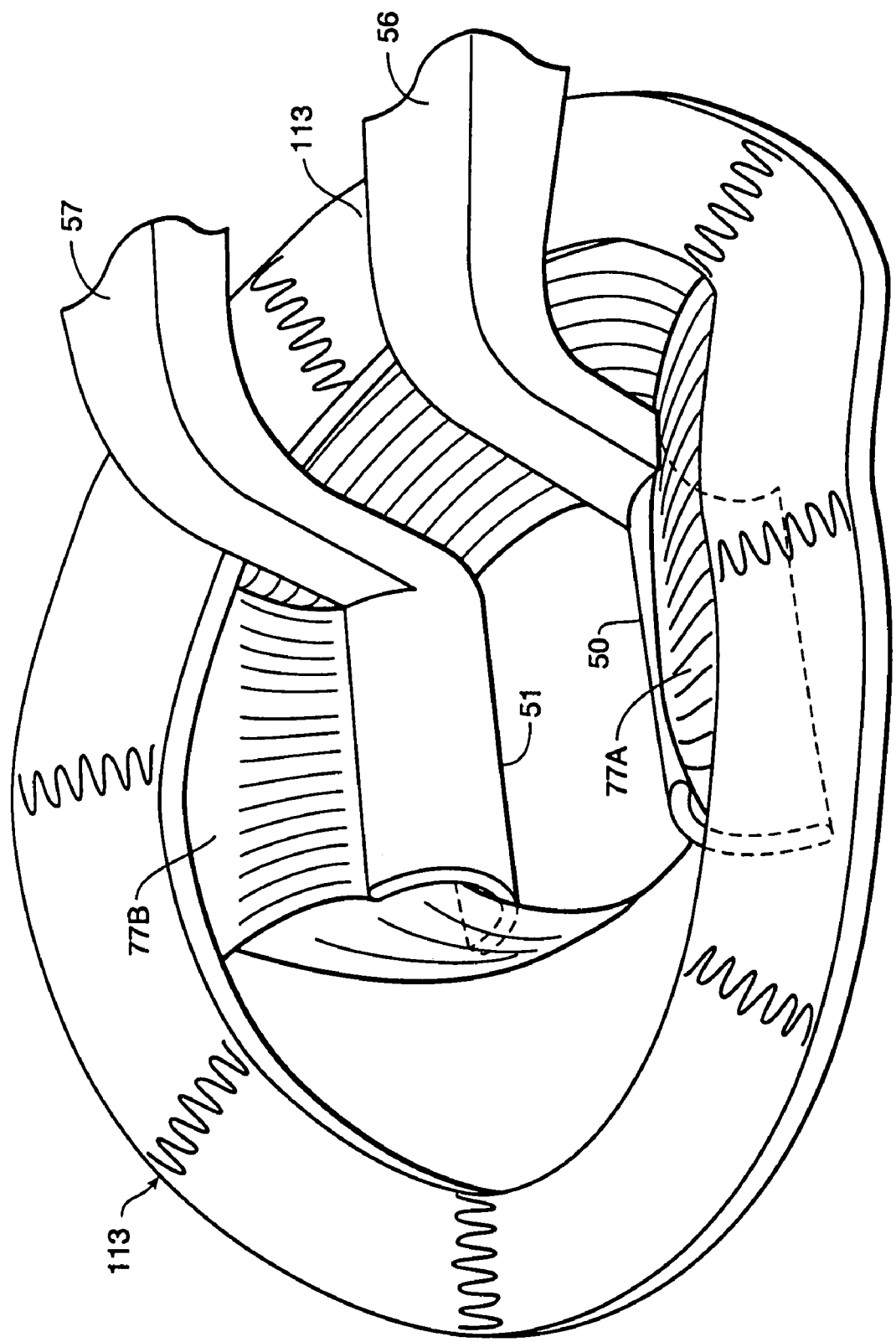
FIG. 8 is a partial isometric view of a tissue retractor and blades assembly for an access platform.

Turning to FIG. 8, the elastic sheets 77A and 77B of the tissue retractors 70 and 71 are alternatively attached to a multi-purpose flexible ring 113. The blades 50 and 51 are shown extending into an incision in the patient's chest from blade arms 56 and 57. The flexible ring 113 conforms to the contours of a patient's chest while outlining the surgeon's working space. The flexible ring 113 holds the elastic sheets 77A and 77B in an engaged position to retract tissue away from the working space. As a multi-purpose ring, the flexible ring 113 could be used as a base to mount surgical tools or hold sutures.

Figure 9:
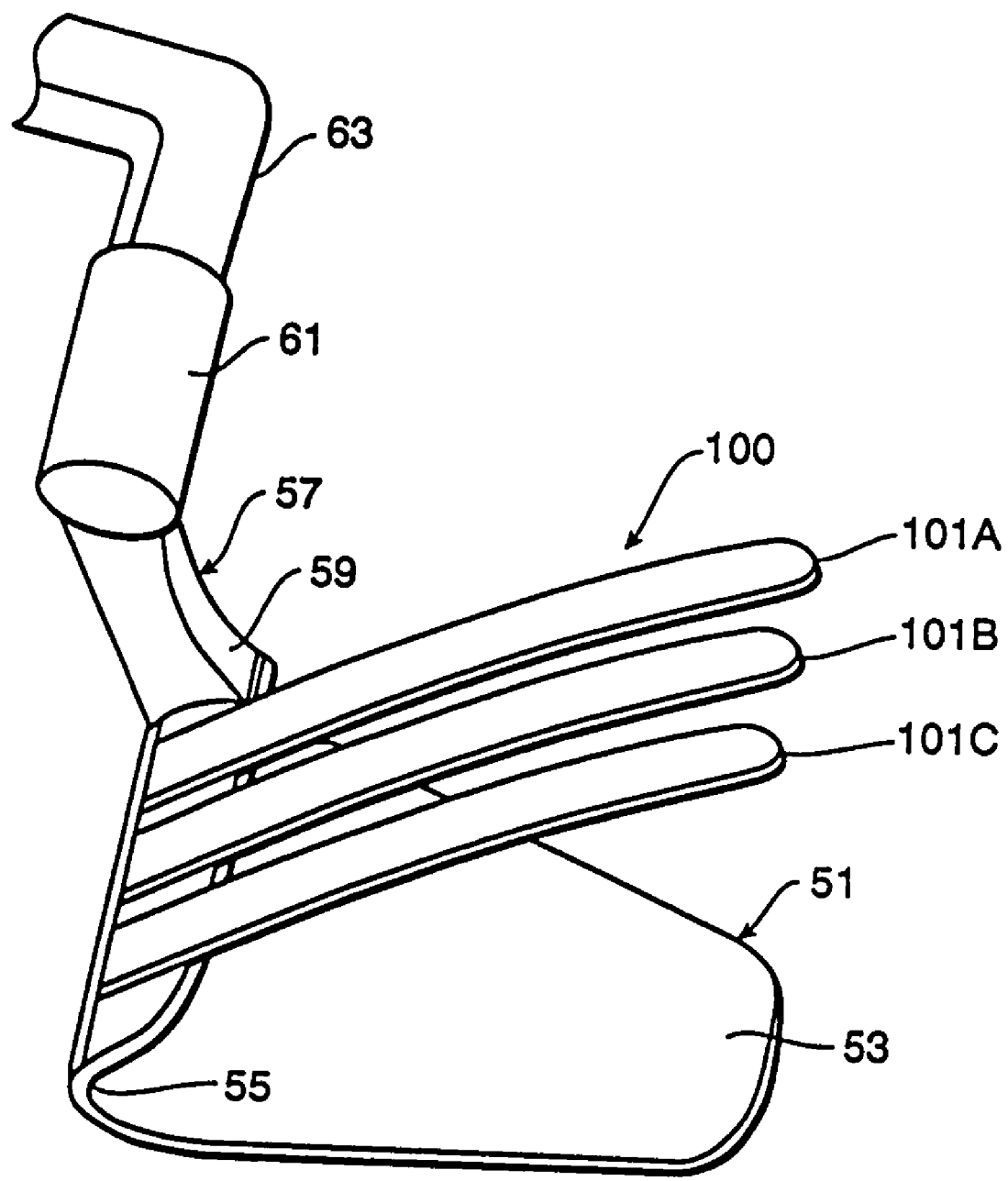
FIG. 9 is an isometric view of a tissue retractor assembly for an access platform.

As shown in FIG. 9, a tissue retractor 100 alternatively includes a plurality of malleable retractor fingers 101A, 101B and 101C extending upwardly from the throat section 55 of the blade 51. The retractor fingers are preferably constructed from annealed sheet metal approximately 0.035 inch thick. The fingers 101A, 101B and 101C are preferably welded onto the blades 51 or 50.

Prior to operation, the retractor fingers 101A, 101B and 101C extend relatively vertically from the blade 51 or 50. Once the blade 51 or 50 is in position, the retractor fingers 101A, 101B and 101C are bent over the patient's rib cage to retract the soft tissue adjacent to the incision area out of the surgeon's working space. Because of the thickness of the sheet metal, the retractor fingers 101A, 101B and 101C are easily deformed and retain their position once deformed.

Turning to FIGS. 10, 11 and 12, the tissue retractor 100 optionally includes a positioner assembly 103. The positioner assembly 103 includes a retractor base 104 mounted to the blade 51 by mounting pins 114. A semi-cylindrical guide 107 extends the length of the retractor base 104. The central portion 109 of the guide 107 is formed integrally with the retractor base 104. The outer portions of the guide 107, however, are formed in a spaced apart relation with the retractor base 104 and extend outwardly from the central portion 109 of the guide 107. A generally wedge-shaped brake 108 also extends the length of the retractor base 104.

The brake 108 is formed integrally with the guide 107 extending radially away from the guide at a narrowly formed flexure 106 which extends the length of the brake 108 and guide 107. A tab 105 located adjacent to the central portion 109 of guide 107 extends vertically from the brake 108.

A pair of sleeves 102A and 102B are rotatably received over the guide 107 and brake 108. The sleeves 102A and 102B are connected to or formed integrally with the retractor fingers 101A and 101C, respectively. The retractor fingers 101A and 101C are formed integrally with or are attached to a central retractor finger 101B. The brake 108 includes a radius 111 extending downwardly from the flexure 106. As the brake is rotated in the counterclockwise direction, the radius 111 exceeds the radius of the sleeves 102A and 102B.

In operation, pressure is applied to the fingers 101A, 101B and 101C of the tissue retractor 100 to rotate the fingers 101A, 101B, and 101C in a clockwise rotation about the positioner assembly 103 until the fingers 101A, 101B and 101C press against the tissue adjacent to the surgeon's working space. Clockwise rotation of the sleeves 102A and 102B causes the brake 108 to flex about flexure 106 and rotate in the clockwise direction and thus allow the sleeves to freely rotate about the guide 107 and the brake 108. However, counterclockwise rotation of the sleeves 102A and 102B is prevented by the brake 108. As the brake 108 rotates in a counterclockwise rotation about flexure 106, the radius 111 of the brake 108 will force the brake 108 into contact with the sleeves 102A and 102B, and thus prevent rotation of the sleeves 102A and 102B in the counterclockwise direction. To release the tissue retractor 100 from an engaged position, force is applied to the tab 105 to cause the brake 108 to rotate in the clockwise direction and flex about the flexure 106. By rotating in the clockwise direction, the brake 108 is drawn away from the sleeves 102A and 102B, and thus, the sleeves 102A and 102B are able to freely rotate about the positioner 103 in a counterclockwise direction. As will be readily apparent to those skilled in the art from the discussion herein, the tissue retractors described in regard to FIGS. 5-12 are adaptable for use with any of the embodiments of the access platform discussed herein.

Referring to FIG. 1, the access platform 10 preferably includes a port 66 shown mounted on one of the blade arms 56 adjacent to the pivot 60 (shown more clearly in FIG. 2). The port 66 can be used to mount a heart stabilizer instrument 67 for which a patent application has been filed. Additional ports located on the other blade arm 57 adjacent the pivot 61 or located adjacent to the blades 50 and 51 on both blade arms 56 and 57, may be desirable to mount other surgical instruments used in a "beating heart" CABG procedure, such as a scope for IMA take down, an IMA holder used to hold the IMA during the installation of the graft or a suture holder. The mounting of these instruments to the access platform 10 advantageously eliminates the need for an additional set of hands around the surgical site.

In operation, the blades 50 and 51 are positioned within the incision in the patient's chest such that the vanes 52 and 53 slide under the patient's ribs R (see FIGS. 6 and 7). The throats 54 and 55 of the blades 50 and 51 receive and substantially surround opposing ribs adjacent to the incision in the patient's chest. Once the blades 50 and 51 are in position, the blades 50 and 51 are connected to the rest of the access platform 10 by inserting the stems 62 and 63 (see FIG. 2) of the blade arms 56 and 57 into the sockets 34 and 35 in the torque bases 32 and 33.

Next, the hub 14 of the spreader member 12 is rotated to laterally spread the spreader arms 18 and 19 apart until the blades 50 and 51 have retracted the patient's ribs R to a desired spacing. The support pads 80 and 81 are then lowered to rest on the patient's chest and locked in place with lock positioners 90 and 91. At this point, the torque bases 32 and 33 are rotated relative to the torsional members 30 and 31 to displace in an essentially vertical direction the blades 50 and 51, and ultimately the patient's ribs R, relative to each other.

As the blade 51 is raised, the corresponding support pad 81 depresses the patient's sternum to cause a greater deflection in the patient's rib cage and, thus, increase the "tunnel" effect. The elongated vane construction of the blades 50 and 51 advantageously enables the access platform 10 to vertically raise a plurality of the patient's ribs R to cause a greater "tunnel" effect under a patient's rib cage and, thus, increases the surgeon's working area and visual access to the IMA. The recessed throat construction of the blades 50 and 51 advantageously enables the access platform 10 to vertically displace the opposite rib that is adjacent to the chest incision downwardly to further increase the surgeon's visual access. This combined motion helps to create an optimum tunnel.

After the ribs have been offset, the tissue retractors 70 and 71 or 100 are operated to retract the soft tissue T away from the incision area by either rotating the arms 72A and 72B about the pivots 60 and 61 on the blade arms 56 and 57 (See FIGS. 5-7) or bending or rotating the retractor fingers 101A, 101B and 101C (see FIGS. 9-12) over the patient's chest. By rotating the arms 72A and 72B about the pivots 60 and 61, the elastic sheets 77A and 77B advantageously grab, pull and press down against the soft tissue T adjacent to the incision to retract it away from the incision and out of the surgeon's working area. The over-center positioning of the arms 72A and 72B about the hubs 73A and 73B, effectively locks the tissue retractors 70 and 71 in place during use. By deforming or displacing the retractor fingers 101A, 101B and 101C, the fingers advantageously press down against the soft tissue adjacent to the incision to retract it away from the incision and out of the surgeon's working area.

In a first offset position, the blade 51 raises the retracted ribs and the blade 50 depresses the retracted ribs so that the surgeon can dissect the proximal portion of the IMA. Next, the blades 50 and 51 are rotated to a second offset position wherein the blade 50 raises the retracted ribs and the blade 51 depresses the retracted ribs. In this offset position, the surgeon takes down the distal portion of the IMA. With the dissection of the IMA complete, the surgeon levels the blades 50 and 51 and then engages the heart stabilizer 67 (See FIG. 1). With the heart stabilizer 67 engaged to minimize the movement of the heart, the surgeon performs an arteriotomy and an anastomosis. After completion of the arteriotomy and anastomosis, the surgeon removes the stabilizer 67, disengages the soft tissue retractors 70 and 71 or 100, and brings the blades 50 and 51 together. The blades 50 and 51 are then disengaged from the access platform 10 and removed from the interior of the patient's chest. With the blades 50 and 51 removed, the surgeon is able to sew up the thoracotomy and complete the surgical procedure.

Figure 13:
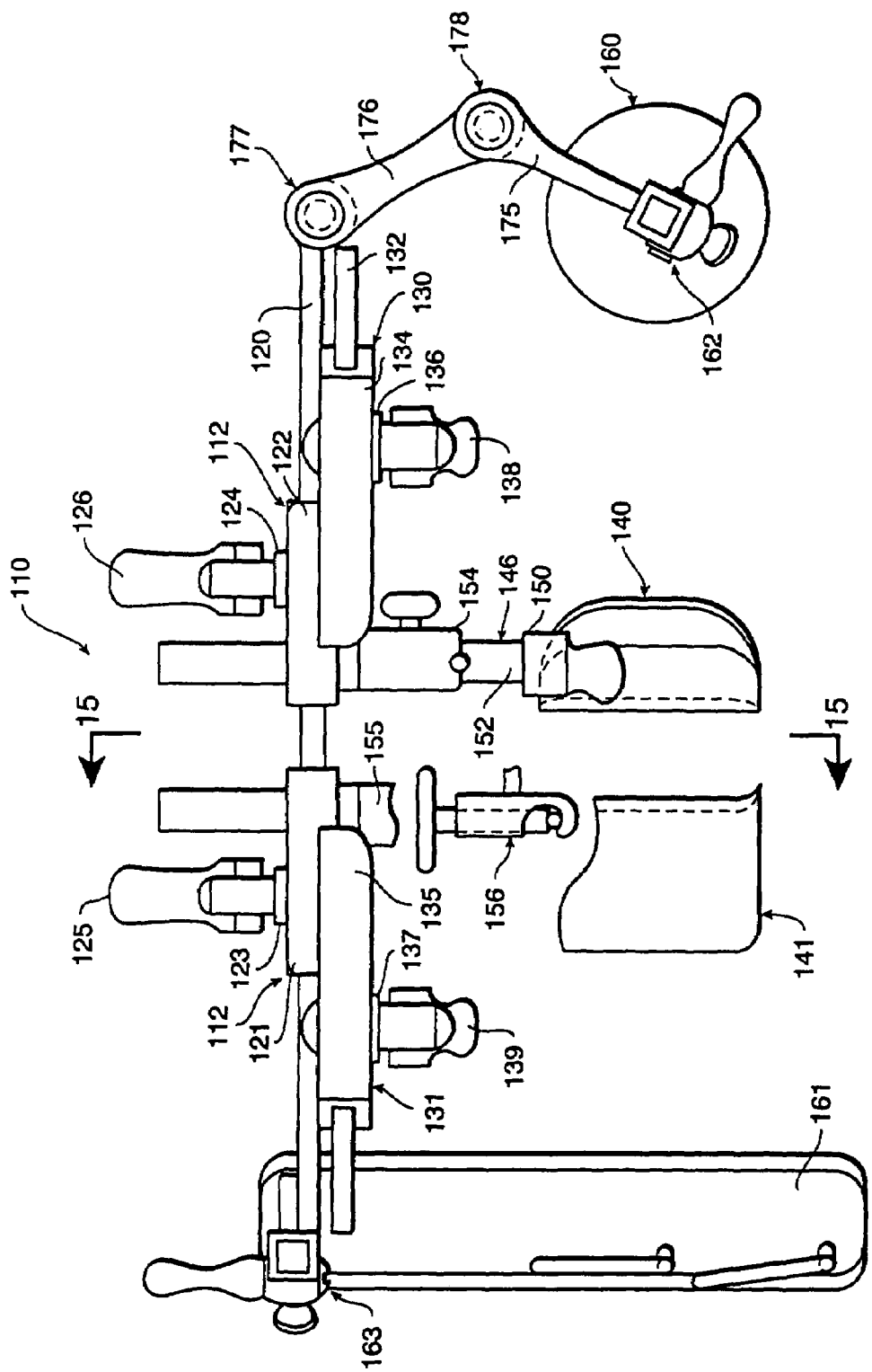
FIG. 13 is a top view of a second embodiment of the access platform of the present invention.
Figure 14:
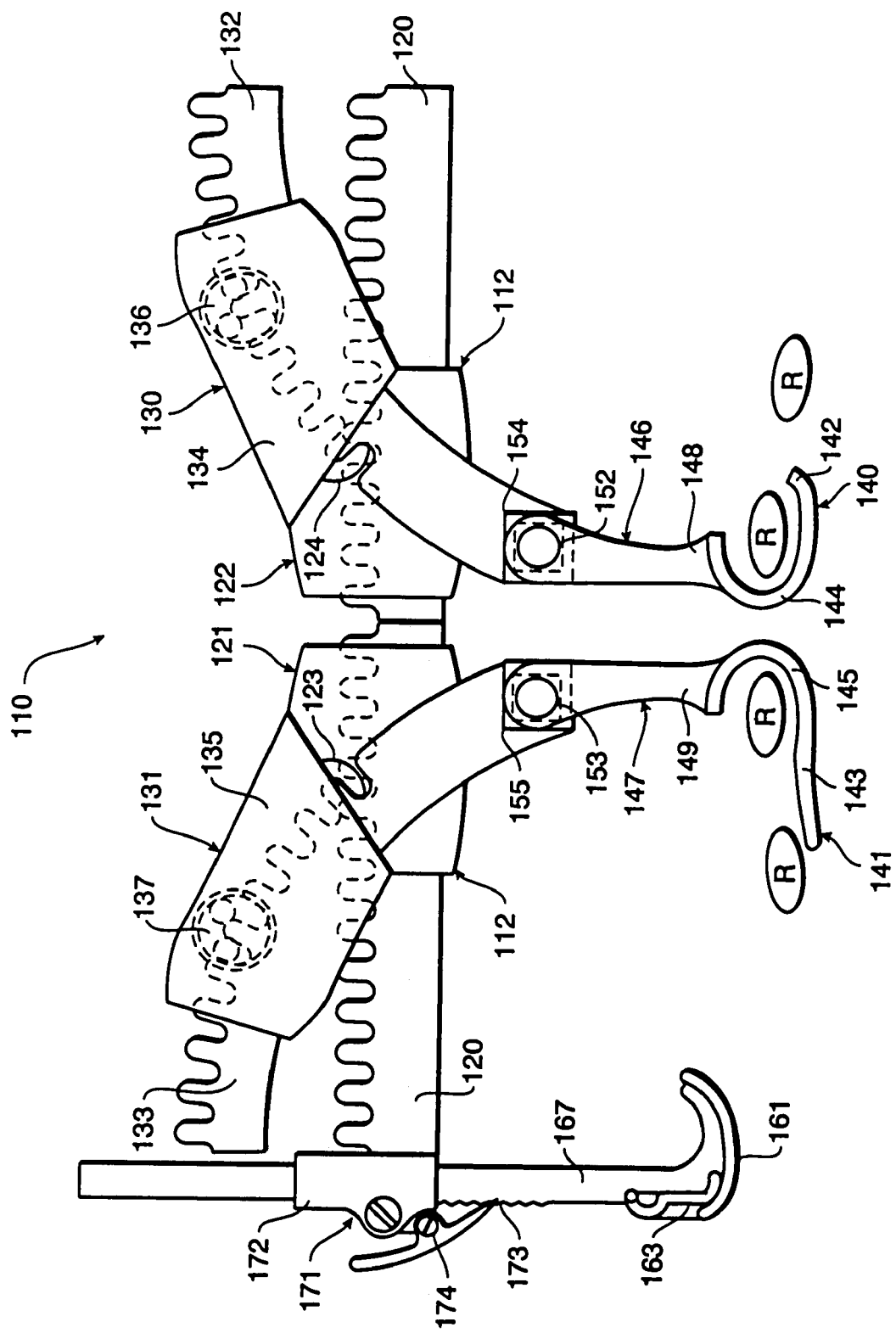
FIG. 14 is a partial front view of the access platform in FIG. 13.
Figure 15:
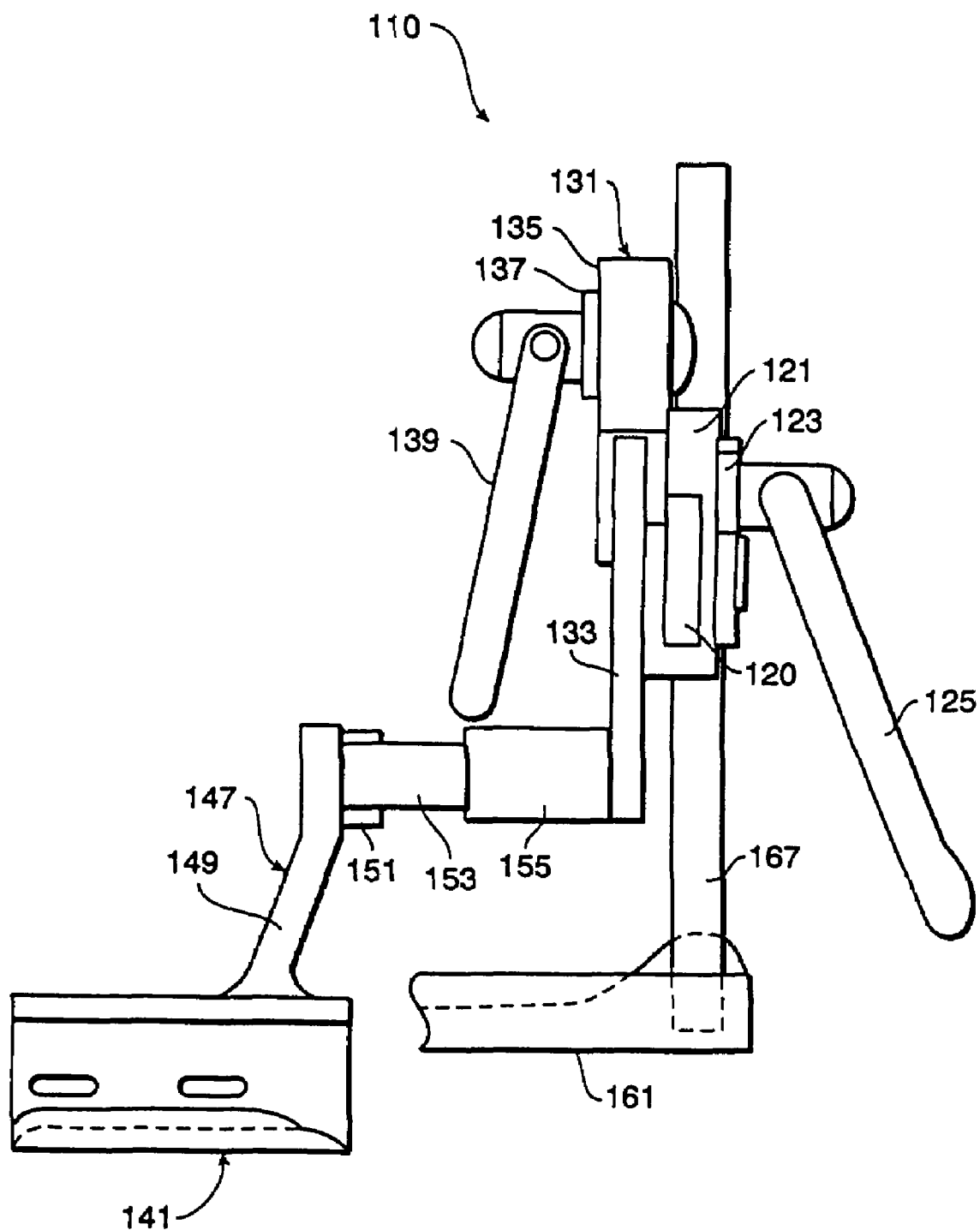
FIG. 15 is a side view of the access platform as viewed along a line 15-15 in FIG. 13.

A second embodiment of the access platform 110 is shown in FIGS. 13, 14 and 15. The second embodiment of the access platform 110 includes a spreader member 112 preferably comprising a horizontally disposed rack 120 and pinion housings 121 and 122 slidably disposed over the rack 120. The pinion housings 121 and 122 rotatably retain pinions 123 and 124 driven by levers 125 and 126.

Vertical displacement members 130 and 131 preferably comprise curved racks 132 and 133 slidably received within pinion housings 134 and 135. The pinion housings 134 and 135 are fixedly attached to the pinion housings 122 and 121.

The pinion housings 134 and 135 rotatably retain pinions 136 and 137 driven by levers 138 and 139. Sockets 154 and 155 are formed in the lower ends of the curved racks 132 and 133. Stems 152 and 153 of blade arms 146 and 147 are releasably received by and horizontally extend from the sockets 154 and 155.

The blade arms 146 and 147 further comprise pivot sections 150 and 151 extending horizontally from the stems 152 and 153. Branches 148 and 149 extend downwardly and outwardly from the pivot sections 150 and 151 of the blade arms 146 and 147 to position the remainder of the access platform 110 away from the surgeon's working area. Branches 148 and 149 attach to blades 140 and 141. The blades 140 and 141 comprise elongated vane sections 142 and 143 extending outwardly from recessed throat sections 144 and 145.

Preferably, one end of the horizontally disposed rack 120 is connected to a slide 172 of a lock positioner 171. The slide 172 is slidably received over a vertically disposed support pad stanchion 167. The stanchion 167 has ratchet gear teeth 173 formed thereon which cooperate with a pawl 174 attached to the slide 172 to adjustably position the support pad 161. The support pad 161 is adjustably connected to the stanchion 167 by a swivel connector 163.

The opposing end of the horizontally disposed rack 120 is preferably connected to a support pad link 176 via a lockable ball and socket joint 177. The support pad link 176 is further connected to a second support pad link 175 via a hinge joint 178. This link and joint assembly allows for the multiple positioning of the support pad 160. The support pad 160 is further connected to the support pad link 175 via a swivel connector 162.

In addition, the access platform 110 includes a mount 156, attached to the blade arm 147. The mount 156 enables the access platform 110 to hold a heart stabilizer tool 67 shown in FIG. 1, an IMA holder, an IMA scope, a suture holder, or other surgical instruments used in a "beating heart" CABG procedure. Thus, the mount 156 advantageously eliminates the need for an undesirable extra set of hands around the surgical site.

In operation, the blades 140 and 141 are inserted in an incision in the patient's chest such that the blade vanes 142 and 143 slide under the patient's ribs and the recessed throats 144 and 145 of the blades 140 and 141 capture the ribs that are adjacent to the incision. After the blades 140 and 141 are properly positioned, the stems 152 and 153 of the blade arms 146 and 147 are inserted into the sockets 154 and 155 of the vertical displacement members 130 and 131 to connect the blades 140 and 141 to the remainder of the access platform 110. The levers 125 and 126 are then rotated to drive the pinions 121 and 122 over the rack 120 to laterally retract the ribs. When a desired spacing between the retracted ribs is met, the support pads 160 and 161 are positioned on the chest of the patient, with support pad 160 being preferably positioned on the patient's sternum. The levers 138 and 139 are then rotated to drive the pinions 136 and 137 to draw the curved racks 132 and 133 through the pinion housing 134 and 135 to vertically displace the blades 140 and 141 and the retracted ribs. As the blade 140 is retracted upwards the support pad 160 preferably depresses the sternum creating a greater deflection in the patient's rib cage and, thus, creating a greater "tunnel" effect underneath the patient's rib cage, to increase the surgeon's working space and visual access for dissection of the IMA.

As in the first embodiment, after the ribs have been vertically displaced, tissue retractors 70, 71 or 100 (shown in FIGS. 5-12) are operated to retract the soft tissue away from the incision area by either rotating the arms 72A and 72B about the pivots 150 and 151 on the blade arms 146 and 147 or bending or displacing the fingers 101A, 101B, and 101C over the patient's chest. By rotating the arms 72A and 72B about the pivots 150 and 151, the elastic sheets 77A and 77B advantageously grab, pull, and press down against the soft tissue to retract it away from the incision and out of the surgeon's working area. By bending or displacing the retractor fingers 101A, 101B and 101C over the patient's chest the fingers 101A, 101B and 101C advantageously press down against the soft tissue to retract it away from the incision and out of the surgeon's working area.

In a first offset position, the blade 141 raises the retracted ribs and the blade 140 depresses the retracted ribs so that the surgeon can dissect the proximal portion of the IMA. Next, the blades 140 and 141 are adjusted to a second offset position wherein the blade 140 lifts the retracted ribs and the blade 141 depresses the retracted ribs. In the second offset position, the surgeon takes down the distal portion of the IMA. With the dissection of the IMA complete, the surgeon levels the blades 140 and 141 and then engages the heart stabilizer 67 shown in FIG. 1. With the heart stabilizer 67 engaged to minimize the movement of the heart, the surgeon performs an arteriotomy and anastomosis. After completion of the arteriotomy and anastomosis, the surgeon removes the stabilizer 67, disengages the soft tissue retractors 70 and 71 and brings the blades 140 and 141 together. The blades 140 and 141 are then disengaged from the access platform 110 and then removed from the interior of the patient's chest. With the blades 140 and 141 removed, the surgeon is able to sew up the thoracotomy and complete the surgical procedure.

Figure 16:
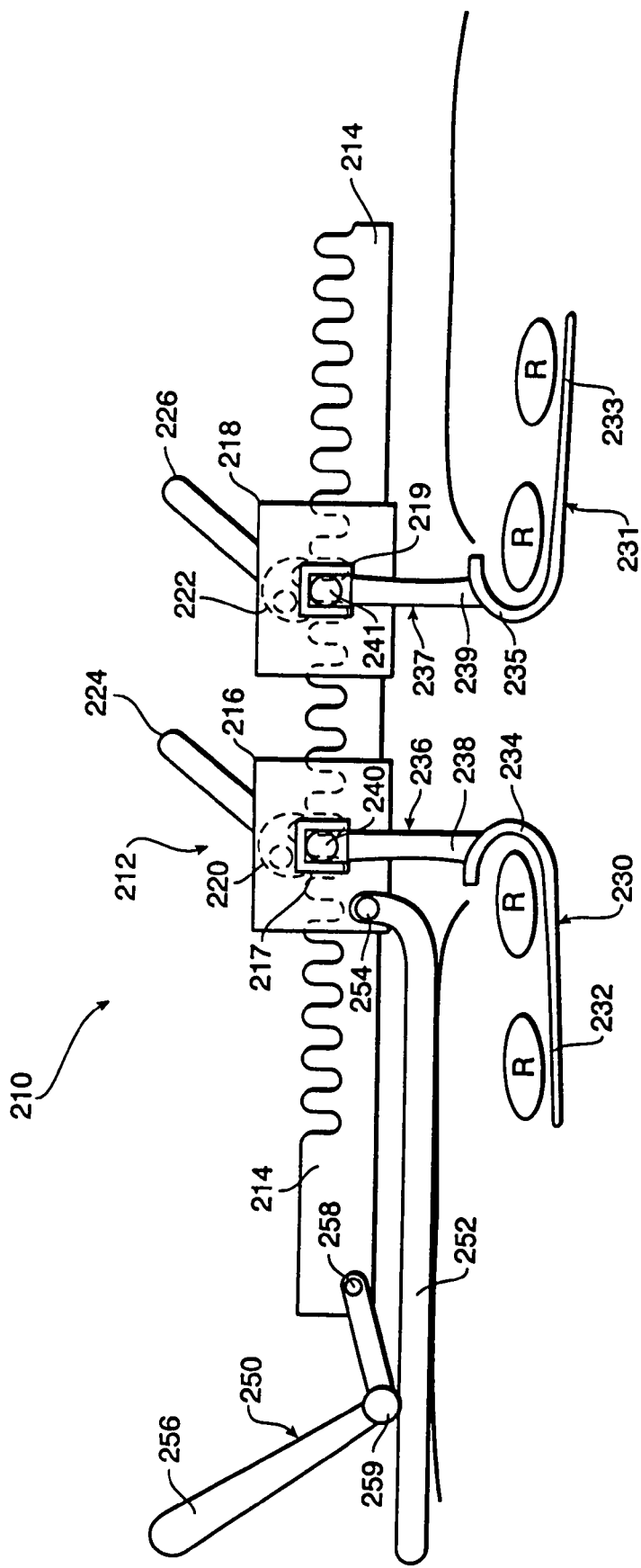
FIG. 16 is a front view of a third embodiment of the access platform of the present invention.
Figure 17:
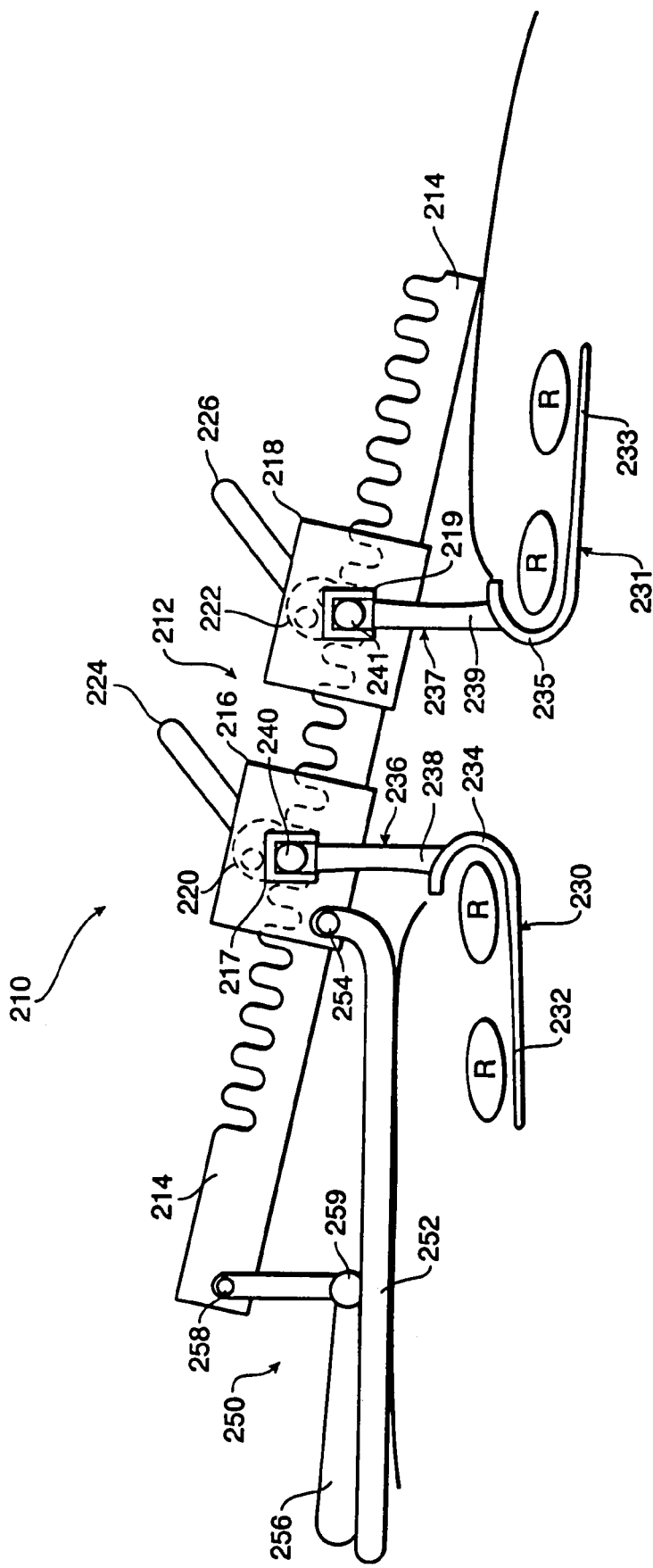
FIG. 17 is a front view of the access platform shown in FIG. 16 with a vertical displacement member engaged.

A third embodiment of the access platform 210 is shown in FIGS. 16 and 17. The third embodiment of the access platform 210 includes a spreader member 212 comprising a horizontally-disposed rack 214 and pinion housings 216 and 218 slidably disposed over the rack 214. Pinions 220 and 222 are rotatably retained in the pinion housings 216 and 218 and driven by levers 224 and 226.

Blades 230 and 231 comprise elongated vane sections 232 and 233 extending from recessed throat sections 234 and 235. Blade arms 236 and 237 have branches 238 and 239 that extend downwardly and outwardly from horizontally disposed stems 240 and 241 and connect to the blades 230 and 231. The stems 240 and 241 of the blade arms 236 and 237 are releasably received in sockets 217 and 219 formed in the pinion housings 216 and 218.

A vertical displacement member 250 comprises a support pad 252 that pivotally connects to the pinion housing 216 at a pivot 254 and extends laterally away from the pinion housing 216. An "L"-shaped lever 256 is pivotally connected to the rack 214 at a pivot 258 at the end of the short leg of the "L"-shaped lever 256. A slide 259 is formed at the intersection of the short and long legs of the "L"-shaped lever 256. The slide 259 slidably contacts the support pad 252.

In operation, the blades 230 and 231 are inserted into the chest incision and positioned such that the vane sections 232 and 233 slide under the patient's ribs R and the recess throat sections 234 and 235 capture the patient's ribs R adjacent to the incision. Once the blades 230 and 231 are properly in place, the stems 240 and 241 of the blade arms 236 and 237 are inserted into the sockets 217 and 219 of the pinion housings 216 and 218. Next, the levers 224 and 226 are rotated to drive pinions 220 and 222 along the rack 214 to laterally retract the ribs. The "L"-shaped lever 256 is then rotated downwardly in a counterclockwise direction toward the patient's chest such that the slide portion 259 slides along the support pad 252 toward the housing 220 while the "L"-shaped lever 256 rotates about the pivot 258. As a result, one end of the rack 214 is raised to vertically offset blade 230 and ribs R relative to the blade 231 and ribs R.

As with the first two embodiments, the tissue retractors 70, 71 or 100 can be used with this embodiment of the access platform 210 to retract soft tissue away from the incision and the surgeon's working area.

Figure 18:
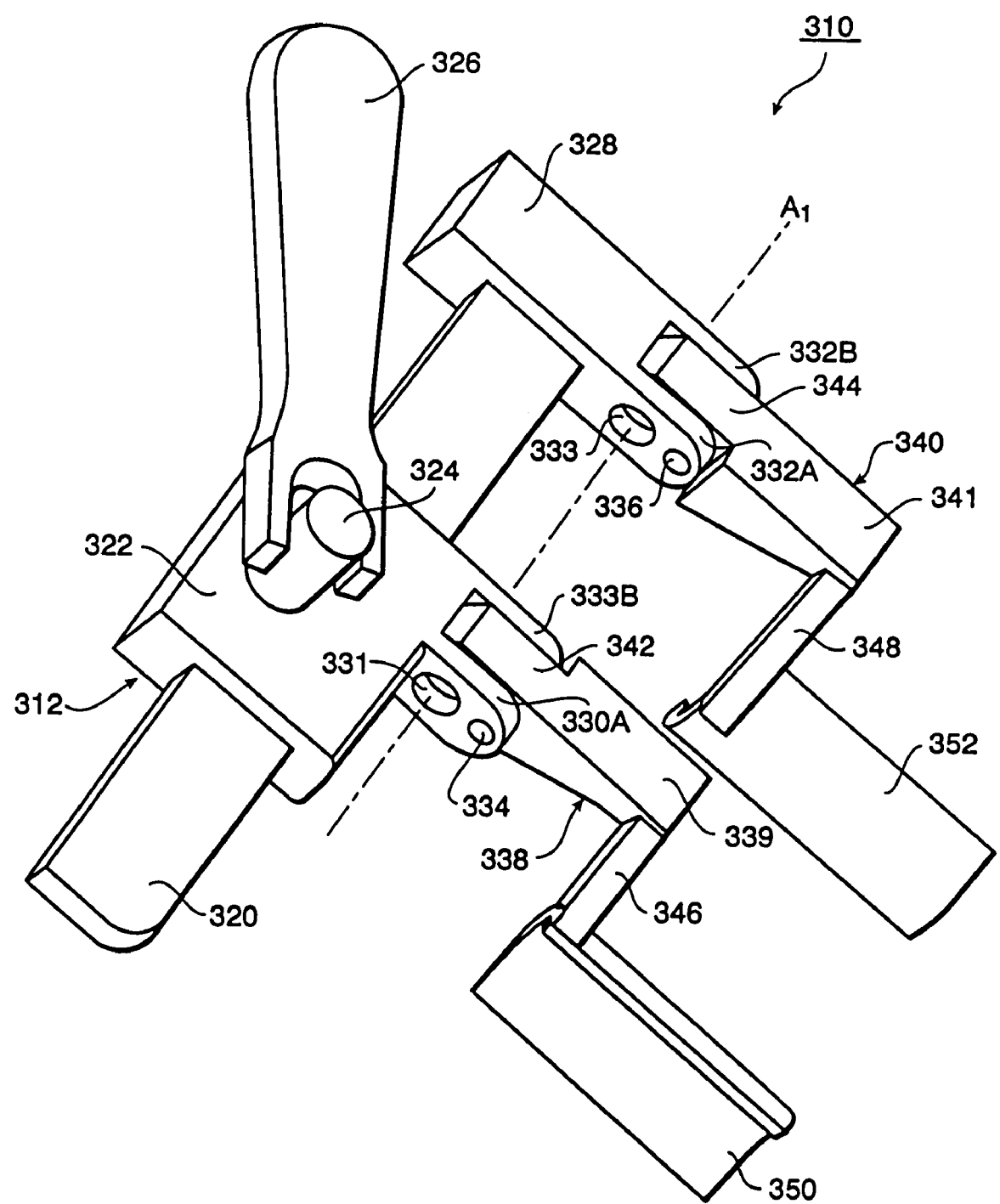
FIG. 18 is an isometric view of a fourth embodiment of the access platform of the present invention.

A fourth embodiment is shown in FIG. 18. The access platform 310 of the fourth embodiment includes a spreader member 312 comprising a rack 320, a housing 322 slidably received over the rack 320, a pinion 324 rotatably retained in the housing 322 and a lever 326 connected to the pinion 324. A spreader base 328 is attached to one end of the rack 320. A pair of parallel spaced fingers 330A and 330B extend from the housing 322. Similarly, a pair of parallel spaced fingers 332A and 332B extend from the spreader base 328 and are positioned parallel to the fingers 330A and 330B extending from the housing 322.

A pair of blade arms 338 and 340 include branch sections 346 and 348 that extend downwardly from central portions 339 and 341 and connect to blades 350 and 352. Stem portions 342 and 344 extend from the central portions 339 and 341 opposite the branch sections 346 and 348. The stem 342 extends between and is pivotally mounted to fingers 330A and 330B at a pivot 331. Likewise, stem 344 extends between and is pivotally mounted to fingers 332A and 332B at a pivot 333. As a result, the blade arms 338 and 340 rotate about an axis of rotation $A_1$ that is parallel to the rack 320. This construction advantageously enables the access platform 310 to address a thoracotomy positioned anywhere along the chest wall without intruding on the surgeon's working space. If the thoracotomy is located on the lateral side of the chest wall the spreader member 312, the spreader base 328 and the housing 322 are simply pivoted away from the surgeon's working space.

If desired, locking pins 334 and 336 can be used to immobilize the blade arms 338 and 340 and fix them relative to the housing 322 and the spreader base 328.

Figure 19:
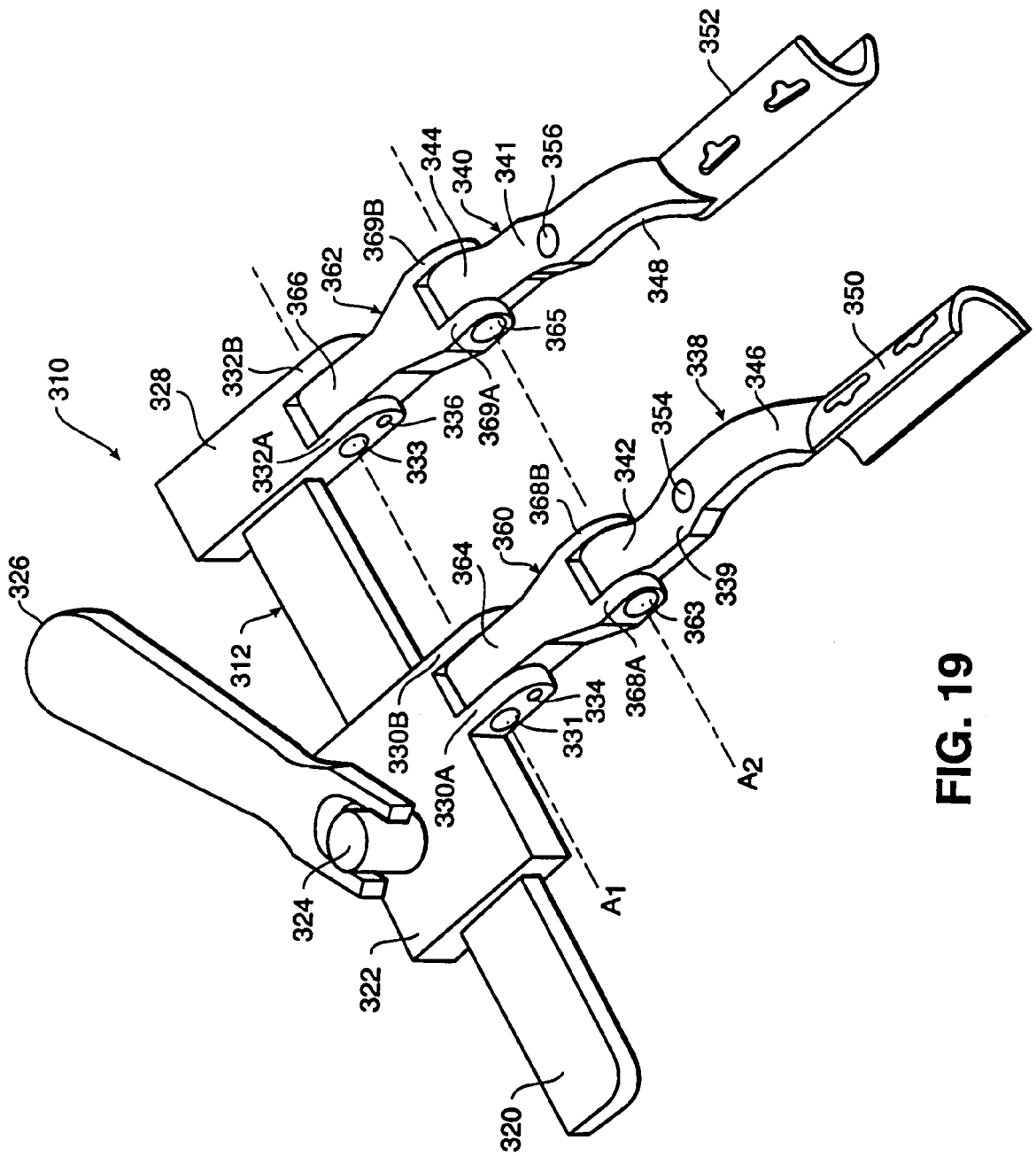
FIG. 19 is an isometric view of a fifth embodiment of the access platform of the present invention.

As shown in FIG. 19, a fifth embodiment of the access platform 310 modifies the fourth embodiment shown in FIG. 18 to include a pair of links 360 and 362 interposed and hingedly interconnected to the blade arms 338 and 340 and the housing 322 and spreader base 328, respectively. The links 360 and 362 comprise link bodies 364 and 366 and parallel spaced fingers 368A and 368B and 369A and 369B, respectively, extending from the link bodies 364 and 366. The link bodies 364 and 366 extend between and pivotally mount to the fingers 330A and 330B and 332A and 332B at pivots 331 and 333, respectively. Likewise, the stems 342 and 344 of the blade arms 338 and 340 extend between and pivotally mount to the fingers 368A and 368B and 369A and 369B at pivots 363 and 365, respectively. As a result, the blade arms 338 and 340 and the links 360 and 362 rotate about parallel axes of rotation $A_1$ and $A_2$ that are parallel to the rack 320. This construction further enables the access platform 310 to address a thoracotomy positioned anywhere along the chest wall without intruding on the surgeon's working space by easily pivoting the spreader base 328, the housing 332 and the rack 320 out of the surgeon's way.

Ports 354 and 356 are included on the blade arms 338 and 340 to mount a heart stabilizer tool 67 shown in FIG. 1, an IMA holder, an IMA scope, a suture holder, or other surgical instruments used in a "beating heart" CABG procedure. Thus, the ports 354 and 356 advantageously eliminate the need for an undesirable extra set of hands around the surgical site.

Figure 20:
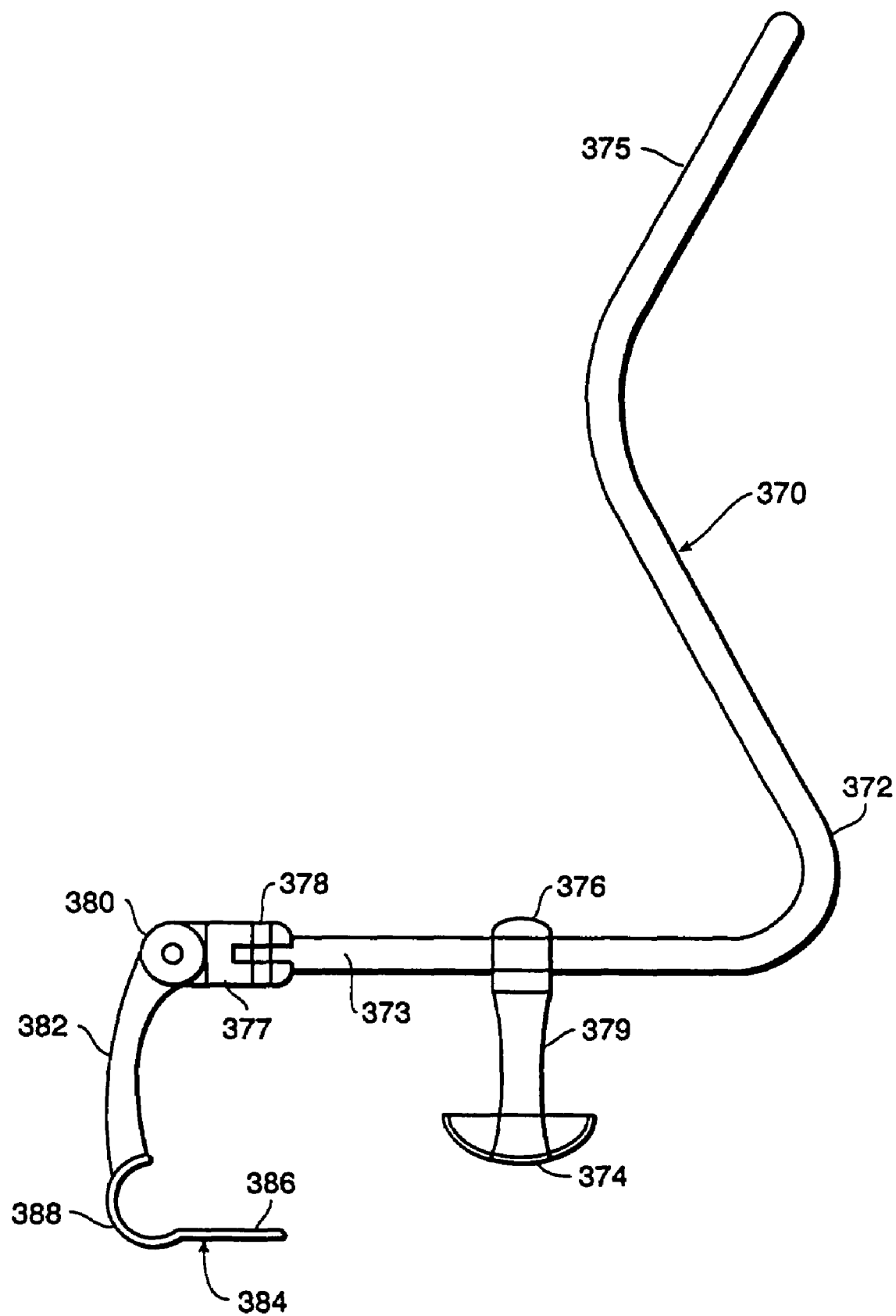
FIG. 20 is an elevation view of a pry bar for engaging the blade and blade arm of the access platform in FIG. 18.
Figure 21:
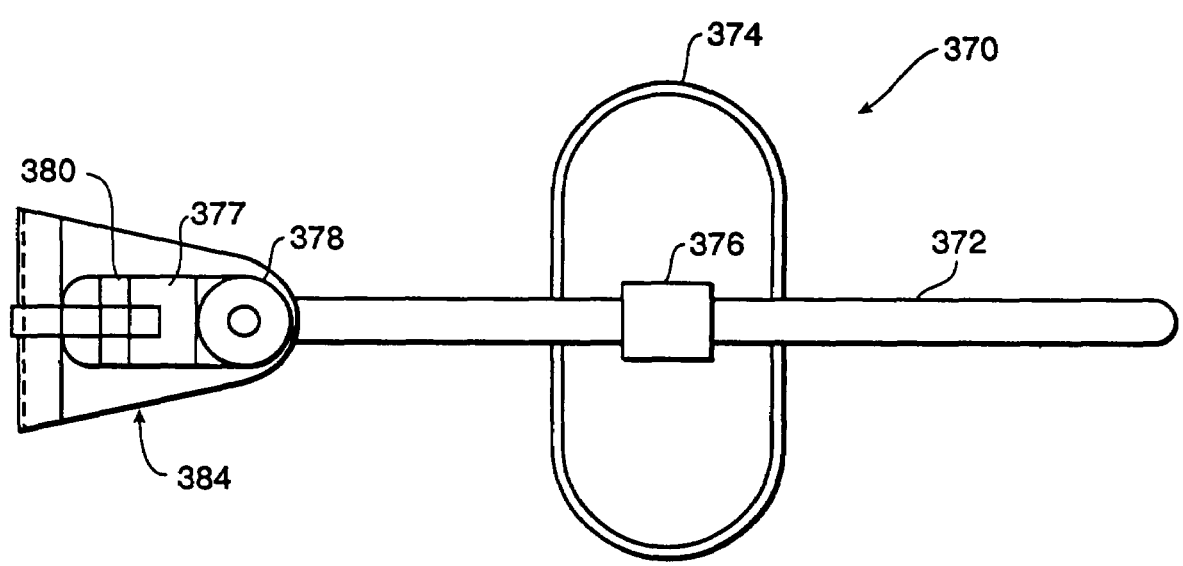
FIG. 21 is a top view of the pry bar in FIG. 20.

Turning to FIGS. 20 and 21, a pry bar 370, which is used in conjunction with the access platform 310 shown in FIG. 18 or 19 to offset a patient's ribs, comprises a generally "S"-shaped body 372 pivotally connected to a pivot base 377 at pivot 378. The pivot base 377 is in turn pivotally connected to a blade arm 382 at pivot 380. The blade arm 382 extends downwardly from the pivot 380 and connects to a blade 384. The blade 384 includes an elongated vane 386 and a deep recessed throat 388. A sternal pad 374 is connected to a post 379 that is slidably mounted on the lower portion 373 of the "S"-shaped body 372 via a slide 376.

In operation, the blade 384 is positioned such that the throat 388 captures the blade 350 or 352 of the access platform 310. As the throat 388 captures the blade 350 or 352 the elongated vane 386 extends under a plurality of the patient's ribs to be offset. The pivot base 377 and the pivots 378 and 380 enable the pry bar 370 to be adjustably positioned about two different axes of rotation.

Once the blade 384 is positioned, the sternal pad 374 is adjustably located to atraumatically conform the pry bar 370 to the anatomy of the patient. Once the sternal pad 374 is in position, a handle 375, in the upper portion of the "S"-shaped body 372, is pulled to pivot the pry bar 370 about the sternal pad 374 and lift the blade 384 and the blade 350 or 352 of the access platform 310 to offset the patient's ribs and create a "tunnel" to increase the surgeon's working space and visual access for the dissection of the IMA.

Figure 22:
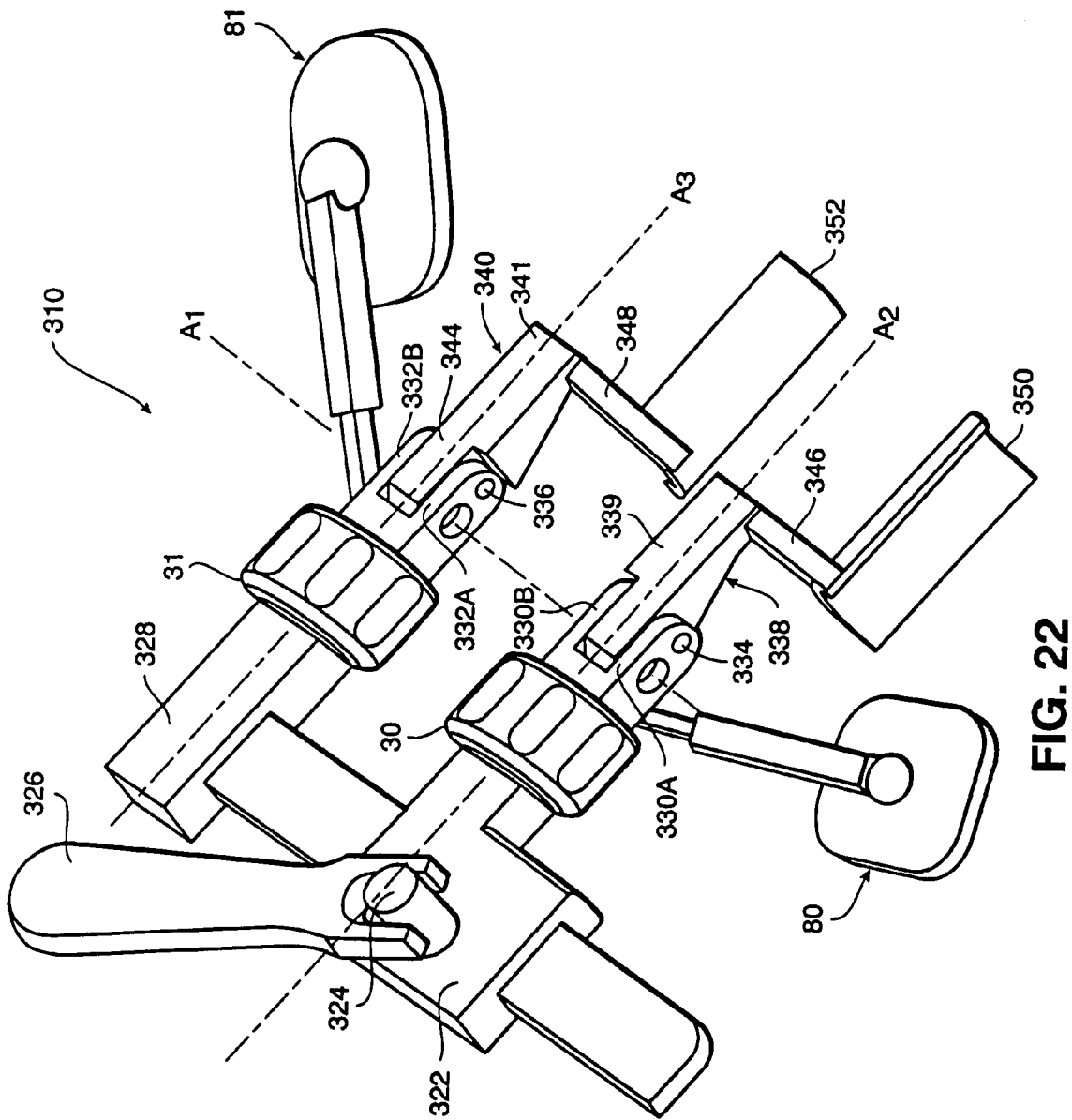
FIG. 22 is an isometric view of a sixth embodiment of the access platform of the present invention.

A sixth embodiment of the access platform 310 is shown in FIG. 22 to comprise a combination of components from the first and fourth embodiments (FIGS. 2 and 18). More particularly, the torsional members 30 and 31 of the first embodiment are interposed between and operably connected to the fingers 330A and 330B and the housing 322, and interposed between and operably connected to the fingers 332A and 332B and the spreader base 328, respectively. In addition, the support pads 80 and 81 of the first embodiment are adjustably attached to the fingers 330A and 330B, 332A and 332B. By including the torsional members 30 and 31 and the support pads 80 and 81, second and third axes of rotation $A_2$ and $A_3$ are provided. Thus, as in the first embodiment, the torsional members 30 and 31 enable the access platform 310 to vertically displace the blades 350 and 352 and the retracted ribs. To vertically displace the blades 350 and 352, the blade arms 338 and 340 are fixedly coupled to the fingers 330A and 330B, 332A and 332B by pins 334 and 336.

Figure 23:
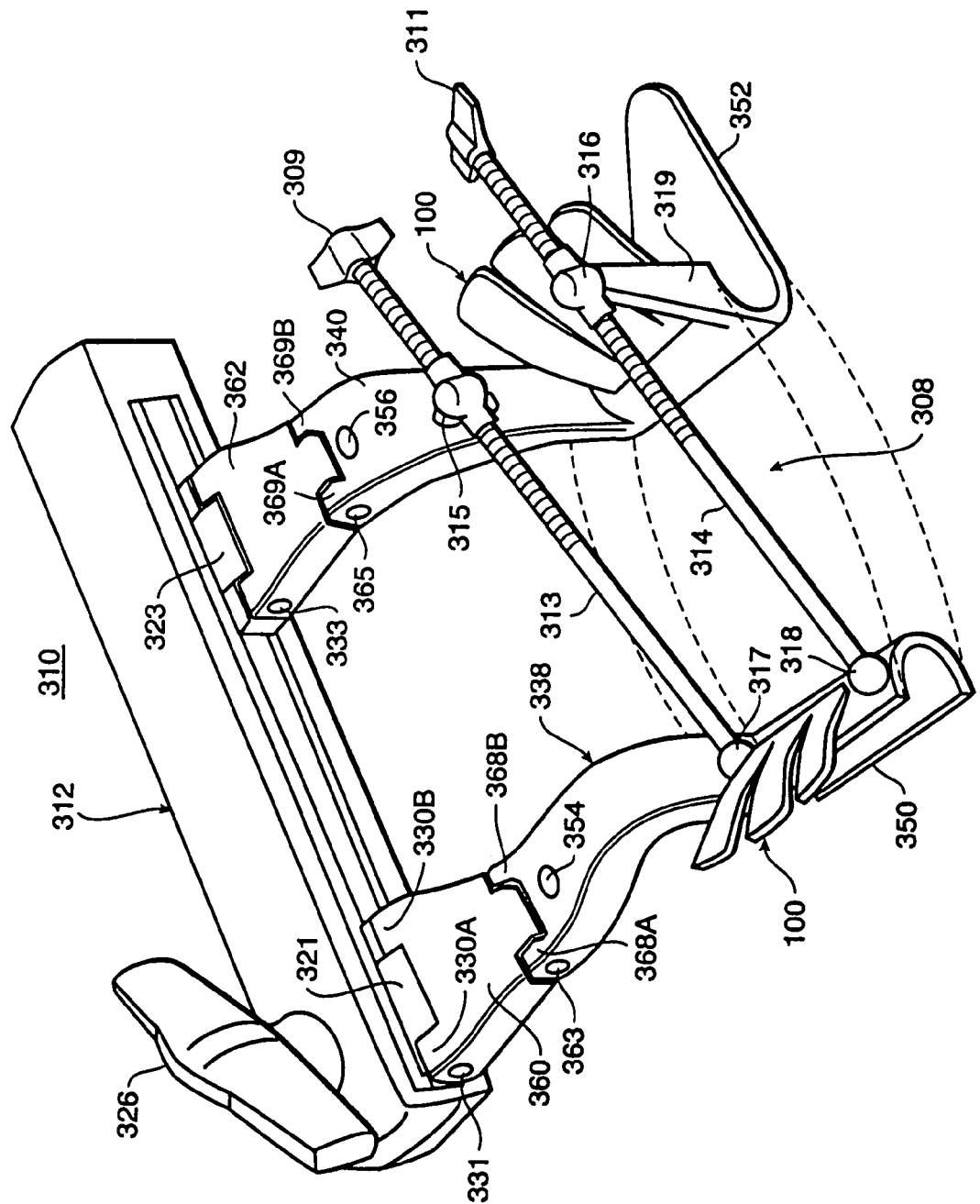
FIG. 23 is an isometric view of a seventh embodiment of the access platform of the present invention.

Turning to FIG. 23, a seventh embodiment of the access platform 310 is shown to comprise a modification of the fifth embodiment of the access platform 310 shown in FIG. 19. The access platform 310 in FIG. 23 includes an offset assembly 308 interconnected to the blades 350 and 352. The offset assembly 308 comprises lead screws 313 and 314 extending between the blades 350 and 352 and further operably interconnecting the blades 350 and 352. At a first end, the lead screws 313 and 314 are rotatably captured by capture mounts 317 and 318. The capture mounts 317 and 318 are fixed to the blade 350. The threaded portion of the lead screws 313 and 314 threadably passes through a pair of lift mounts 315 and 316. The lift mount 315 is affixed to the blade arm 340 which is interconnected to the superior blade 352. The lift mount 316 is affixed to the top of a lift mount arm 319 extending vertically from the superior blade 352 to a height which is level with the lift mount 315 on the blade arm 340. Levers 309 and 311, which are attached to a second end of the lead screws 313 and 314, are used to rotate the lead screws 313 and 314 to drive the lift mounts 315 and 316 thereon. With the horizontal distance between the inferior and superior blades 350 and 352 adjustably fixed by the spreader member 312, the offset assembly 308 is only able to vertically displace the blade 352 relative to the blade 350. Thus, depending on the direction of rotation of the lead screws 313 and 314, the superior blade 352 will be raised or lowered to offset it relative to the inferior blade 350.

Figure 24:
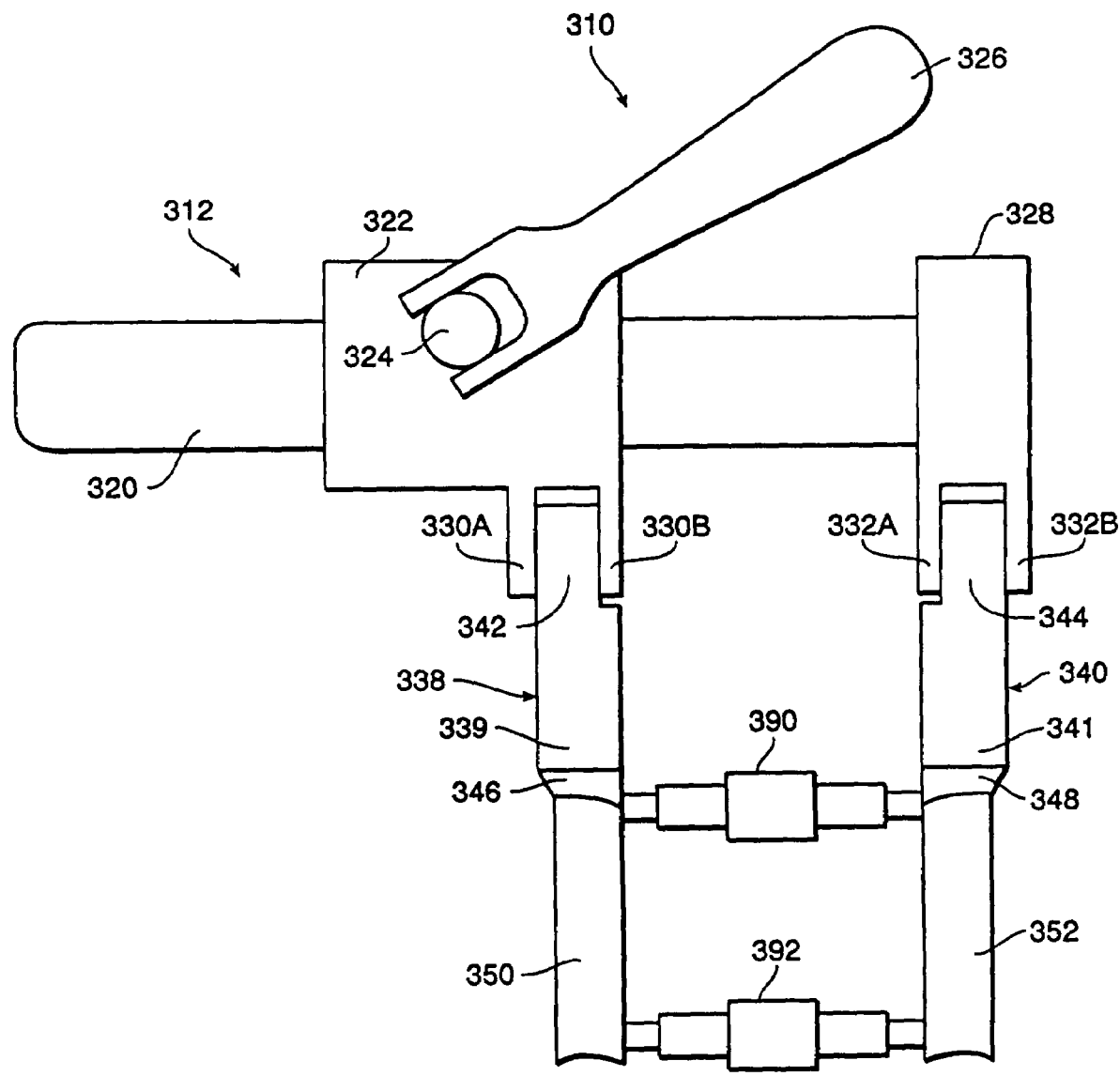
FIG. 24 is a top view of an eighth embodiment of the access platform of the present invention.
Figure 25:
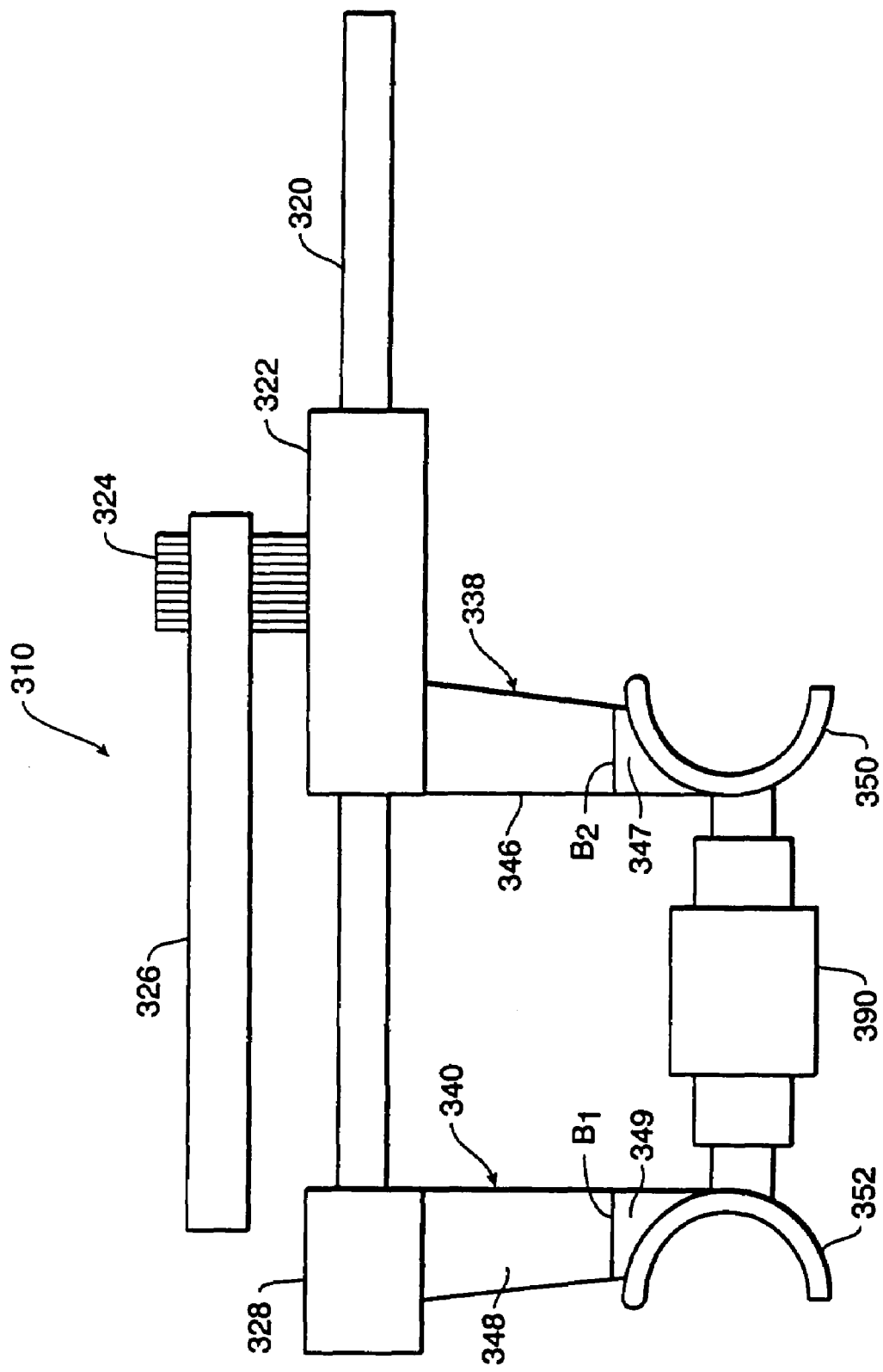
FIG. 25 is a rear view of the access platform in FIG. 24.

Referring to FIGS. 24 and 25, an eighth embodiment of the access platform 310 of the present invention includes telescoping arms 390 and 392 incorporated with the access platform 310 shown in FIG. 18. The telescoping arms 390 and 392 are perpendicularly disposed between and releasably attached to the blades 350 and 352. In addition, the blade arms 338 and 340 include branch extensions 347 and 349 releasably coupled at break lines $B_1$ and $B_2$ to the branches 346 and 348 (FIG. 25).

In operation, the blades 350 and 352 are inserted in an incision in the chest to capture the ribs. The lever 326 is then rotated to drive pinion 324 along the rack 320 and spread the ribs. Once the ribs are retracted to a desired spacing, the telescoping arms 390 and 392 are connected to the blades 350 and 352 and engaged to hold the blades 350 and 352 apart. The branches 346 and 348 are then decoupled from the branch extensions 347 and 349. The remainder of the access platform 310 can be moved away from the surgical site to give the surgeon additional space to work.

Also included with the fourth, fifth, sixth, seventh and eighth embodiments (FIGS. 18, 19, 22, 23 and 24-25, respectively) of the access platform 310, are ports or mounts (not shown) similar to the port 66 shown in FIG. 1 and similarly used to mount a heart stabilizer 67 (FIG. 1), an IMA holder, an IMA scope, a suture holder or other surgical instruments used in a "beating heart" CABG procedure. The surgical instrument mounting capability of the access platform 310 advantageously tends to eliminate the need for extra sets of hands around the surgical area.

Figure 26:
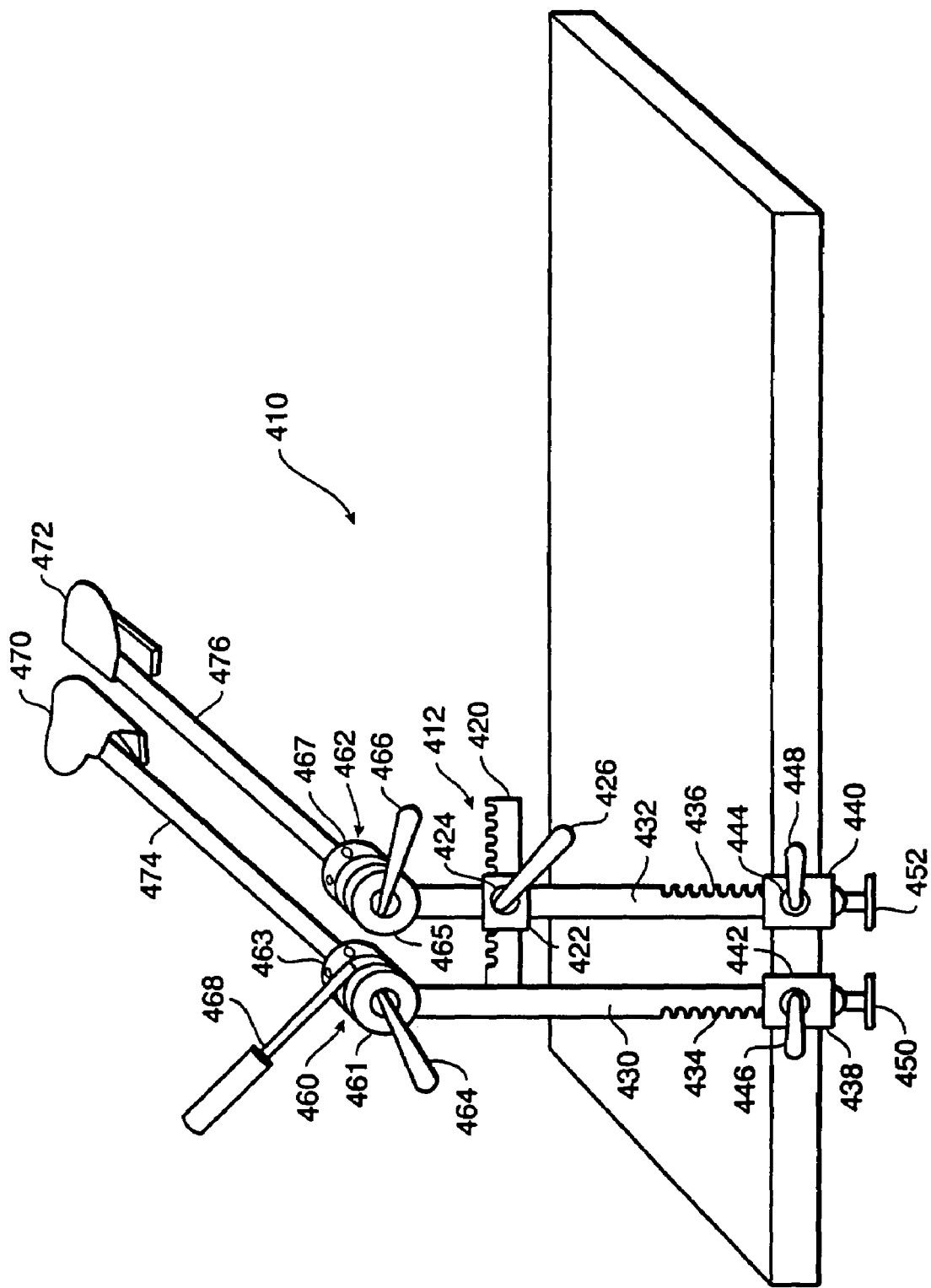
FIG. 26 is an isometric view of a ninth embodiment of the access platform of the present invention.

Turning to FIG. 26, a ninth embodiment of the access platform 410 of the present invention is shown. The access platform 410 mounts to the table or rail via slides 438 and 440 that are locked in place by positioners 450 and 452. The slides 438 and 440 rotatably retain pinions 442 and 444 driven by levers 446 and 448 and slidably receive stanchion racks 430 and 432. The stanchion racks 430 and 432 include rack gears 434 and 436 that operably couple with pinions 442 and 444. The levers 446 and 448 are rotated to drive the pinions 442 and 444 along rack gears 434 and 436 to adjust the height of the stanchion racks 430 and 432 relative to the table or patient, or to vertically offset blades 470 and 472 relative to one another.

A pinion housing 422 is slidably attached to the stanchion rack 432 towards its upper end. A rack 420 is attached at one end to stanchion rack 430 and is slidably received in the pinion housing 422. A pinion 424 driven by a lever 426 is rotatably retained in the pinion housing 422 and operably connected to the rack 420. The lever 426 is rotated to drive the pinion 424 along the rack 420 to spread apart the stanchion racks 430 and 432 and effectively a patient's ribs.

Torsional members 460 and 462 are attached to the top of the stanchion racks 430 and 432. Blade arms 474 and 476 extend outwardly from torsional members and attach to the blades 470 and 472. The torsional members comprise inner hubs 461 and 465 rotatably received in and operably connected to outer hubs 463 and 467. Locking levers 464 and 466 lock the inner hubs 461 and 465 in place relative to the outer hubs 463 and 467.

In operation, the access platform 410 is positioned such that the blades 470 and 472 can be inserted into an incision in a patient's chest and then attached to the blade arms 474 and 476. Once the blades 470 and 472 are positioned in the incision and attached to the blade arms 474 and 476, the lever 426 is rotated to spread the blades 470 and 472 and the patient's ribs apart. The blades 470 and 472 can be effectively offset by rotating the inner hubs 461 and 465 relative to the outer hubs 463 and 467. While the blades 470 and 472 are rotated, the stanchion racks 430 and 432 can be raised or lowered by rotating levers 486 and 488 to drive pinions 442 and 444. By raising or lowering the stanchion racks 430 and 432, the blades 470 and 472 can be effectively raised or lowered relative to one another to further offset the blades 470 and 472 relative to one another. A wrench 468 is utilized to rotate the inner hubs 461 and 465 relative to the outer hubs 463 and 467.

Figure 27:
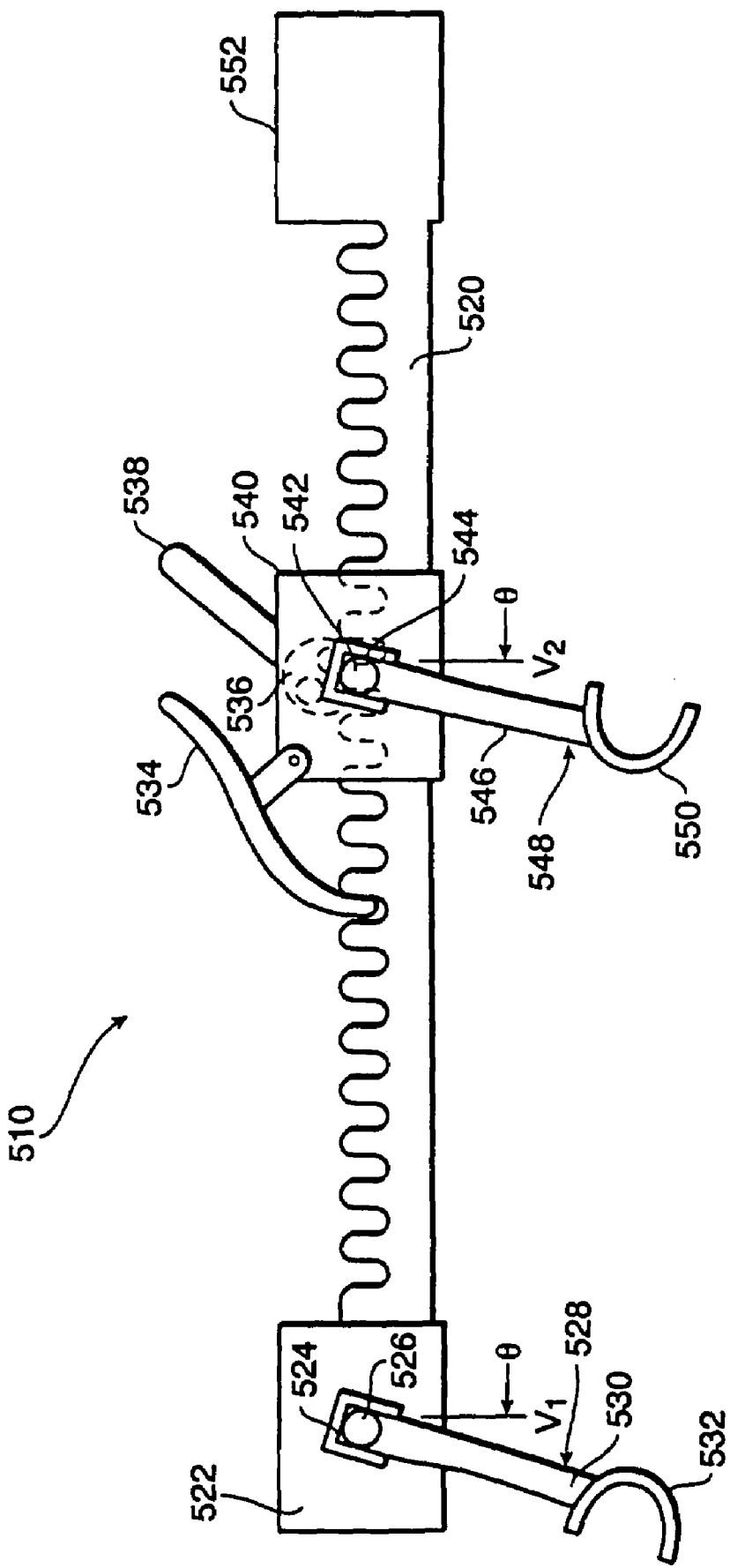
FIG. 27 is a front elevation view of a tenth embodiment of the access platform of the present invention.

Referring to FIG. 27, a tenth embodiment of the access platform 510 of the present invention is shown. The access platform 510 comprises a rack 520 attached at one end to a spreader base 522 and at the other end to a handle 552. A blade 532 is attached to a branch 530 of a blade arm 528. A stem 526 of the blade arm 528 extends from the branch 530 and is releasably received in a socket 524 formed in the spreader base 522. The branch 530 extends downwardly from the stem 526 at an angle Θ offset from the vertical $V_1$.

A pinion housing 540 is slidably received over the rack 520 and rotatably retains a pinion 536 driven by a lever 538. The pinion 536 is operably connected to the rack 520.

A blade 550 is attached to a branch 546 of a blade arm 548. A stem 542 of the blade arm 548 extends from the branch 546 and is releasably received in a socket 544 formed in the pinion housing 540. The branch 546 extends downwardly from the stem 542 at an angle (offset from the vertical $V_2$.

In operation, the blades 532 and 550 are inserted into an incision in the patient's chest and then the stems 526 and 542 of the blade arms 528 and 548 are inserted into the sockets 524 and 544. The lever 538 is rotated to drive the pinion 536 along the rack 520 until the blades 532 and 550 and the patient's ribs are positioned at a desired spacing. A spring loaded pawl 534 pivotally mounted to the housing 540 locks the housing 540 in place along the rack 520. The rack 520 is then lifted by the handle 552 to vertically displace or offset the blade 550 and the patient's ribs relative to the blade 532.

Figure 28:
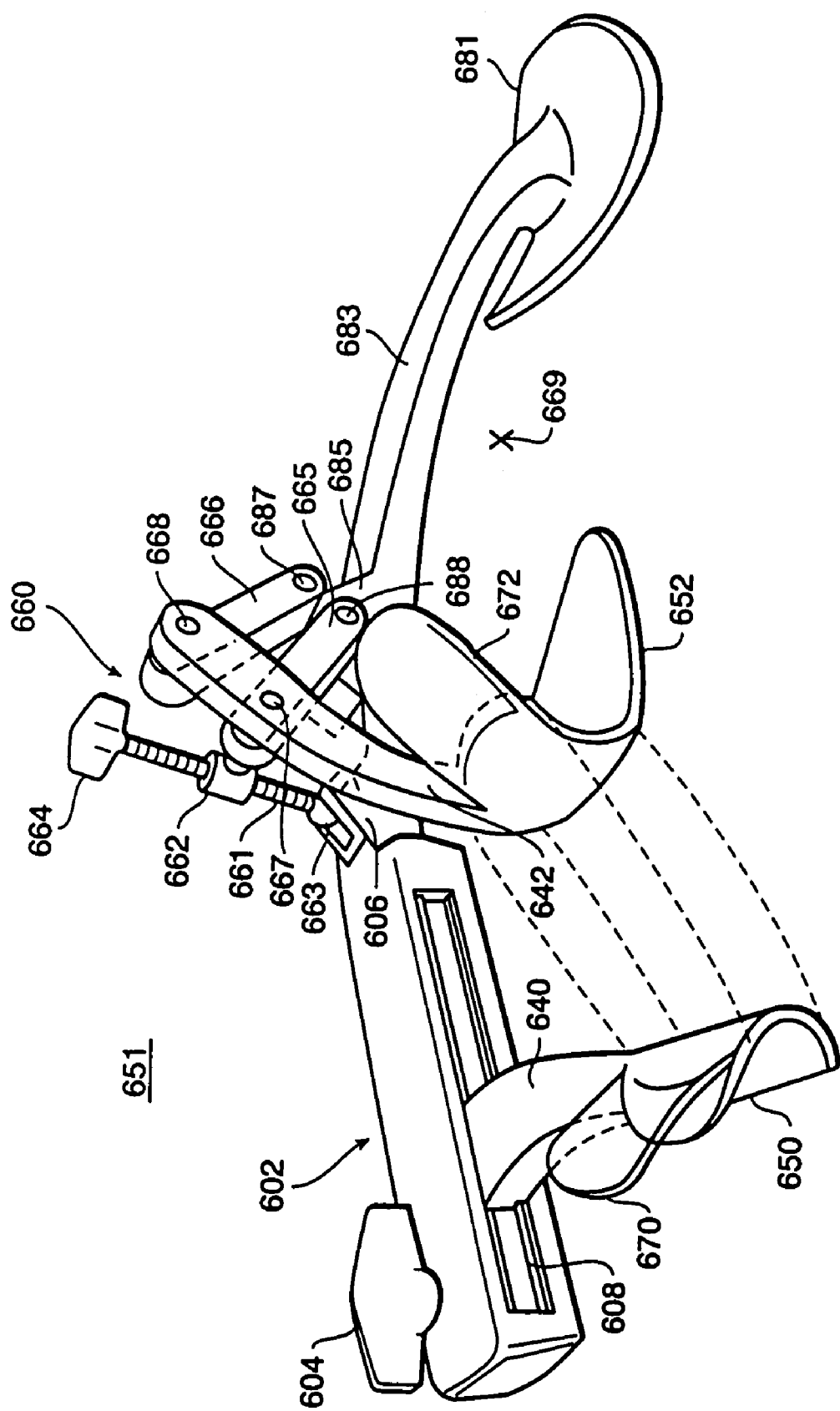
FIG. 28 is an isometric view of an eleventh embodiment of the access platform of the present invention.

Turning to FIG. 28, an eleventh embodiment of the access platform 651 comprises a spreader housing 602 that includes a drive mechanism therein (not shown) and a drive slot 608 formed therein. A spreader lever 604 is mounted on top of the spreader housing 602 and is operably connected to the drive mechanism housed therein. An inferior blade 650 is interconnected to the drive mechanism via a blade arm 640 which extends outwardly to the inferior blade 650 from the spreader housing 602 in a direction generally normal to the housing 602. A tissue retractor 670 is attached to the blade 650 to assist in tissue retraction.

A pad arm 683 is formed integrally with the spreader housing 602 and extends longitudinally to a sternal pad 681. The pad arm 683 is generally arcuately shaped to conform to an extended rib cage due to the offset of the patient's ribs.

A superior blade 652 having a tissue retractor 672 extending therefrom is connected to the bottom end of a blade arm 642. The top end of the blade arm 642 is pivotally connected to an offset drive assembly 660. The offset drive assembly 660 comprises a guide link 666 and a drive link 665 which are pivotally connected at pivots 687 and 688 to a mount 685 extending upwardly from the pad arm 683 and at pivots 668 and 667 to the blade arm 642. The drive link 665 is also pivotally connected to a drive carrier 662 which threadably captures a lead screw 661 and is traversely driven along the lead screw 661 as the lead screw 661 is rotated. A lever 664 is attached to the top of the lead screw 661 to rotate the lead screw 661. The base of the lead screw 661 is rotatably captured in a bushing 663 which is rotatably captured in a drive mount 606 extending up from the spreader housing 602.

In operation, the inferior and superior blades 650 and 652 are inserted in an incision in the patient's chest capturing the inferior and superior ribs adjacent to the incision. The pad arm 683 is sufficiently long to position the sternal pad 681 adjacent the patient's upper sternal-costal area. After the blades 650 and 652 and sternal pad 681 are properly positioned, the spreader lever 604 is rotated to transversely drive the blade arm 640 connected to the inferior blade 650 along the drive slot 608 to separate the inferior and superior blades 650 and 652. Once the inferior and superior blades 650 and 652 are separated to a desired spacing, the offset assembly 660 is activated to lift the superior blade 652. As the offset lever 664 is rotated in an appropriate direction, the drive carrier 662 will be driven along the lead screw 661. As the drive carrier 662 rises along the lead screw 661, the drive link 665 and guide link 666 pivot in a clockwise rotation about pivots 687 and 688 causing the superior blade 652 to rotate about a remote center of rotation shown at 669. As the superior blade 652 is rotated about the remote center of rotation 669, the pad arm 683 and sternal pad 681 apply the necessary torque against the patient's upper sternal-costal area to maintain the lift on the superior ribs.

In the offset position, with the superior blade 652 maintaining a lift of the superior ribs and the tissue retractors 670 and 672 engaged, a surgeon can dissect the IMA. With the dissection of the IMA complete, the surgeon substantially levels the inferior and superior blades 650 and 652 by reverse rotating the lead screw 661. In the substantially level separated position, the surgeon can perform an arteriotomy and an anastomosis. After completion of these procedures, the surgeon disengages the soft tissue retractor 670 and 672 and brings the blades 650 and 652 together by reverse rotation of the lever 604. The blades 650 and 652 can then be removed from the interior of the patient's chest. With the blades 650 and 652 removed, the surgeon is able to close the thoracotomy to complete the surgical procedure.

Figure 29:
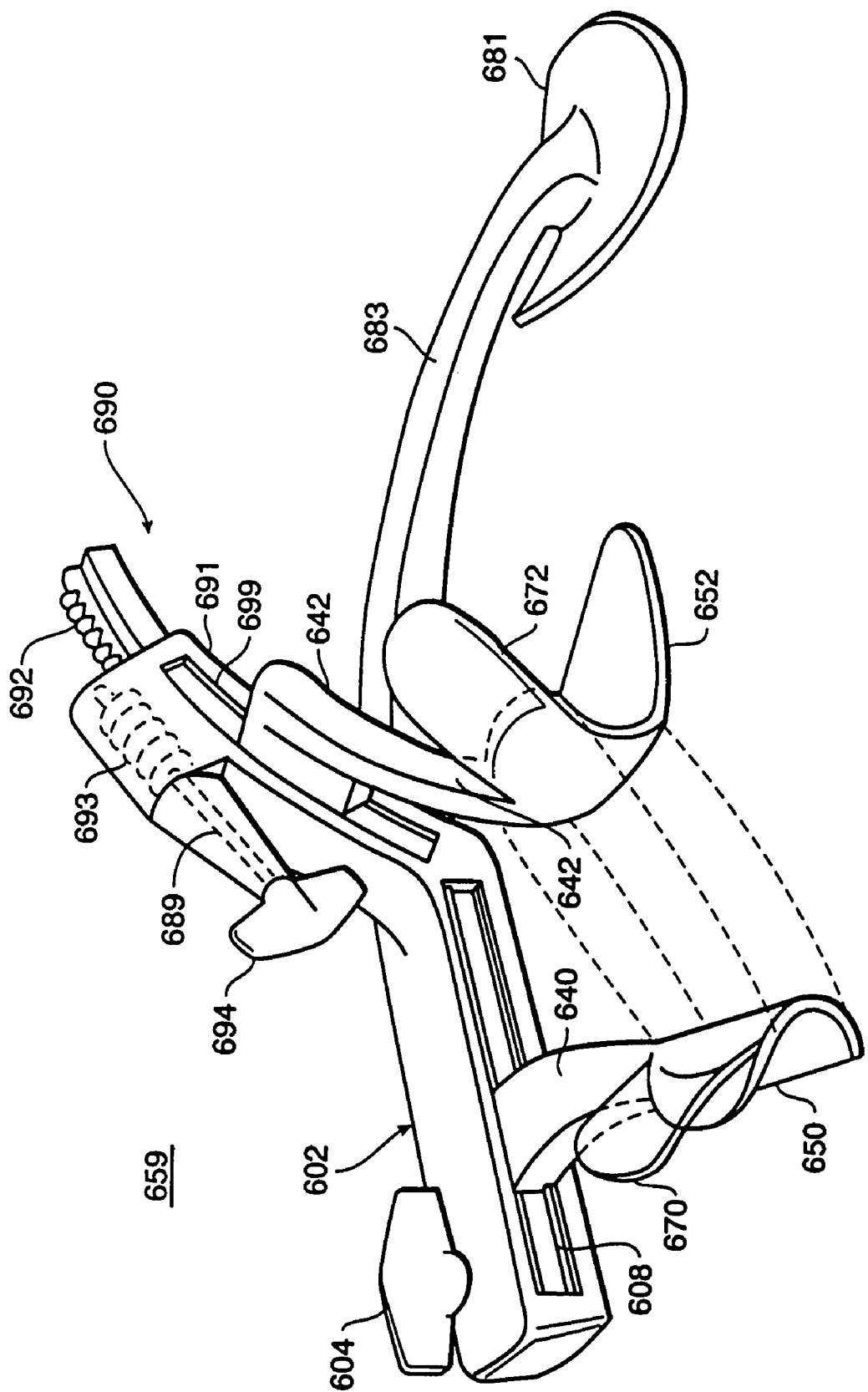
FIG. 29 is an isometric view of a twelfth embodiment of the access platform of the present invention.

Referring to FIG. 29, a twelfth embodiment of an access platform 659 is shown to comprise a modification of the eleventh embodiment of the access platform 651 shown in FIG. 28. The offset assembly 690 of the access platform includes an offset housing 691 extending upwardly from the spreader housing 602 and adapted to slidably receive a curved rack 692. The blade arm 642 is attached to the curved rack 692 through a slot 699 in the housing 691. A worm gear 693 is positioned within the housing 691 and is operably connected to the curved rack 692. A worm gear shaft 689 extends from the worm gear 693 and connects to a lever 694 outside of the housing 691. Thus, to lift the superior blade 652 and ribs, the lever 694 is rotated in an appropriate direction to rotate the worm gear 693 to drive the curved rack 692 upwardly and outwardly from the housing 691. To lower the superior blade 652 from the offset position, the lever 694 is reverse rotated to drive the curved rack 692 in an opposite direction.

Figure 30:
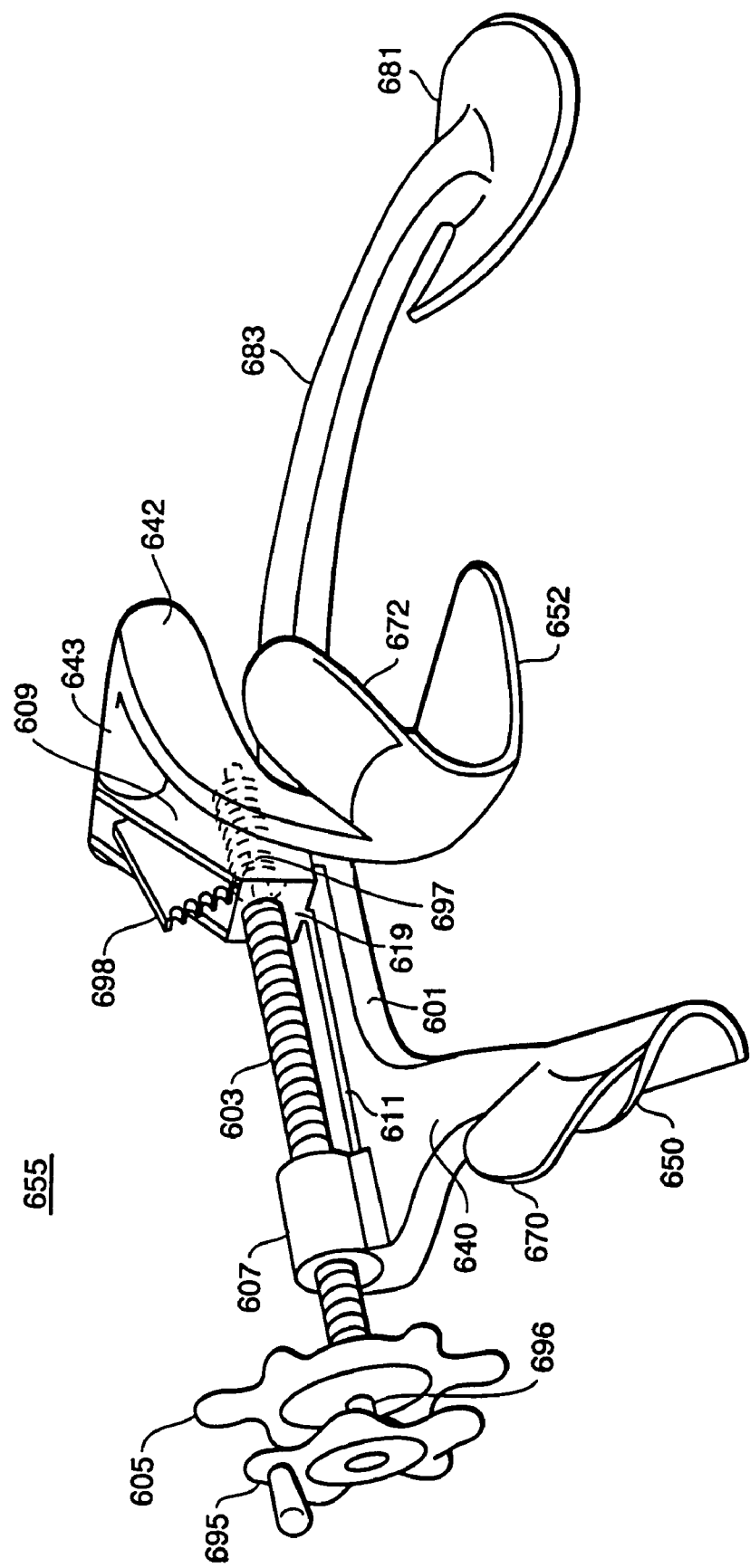
FIG. 30 is an isometric view of a thirteenth embodiment of the access platform of the present invention.

Turning to FIG. 30, a thirteenth embodiment of the access platform 655 of the present invention comprises a generally elongated drive base 601 having a blade arm 640 and a pad arm 683 extending therefrom. The blade arm 640 extends in a generally normal direction from the drive base 601, while the pad arm 683, which is generally arcuately shaped, extends longitudinally and downwardly from the drive base 601. The pad arm 683 terminates in a sternal pad 681. A threaded shaft carrier 607 extends upwardly from the drive base 601 adjacent the blade arm 640. An inferior blade 650 having a tissue retractor 670 extending therefrom attaches to the blade arm 640. In a preferred construction, the inferior blade 650, tissue retractor 670, blade arm 640, threaded shaft carrier 607, drive base 601, pad arm 683, and sternal pad 681 are formed from one-piece construction.

A hollow threaded shaft 603 is threaded through the shaft carrier 607 and extends along the drive base 601 to rotatably attach to a hollow drive block 609. A spreader handle 605 is attached to the shaft 603 at an end opposite the drive block 609. A worm gear 697 positioned in the drive block 609, is fixed to the end of a shaft 696 that passes through the hollow threaded shaft 603 and attaches to an offset handle 695 beyond the spreader handle 605. The worm gear 697 is operably connected to an arcuate worm gear rack 698 that is positioned within the drive block 609 and connected to a branch 643 of a blade arm 642. The branch 643 of the blade arm 642 extends from the blade arm 642 in a normal direction and is pivotally mounted to the hollow drive block 609. The blade arm 642 extends downwardly from the branch 643 and attaches to a superior blade 652 with a tissue retractor 672 extending therefrom. A follower 619 extends downwardly from the base of the hollow drive block 609 and is received in a elongated drive slot 611 in the drive base 601. As the drive block 609 is transversely driven along the base 601 by the threaded shaft 603, the follower 609 slidably follows the drive slot 611 in the drive base 601.

In operation, the blades 650 and 652 are inserted into an incision in the patient's chest while the sternal pad 681 is positioned adjacent the patient's upper sternal-costal area. After the blades 650 and 652 and sternal pad are properly positioned, the spreader handle 605 is rotated in an appropriate direction to longitudinally and rotatably drive the threaded shaft 603 through the shaft carrier 607 and thereby traversely drive the drive block 609 along the drive base 601 until the separation between the blades 650 and 652 reaches a desired spacing. To offset the blades 650 and 652, the offset handle 695 is rotated in an appropriate direction to rotate the worm gear 697 and drive the worm gear rack 698 in a clockwise direction. The rotation of the worm gear rack 698 in a clockwise direction pivots the superior blade 652 about the branch 643 of the blade arm 642 in a clockwise rotation. By rotating the superior blade 652 in a clockwise rotation, the superior ribs captured by the superior blade 652 are lifted and a torque necessary to maintain the lift of the ribs is applied to the patient's upper sternal-costal area through the sternal pad 681.

By rotating the spreader and offset handles 605 and 695 simultaneously in an appropriate direction, the lifting of the superior ribs is advantageously achieved while simultaneously spreading the blades 650 and 652 or maintaining the already retracted spacing between the blades 650 and 652 and corresponding ribs. More particularly in regard to maintaining the retracted spacing, by rotating the spreader handle 605 simultaneously with the offset handle 695, the drive block 609 is traversely driven along the drive base 601 to compensate for the rearward lateral component of the superior blade's 652 motion as it travels upward in a clockwise arc.

With the superior blade 652 and ribs raised in an offset position, the surgeon can dissect the IMA. After completion of the dissection of the IMA, the surgeon can substantially level the blades 650 and 652 by reverse rotating both the offset handle 695 and the spreader handle 605 together. With the blades 650 and 652 in a level and separated position, the surgeon can perform an arteriotomy and an anastomosis. After the completion of these surgical procedures, the surgeon disengages the soft tissue retractors 670 and 672 and brings the blades 650 and 652 together by reverse rotating the spreader handle 605. The blades 650 and 652 are then removed from the interior of the patient's chest and the thoracotomy is closed to complete the surgical procedure.

Figure 31:
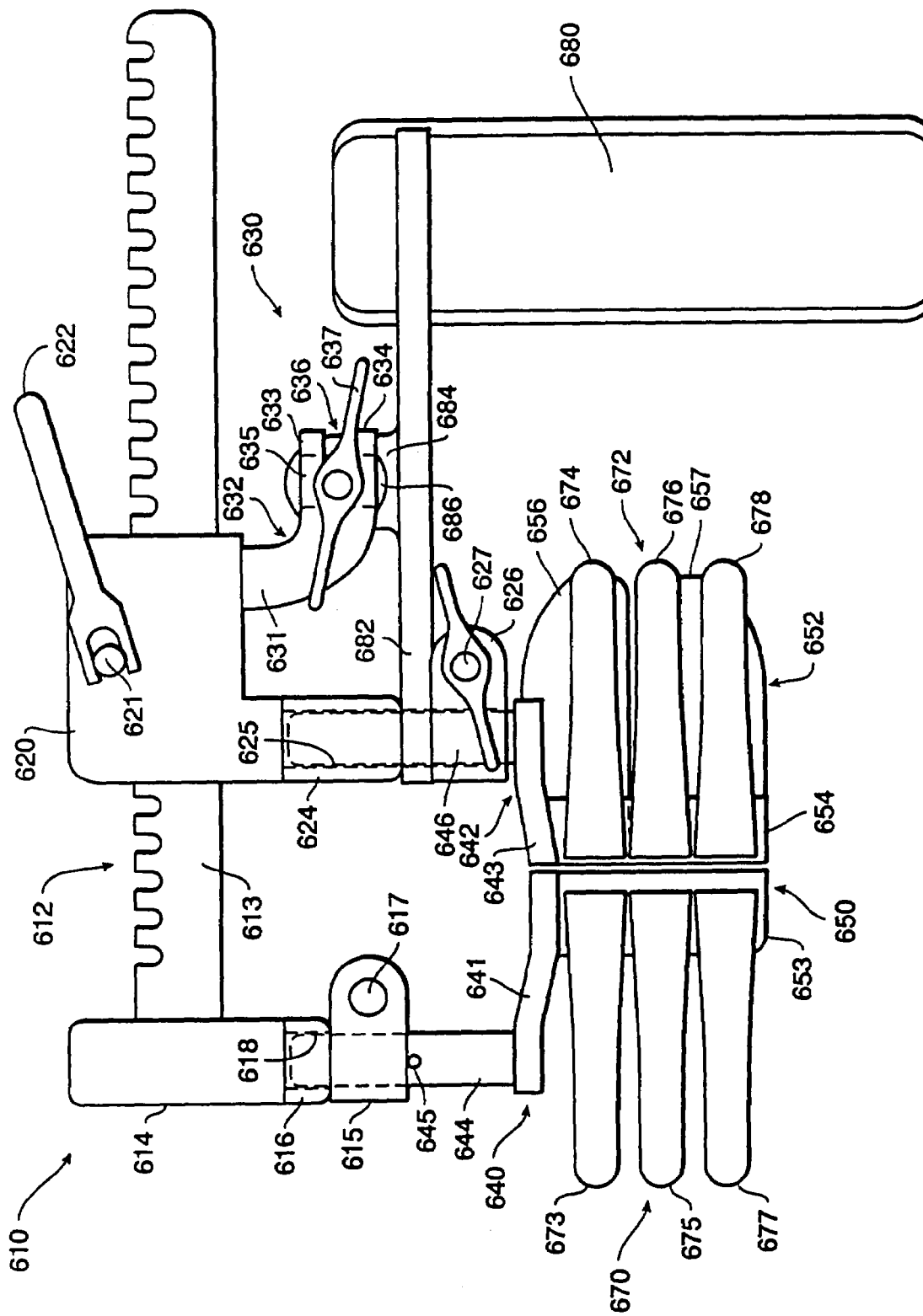
FIG. 31 is a top view of a fourteenth embodiment of the access platform of the present invention.
Figure 32:
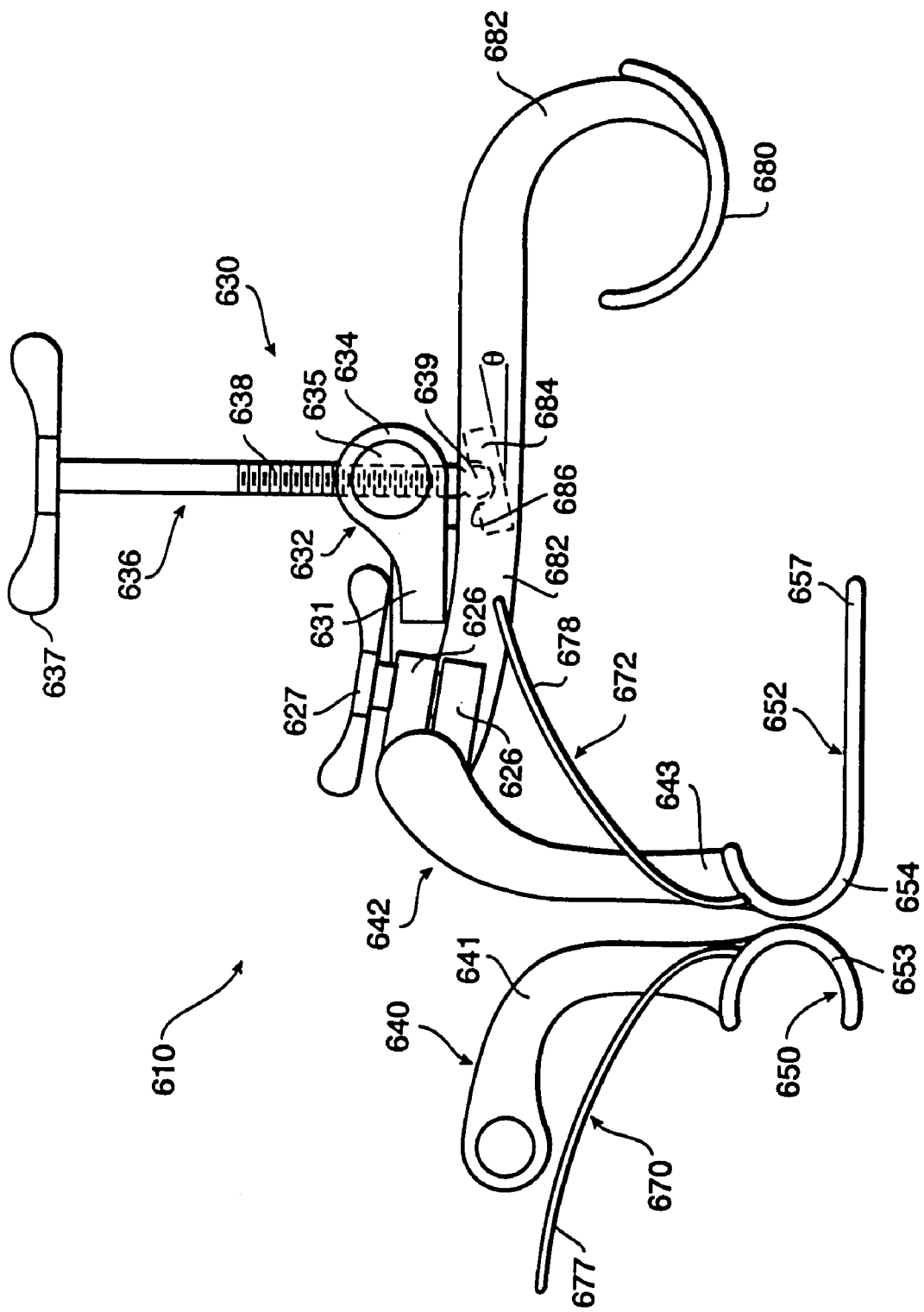
FIG. 32 is a partial front elevation view of the access platform in FIG. 31.

Referring to FIGS. 31 and 32, a fourteenth embodiment of the access platform 610 of the present invention comprises a spreader component 612 that includes a rack 613, a spreader base 614 attached to one end of the rack 613 and a pinion housing 620 slidably received over the rack 613. A pinion 621 that is driven by a lever 622 is rotatably retained in the pinion housing 620 and operably connected to the rack 613.

A fixed pivot 616 having a socket 618 formed therein, extends from the spreader base 614. A fixed pivot lock 615 with a lock screw 617 is fixedly connected to the fixed pivot 616. A moveable pivot 624 having a socket 625 formed therein, extends from the housing 620. Rotatably and releasably received in and extending from the sockets 618 and 625 are stem portions 644 and 646 of a pair of blade arms 640 and 642, respectively. The stem 644 that is received in the socket 618 of the fixed pivot 616 includes a stop 645 formed on its exterior to abut the fixed pivot lock 615 and stop the travel of the stem 644. Branch portions 641 and 643 of the blade arms 640 and 642 extend downwardly from the stem portions 644 and 646 and attach to inferior and superior blades 650 and 652, respectively. The superior blade 652 which is advantageously located below and interconnected to the moveable pivot 624, comprises a recessed throat 654 to capture a rib adjacent to an incision in the patient's chest cavity and a pair of elongated vanes 656 and 657 used to offset a plurality of the patient's ribs. The inferior blade 650 which is interconnected to the fixed pivot 616 comprises a recessed throat 653 used to capture a rib adjacent to an incision in the patient's chest cavity.

Tissue retractors 670 and 672 are attached to the blades. The retractors 670 and 672 include a plurality of retractor fingers 673, 675 and 677, and 674, 676 and 678, respectively, extending upwardly from the throat sections 653 and 654 of the blades 650 and 652. The retractors 670 and 672 are preferably constructed from annealed sheet metal approximately 0.035 inch thick and are preferably welded onto the blades 650 and 652.

The branch portion 643 of the blade arm 642 that is interconnected to the moveable pivot 624 extends higher vertically than the branch portion 641 of the blade arm 640 that is interconnected to the fixed pivot 616 when the blades 650 and 652 are substantially level (see FIG. 29). This construction tends to increase the moment about the moveable pivot 624 caused by the offset of the movable pivot from the center-of-effort of the spreading force at the blades 650 and 652. Because the movable pivot 624 is located above the superior blade 652, a lifting force is naturally exerted on the superior blade 652 and ribs as spreading occurs.

To add additional offset of the superior blade 652 once the blades 650 and 652 are separated and offset, a vertical displacement component 630 is included on the access platform 610. The vertical displacement component 630 comprises a rib compression shoe 680, a substantially "S" shaped shoe arm 682 connected to the shoe 680 at one end and pivotally connected to the stem 646 of the blade arm 642 at the other end, and an adjustable offset link 632 connected to the pinion housing 620 and operably connected to the shoe arm 682 and shoe 680. The shoe 680 has an arcuate front profile and a rectangular top profile. A moveable pivot lock 626 with a lock screw 627 is fixedly mounted to the end of the shoe arm 682. The movable pivot lock 626 fixes the shoe arm 682 relative to the blade arm 642.

The offset link 632 comprises a substantially "L" shaped base 631 that extends from the pinion housing 620 at one end and terminates at the other end in a pair of parallel spaced and arcuate shaped fingers 633 and 634. A bushing 635 having a hole tapped through its center perpendicular to the bushing's 635 longitudinal axis, is rotatably captured by the fingers 633 and 634. An adjustable offset drive screw 636 is threaded through the hole in the bushing 635 and is operably connected to the shoe arm 682.

The adjustable offset drive screw 636 comprises a handle 637 attached to the top end of a jack screw 638. The base of the jack screw 638 is formed as a hemisphere 639. The hemisphere 639 operably couples with a hemispherical recess 686 cut into a boss 684 that extends outwardly from the shoe arm 682. The boss 684 is tilted upwardly at an angle Θ relative to the longitudinal axis of the shoe arm 682. This construction ensures that the hemisphere 639 will maintain contact with the boss 684 during operation as the jack screw 638 forces the shoe arm 682 and shoe 680 to rotate downwardly in a clockwise direction.

In addition, the access platform 610 includes mounts (not shown) attached to the blade arms 640 and 642. The mounts enable the access platform 610 to hold a heart stabilizer tool 67 shown in FIG. 1, an IMA holder, an IMA scope, a suture holder, or other surgical instruments used in a "beating heart" CABG procedure. Thus, the mounts advantageously eliminate the need for an undesirable extra set of hands around the surgical site.

In operation, the blades 650 and 652 are inserted in an incision in the patient's chest such that the elongated vanes 656 and 657 of the blade 652 are positioned under the patient's ribs while the recessed throats 653 and 654 of the blades 650 and 652 are positioned to receive the ribs that are adjacent to the incision. After the blades 650 and 652 are properly positioned, the stem 644 of the blade arm 640 is inserted through the fixed pivot lock 615 into the socket 618 of the fixed pivot 616. Meanwhile, the stem 646 of the blade arm 642 is inserted through the moveable pivot lock 626 and the end of the shoe arm 682 opposite the shoe 680, and into the socket 625 of the moveable pivot 624. The blade 650 is then fixed in position by tightening the fixed pivot lock screw 617 to tighten the fixed pivot lock 615 around the stem 644 of the blade arm 640.

The rib compression shoe 680 is then adjusted downwardly by adjusting the adjustable offset drive screw 636 until the desired compression of the ribs is achieved. The blade 652 that is interconnected to the moveable pivot 624 is then fixed in position relative to the shoe 680 by tightening the moveable pivot lock screw 627 to tighten the moveable pivot lock 626 around the stem 646 of the blade arm 642. The ribs are then separated and simultaneously offset by rotating the lever 622 to drive the pinion 621 along the rack 613 until a desired opening width is realized. Because the movable pivot 624 is advantageously located above the blade 652, the superior blade 652 naturally raises vertically as it rotates about the moveable pivot 624 as a spreading force from the inferior blade 650 is transmitted to the superior blade 652 through the movable pivot 624.

Further adjustment of an offset height of the superior blades 652 may be obtained by first loosening the moveable pivot lock 626 around the stem 646 of the blade arm 642 and then adjusting the adjustable offset drive screw 636 to cause the shoe 680 and the shoe arm 682 to rotate downwardly in a clockwise direction relative to the superior blade 652 and, thus, cause the blade 652 that is interconnected to the moveable pivot 624 to rise vertically until a desired offset is achieved. Alternatively, the blade arm 642 would remain fixed to the shoe arm 682 as the offset drive screw 636 is adjusted to cause the shoe 680 and shoe arm 682 to rotate downwardly in a clockwise direction. The clockwise rotation of the shoe 680 and shoe arm 682 causes the blade 652 to rotate upwardly in a clockwise direction.

After the ribs have been retracted and vertically displaced, the tissue retractors 670 and 672 are operated to retract the soft tissue away from the incision area by bending fingers 673, 675, and 677, and 674, 676, 678 over the patient's chest. By bending the retractor fingers 673, 674, 675, 676, 677 and 678 over the patient's chest, the fingers 673, 674, 675, 676, 677 and 678 advantageously press down against the soft tissue to retract it away from the incision and out of the surgeon's working area.

In the offset position, with the superior blade 652 raising the patient's ribs, the surgeon can dissect the IMA. With the dissection of the IMA complete, the surgeon substantially levels the blades 650 and 652 by reverse rotating the adjustable offset drive screw 636 and then either removes the access platform 610 completely or engages a heart stabilizer 67 as shown in FIG. 1. With the heart stabilizer 67 engaged to minimize the movement of the heart, the surgeon performs an arteriotomy and anastomosis. After completion of the arteriotomy and anastomosis, the surgeon removes the stabilizer 67, disengages the soft tissue retractors 670 and 672 and brings the blades 650 and 652 together. The blades 650 and 652 are then disengaged from the access platform 610 and then removed from the interior of the patient's chest. With the blades 650 and 652 removed, the surgeon is able to close the thoracotomy to complete the surgical procedure.

Figure 33:
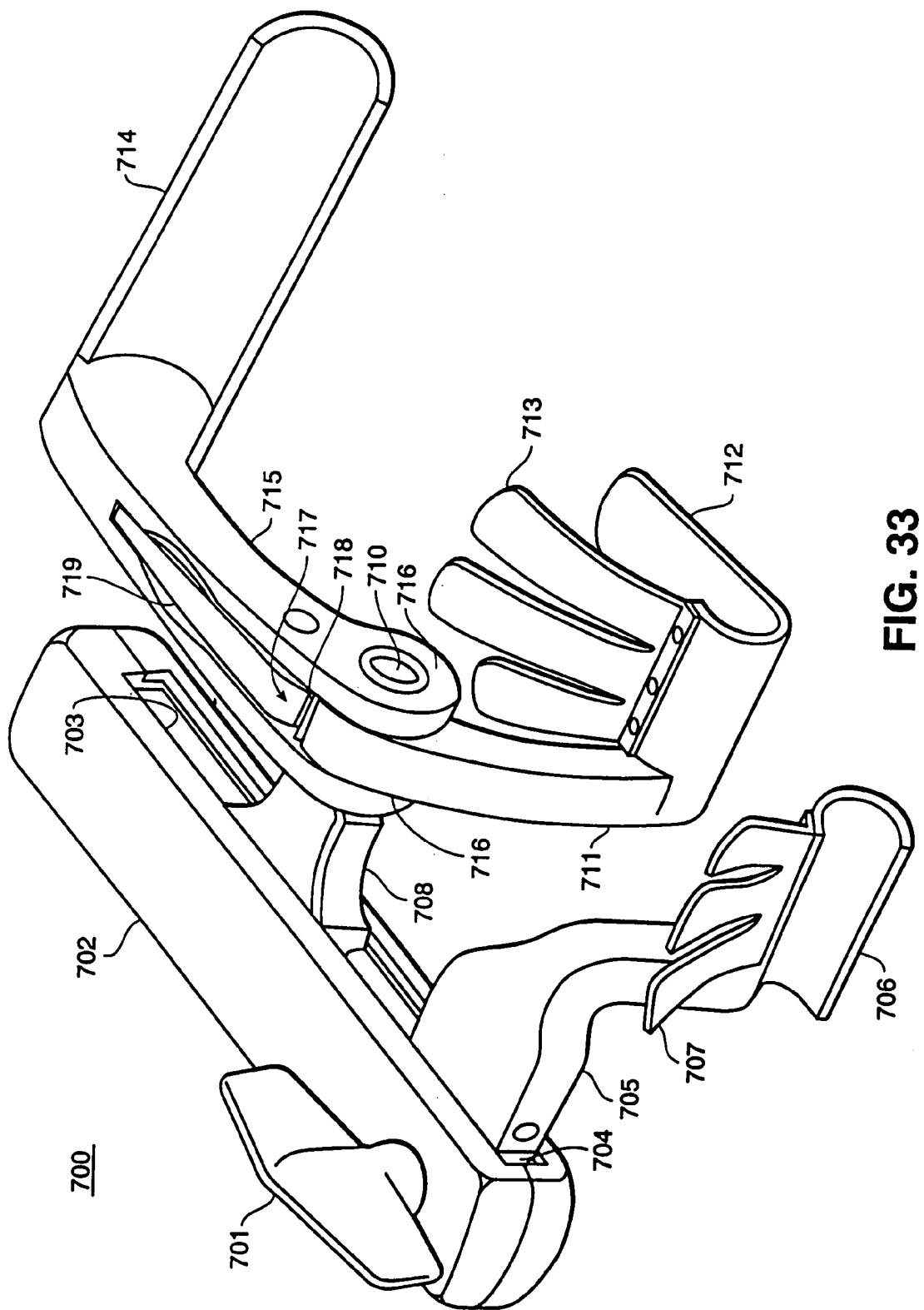
FIG. 33 is an isometric view of a fifteenth embodiment of the access platform of the present invention.
Figure 34:
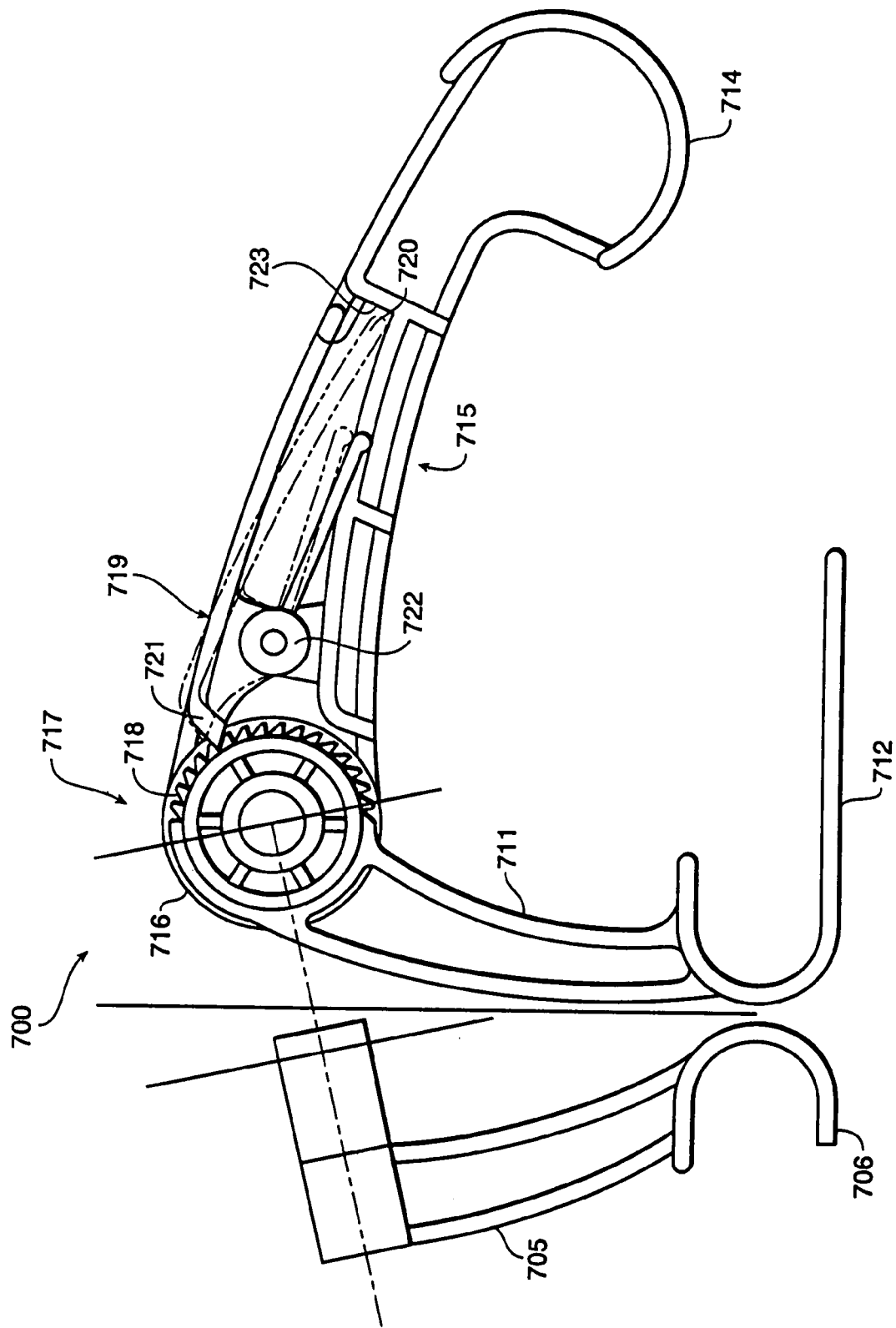
FIG. 34 is a partial front elevation view of the access platform in FIG. 33.
Figure 35:
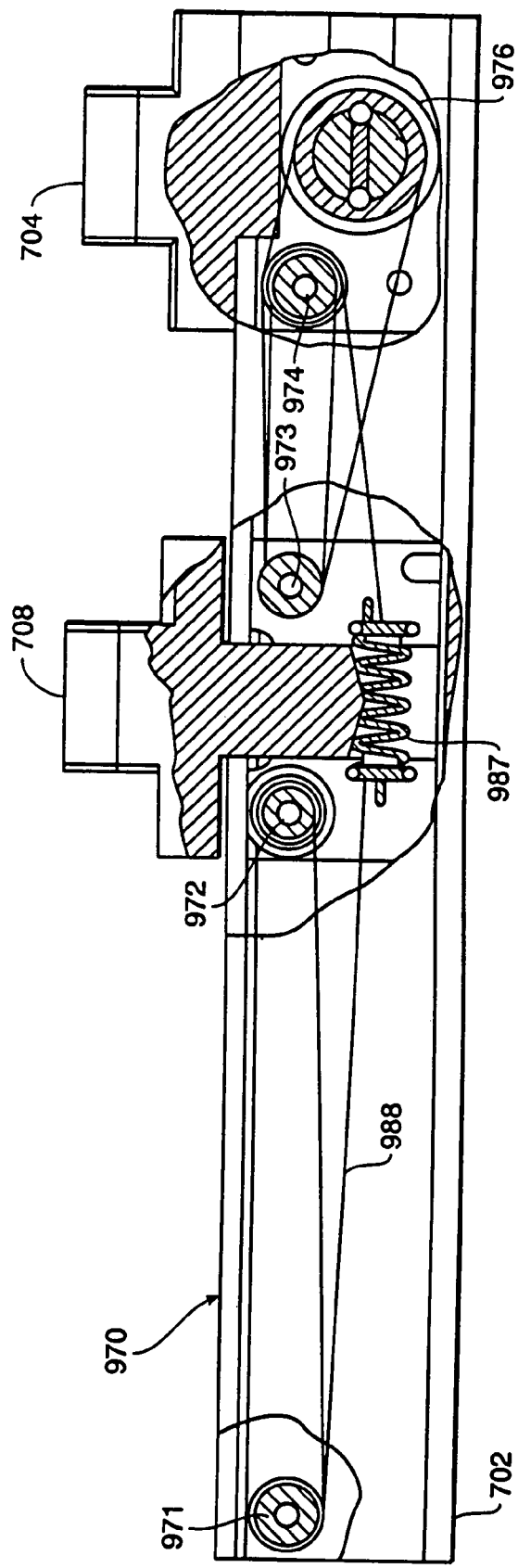
FIG. 35 is a top view of a spreader member drive assembly of the access platform in FIG. 33.

A fifteenth embodiment of an access platform 700 of the present invention, as shown in FIGS. 33 and 34, comprises an elongated spreader housing 702 with a block and tackle type drive mechanism 970 located therein (see FIGS. 35-38 discussed in detail below). A lever 701 interconnected to the drive mechanism 970 extends upwardly from the spreader housing 702. A blade arm 705 connected to an inferior blade 706 is mounted to a base 704 fixedly received in the housing 702. The blade arm 705 extends outwardly and then downwardly from the spreader housing 702 to the inferior blade 706. The inferior blade 706 includes a tissue retractor 707 extending therefrom.

A drive block 708 coupled to the drive mechanism 970 in the spreader housing 702, extends outwardly from the spreader housing 702 in a normal direction to the housing 702. As the lever 701 is rotated, the drive mechanism 970 slidably carries the drive block 708 along the drive slot 703 of the spreader housing 702.

A blade arm 711 is attached at its lower end to a superior blade 712 with a tissue retractor 713 extending therefrom. At its upper end, the blade arm 711 is rotatably coupled to an upper end of an elongated arcuate pad arm 715. The pad arm 715 is attached at its lower end to a sternal pad 714. The upper end of the pad arm 715 forms a forked hub 716. The blade arm 711, pad arm 715 and sternal pad 714 assembly is releasably and rotatably mounted on a cylindrical shaft 710 attached to the drive block 708.

The access platform 700 incorporates an offset positioning assembly 717 that comprises a pawl 719 pivotally mounted in a recess 723 of the pad arm 715 at a pivot 722 and a ratchet 718 formed on the upper end of the blade arm 711. The pawl 719 includes a pawl nose 721 that engages the ratchet 718 and a pawl lever 720 that is depressed to pivot the pawl 719 about pivot 722 to disengage the pawl nose 721 from the ratchet 718. With the pawl nose 721 engaged, the pad arm 715 can only rotate in a clockwise direction relative to the blade arm 711. The pawl 719 prevents the hub 716 of the arm 715 from rotating in a counterclockwise direction relative to the blade arm 711. With the pawl nose 721 disengaged from the ratchet 718, the pad arm 715 can freely rotate relative to the blade arm 711 in a counterclockwise direction.

In operation, with the superior blade 712 and sternal pad 714 assembly separated from the rest of the access platform 700, the superior blade 712 and sternal pad 714 assembly is positioned on the patient's chest. Initially the angle between the blade and pad arms 711 and 715 is large or nearly flat. The superior blade 712 is then inserted into an incision in the patient's chest wall and slid under the superior ribs adjacent to the incision. With the superior blade 712 properly positioned within the incision, the sternal pad 714 is adjusted downwardly on top of the patient's chest wall by rotating the pad arm 715 relative to the blade arm 711 in a clockwise direction to decrease the angle between the pad arm 715 and blade arm 711.

Next, the rest of the access platform 700 with the inferior blade 706 attached, is aligned on the patient's chest. The inferior blade 706 is then inserted into the incision in the patient's chest. The blade arm 711 and pad arm 715 assembly is then rotatably mounted on the shaft 710. The access platform 700 is now fully assembled and the blades 706 and 712 are in parallel alignment.

The handle 701 is rotated to spread the blades 706 and 712. Because the shaft 710 is located above the superior blade 712 and because the superior blade 712 and sternal pad 714 assembly pivots freely around the shaft 710 a lifting of the superior blade 712 and ribs naturally occurs as the blades 706 and 712 are separated. The spreading force from the inferior blade 706 is transmitted to the superior blade 712 through the shaft 710 located above the superior blade 712. With the blades 706 and 712 offset, the surgeon can harvest the IMA. Upon completion of the IMA harvest, the handle 701 is rotated in a reverse direction to bring the blades fully together. With the blades 706 and 712 together, there is substantially no spreading force being exerted on the superior blade 712 and sternal pad 715 assembly. The pawl lever 720 can then be depressed to disengage the pawl nose 721 from the ratchet 718. With the pawl 719 disengaged, the sternal pad 714 and pad arm 715 are raised allowing removal of the access platform 700 from the incision.

Figure 39:
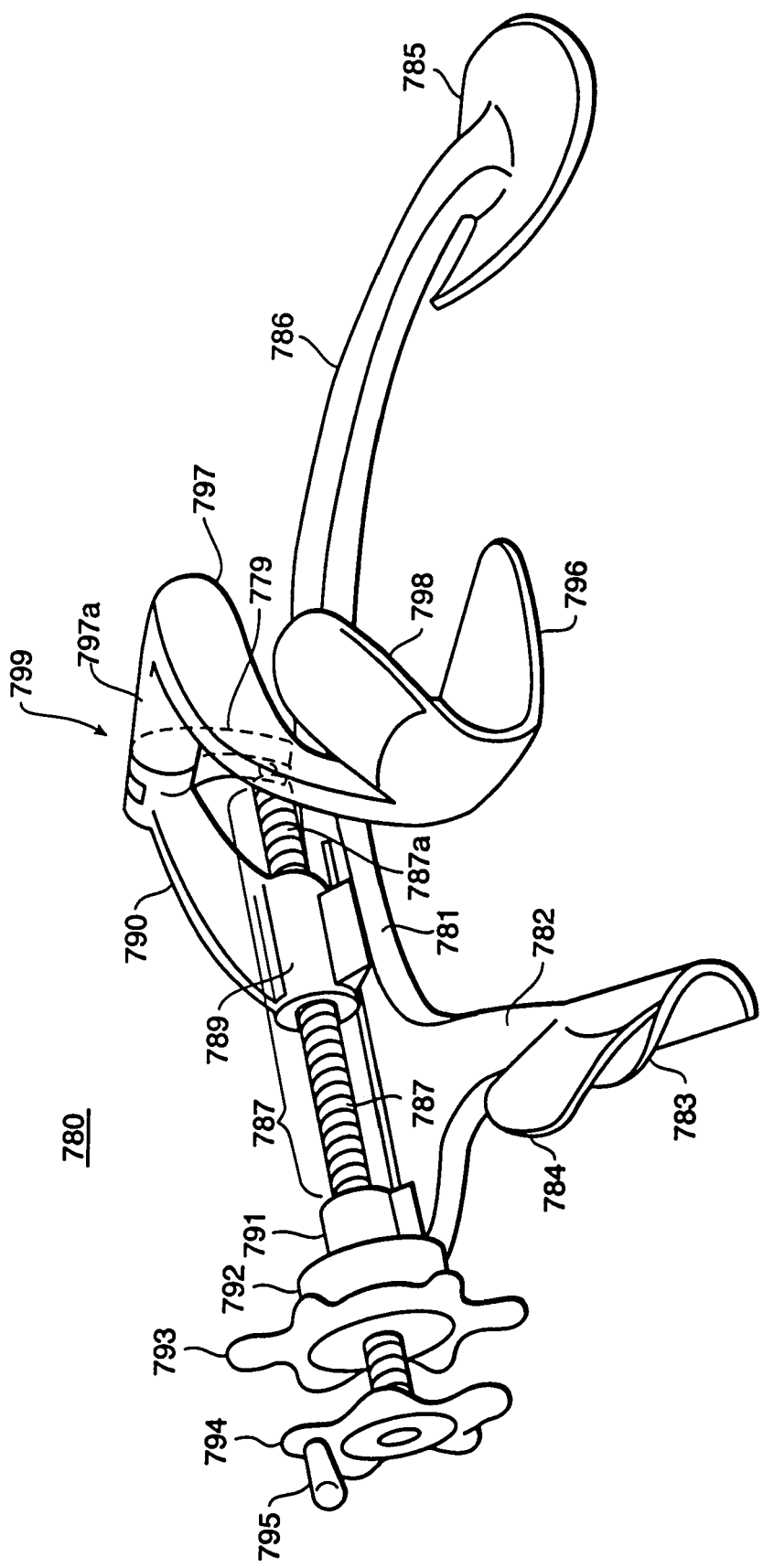
FIG. 39 is an isometric view of an sixteenth embodiment of the access platform of the present invention.

Referring to FIG. 39, a sixteenth embodiment of an access platform 780 comprises a generally elongated drive base 781 having a blade arm 782 extended generally in a normal direction from the drive base 781. A generally arcuate pad arm 786 extends generally longitudinally and downwardly from the drive base 781 and terminates at a sternal pad 785. A bearing support 791 extends upwardly from the drive base 781 adjacent the blade arm 782. An inferior blade 783 having a tissue retractor 784 extending therefrom attaches to the end of the inferior blade arm 782. In a preferred construction, the inferior blade 781, tissue retractor 784, blade arm 782, bearing support 791, drive base 781, pad arm 786 and sternal pad 785 are formed from one-piece construction.

A bearing 792 is mounted to the bearing support 791 and has a spreader handle 793 operably coupled thereto. A drive screw 787 having an offset handle 794 with a lever 795 attached to its first end, is threaded through the spreader handle 793 and freely passes through the bearing 792 and bearing support 791. The drive screw 787 extends longitudinally along the drive base 781 and is threaded through a carrier mount 789. The spreader handle 793 and the carrier mount 789 include oppositely wound threads. Rotation of the spreader handle 793 traversely drives the drive screw 787 and the carrier mount 789 mounted thereon along the drive base 781 and, thus, spreads or closes the blades 783 and 796. The carrier mount 789 includes a follower extending downwardly from its base that inserts into a drive slot 788 in the base 781. As the carrier mount 789 is translated across the drive base 781, the follower slides along the drive slot 788.

Extending upwardly and longitudinally outwardly in a direction away from the spreader handle 793, a carrier arm 790 extends from the carrier 789. At an end opposite the carrier mount 789, the carrier arm 790 pivotally captures at a pivot 799 a branch 797A of a blade arm 797. A tab 779 is fixed to the branch 797A adjacent the pivot 799 and extends downwardly in a direction normal to the branch 797A. The tab 779 contacts a shaft-end 787A of the drive shaft 787 opposite the offset handle 794 and extending beyond the carrier 789. The branch 797A extends outwardly from the pivot 799 in a normal direction to the carrier arm 790 and couples to the blade arm 797 at an end opposite the carrier arm 790. The blade arm 797 is generally arcuately shaped and extends downwardly from the branch 797A to connect to a superior blade 796 with a tissue retractor 798 extending therefrom. Because the pivot 799 is located above the superior blade 796, a lifting force is exerted on the superior blade 796 and ribs as a spreading force from the inferior blade 783 is transmitted to the superior blade 796 through the pivot 799.

Rotation of the offset handle 794, while holding the spreader handle 793 stationary, will thread the drive screw 787 through both the spreader handle 793 and the carrier 789, and thereby cause the drive screw 787 and carrier 789 to traverse the drive base 781 as well as causing the carrier 789 to traverse the drive screw 787 in the same direction. As a result, the carrier 789 traverses the drive base 781 at approximately two-times the speed that the carrier 789 traverses the drive screw 787 and thus, the length of the shaft-end 787A extending beyond the carrier 789 will increase or decrease at approximately one-half the speed at which the carrier 789 traverses the drive base 781. Therefore, as the offset handle 794 is rotated in a direction to spread the ribs, the ribs will be raised at a rate slower than they are spread as the superior blade 796 naturally rotates about the pivot 799 as the length of the shaft-end 787A extending beyond the carrier 789 decreases. Similarly, as the offset handle 794 is rotated in a direction to lower the offset ribs, the length of the shaft-end 787A will increase, at a rate slower than the rate at which the carrier 789 traverses the drive base 781. As the length of the shaft end 787A increases, it forces the tab 779, and thus the superior blade 797, to rotate in the counterclockwise direction around the pivot 799, and thereby further lowers the ribs. Because the carrier 789 traverses the drive base 781 at a faster rate than the shaft-end 787A increases, the distance between the blades 783 and 796 along the drive base 781 tends to decrease as the ribs are lowered.

To increase the rate at which the blades 783 and 796 are spread or closed relative to the rate at which the superior blade 796 is raised or lowered, the spreader and offset handles 793 and 794 are simultaneously counter-rotated relative to one another. Such a manipulation of the handles 793 and 794 will increase the rate at which the drive screw 787 traverses the drive base 781 and, thus, increase the rate at which the carrier 789 traverses the drive base 789 relative to the rate at which the carrier 789 traverses the drive screw 787 and increases or decreases the shaft end 787A.

To decrease the rate at which the blades 783 and 796 are spread or closed relative to the rate at which the superior blade 796 is raised or lowered, the spreader and offset handles 793 and 794 are rotated simultaneously in the same direction. By rotating the handles 793 and 794 in the same direction, the drive screw 787 is not translated in either direction along the drive-base 781. Thus, the carrier 789 will traverse the drive base 781 at the same rate it traverses the drive screw 787 and, therefore, the length of the shaft-end 787A will increase or decrease at the same rate at which the carrier 789 traverses the drive base 781. As a result, when the handles 793 and 794 are rotated in a direction to lower the superior blade 796, the spacing between the blades 783 and 796 along the drive base 781 remains relatively constant as the carrier 789 and the superior blade 796 traverse in opposite directions relative to the drive base 781.

In operation, the inferior and superior blades 783 and 796 are inserted into an incision in the patient's chest while the sternal pad 785 is positioned adjacent the patient's upper sternal-costal area. After the blades 783 and 796 and the sternal pad 785 are properly positioned, if the surgeon only desires to spread the ribs, only the spreader handle 793 is rotated in an appropriate direction to traversely drive the drive screw 787 and the carrier 789 along the drive base 781. As the carrier 789 is driven along the drive base 781, the superior blade 796 is separated from the inferior blade 783. If the surgeon wishes to raise the ribs as well as spread the ribs, the offset handle 794 is rotated in an appropriate direction to traversely drive the drive screw 787 and carrier across drive base 781 as well as traversely drive the carrier 789 along the drive screw 787. The spreader handle 793 is either held stationary, counter-rotated or rotated in the same direction, depending upon the desired rate of rib lift relative to the rate of rib spreading. As the blades 783 and 796 separate and the shaft-end 787A decreases, the superior blade 796 and ribs naturally lift and rotate in a clockwise direction about the pivot 799 as a torque is applied through the sternal pad 785 to the upper sternal-costal area of the patient's chest to maintain the lift in the superior blade 796 and ribs. While in the offset position, the surgeon can dissect the IMA.

To lower the superior blade 796 and ribs while maintaining the lateral separation of the blades 783 and 796, the offset and spreader handles 793 and 794 are simultaneously rotated in the same direction. As noted above, the drive screw 787 does not traverse the drive base 781 as the drive screw 787 is threaded through the carrier 789 to traversely drive the carrier 789 along the drive screw 787 and the drive base 781, as well as to increase the length of the shaft 787A beyond the carrier 789. As the length of the shaft-end 787A increases it tends to force the tab 779 to rotate in a counterclockwise direction about the pivot 799. Rotation of the tab 779 in a counterclockwise direction will rotate the superior blade 796 and ribs in a counterclockwise direction, and thereby lower the superior blade 796 and ribs. The counterclockwise motion of the superior blade 796 includes a lateral component that is directed away from the carrier 789 and which enables the lateral separation of the blades 783 and 796 to be substantially maintained as the superior blade 796 is lowered. With the blades 783 and 796 substantially level, the surgeon can perform other surgical procedures such as an arteriotomy and anastomosis.

Figure 40:
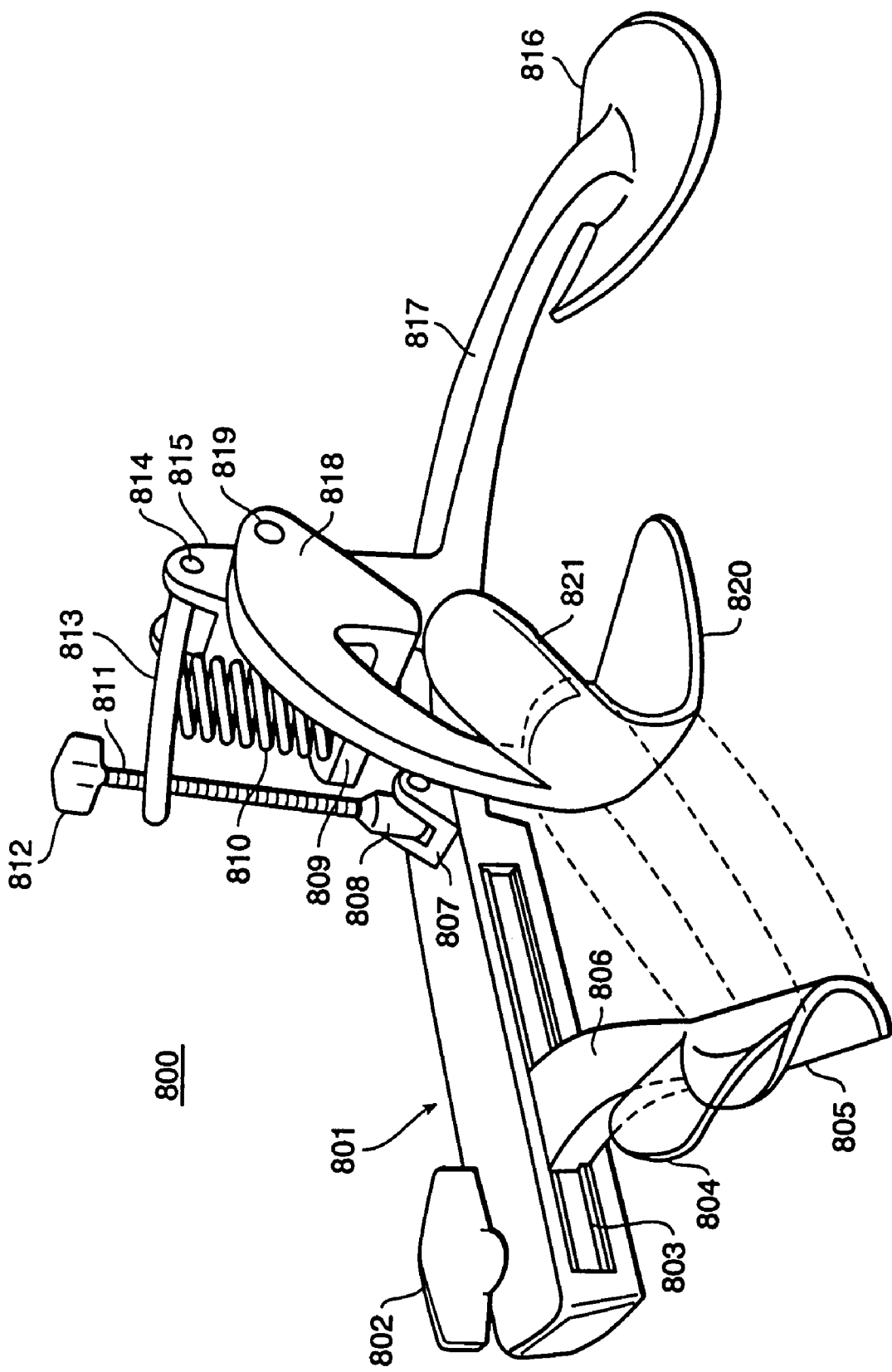
FIG. 40 is an isometric view of a seventeenth embodiment of the access platform of the present invention.
Figure 41:
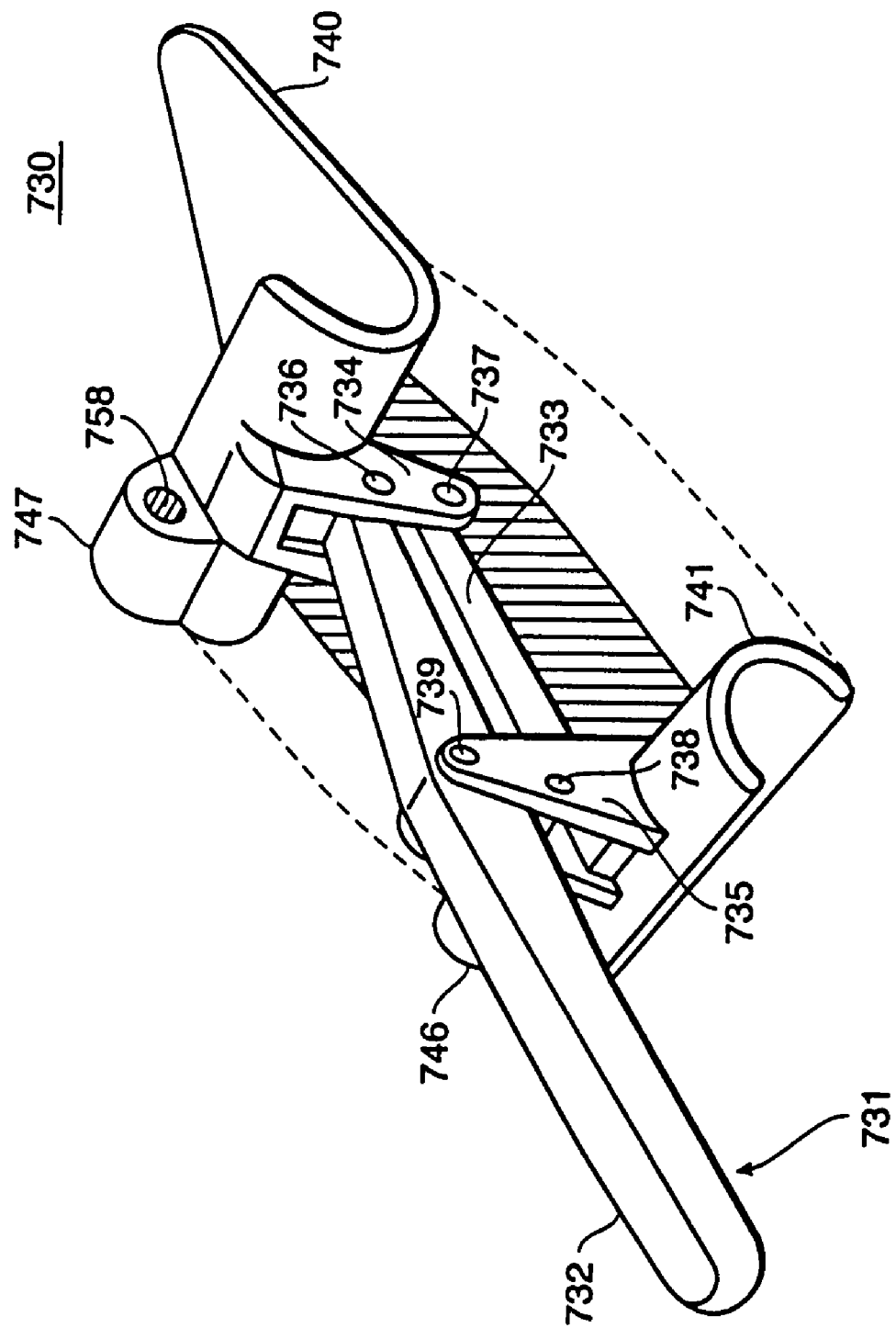
FIG. 41 is an isometric view of an eighteenth embodiment of the access platform of the present invention.

Turning to FIG. 40, a seventeenth embodiment of the access platform 800 comprises a spreader housing 801 which includes a drive mechanism housed therein (not shown) and a drive slot 803 cut into the spreader housing 801. A spreader lever 802 is mounted on the top of the spreader housing 801 and is operably connected to the drive mechanism housed therein. An inferior blade 805 having a tissue retractor 804 extending therefrom, is interconnected to the drive mechanism via a blade arm 806. The blade arm 806 extends outwardly from the spreader housing 801 in a generally normal direction.

A pad arm 817 connects at one end, or is formed integrally therewith, to the spreader housing 801 and extends outwardly therefrom. A sternal pad 816 is integrally formed on the pad arm 817 at an end opposite the housing 801. The pad arm 817 is generally arcuate to conform to an extended rib cage due to the offset of the ribs.

A superior blade 820 having a tissue retractor 821 extending therefrom, is connected to the bottom end of a generally arcuately shaped blade arm 818. The top end of the blade arm 818 is pivotally mounted on an offset stanchion 815 that extends upwardly from the pad arm 817. A compression member 813 is pivotally connected to the top of the stanchion 815 at pivot 814 and extends inwardly from the stanchion 815 toward the lever 802 on the spreader housing 801. An offset screw 811 having a handle 812 attached to its top end, is threaded through the compression member 813 at an end opposite the pivot 814 and is rotatably captured by a bushing assembly 808 rotatably coupled to a mount 807 that extends upwardly from the spreader housing 801. A counter-lift tab 809 extends inwardly from the blade arm 818 adjacent the stanchion 815. The lift tab 809 is operably connected to the compression member 813 through an offset spring 810 mounted therebetween.

In operation, the superior blade 820 and ribs are naturally lifted as the blades 805 and 820 are separated. Because the pivot 819 is located above the superior blade 820, a lifting force is exerted on the superior blade 820 and ribs while spreading is occurring. The spreading force from the inferior blade 805 is transmitted to the superior blade 820 through the high-mounted pivot 819. However, the lift of the ribs or, more particularly, the rotation of the superior blade 820 about the pivot 819 in a clockwise direction is inhibited by the force exerted by the offset spring 810. The superior blade 820 and ribs will not begin to lift until the moment force caused by the rotation of the superior blade 820 about the pivot 819 is greater than the spring force exerted by the offset spring 810 on the lift tab 809. The spring force is adjustable, and hence the amount of offset is adjustable, by rotating the handle 812 to lower or raise the compression member 813 along the offset screw 811. As the compression member 813 is lowered or brought closer to the tab 809, the spring force exerted by the offset spring 810 is increased, and hence the amount the superior blade 820 is lifted or rotated is decreased. Thus, the adjustable spring force can be used in a "pre-set" mode by the surgeon.

Referring to FIGS. 41-48, eighteenth and nineteenth embodiments of an access platform 730, 729 of the present invention advantageously lift and separate the superior blade 740 from the inferior blade 741 in a single motion. The access platform 730, shown in FIGS. 41-47, includes inferior and superior blades 741 and 740. The inferior blade 741 includes an elongated top portion for compression while the superior blade 740 includes an elongated bottom portion for lifting. The blades 740 and 741 are interconnected via an offset spreader assembly 731. The offset spreader assembly 731 includes an elongated handle 732 which is pivotally mounted adjacent its midpoint to an inferior blade mount 735 at a pivot 739 and is pivotally mounted adjacent a first end to a superior blade mount 734 at a pivot 736. The inferior blade mount 735 extends upwardly from the top of the inferior blade 741 and the superior blade mount 734 extends downwardly from the back side of the superior blade 740. A stabilizing link 733 is pivotally mounted to the superior blade mount 734 at pivot 737 and the inferior blade mount 735 at pivot 738. As the link 733 extends between the blades 740 and 741, it remains substantially parallel to the handle 732.

Figure 42:
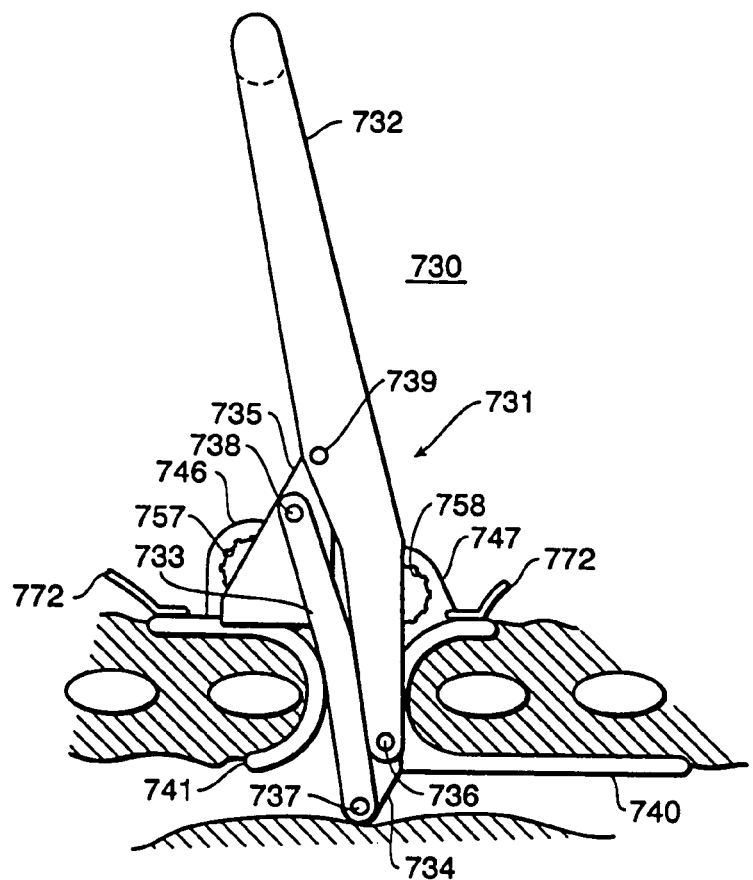
FIG. 42 is a front elevation view of the access platform in FIG. 41 in a pre-spreading closed mode positioned between a patient's ribs.
Figure 43:
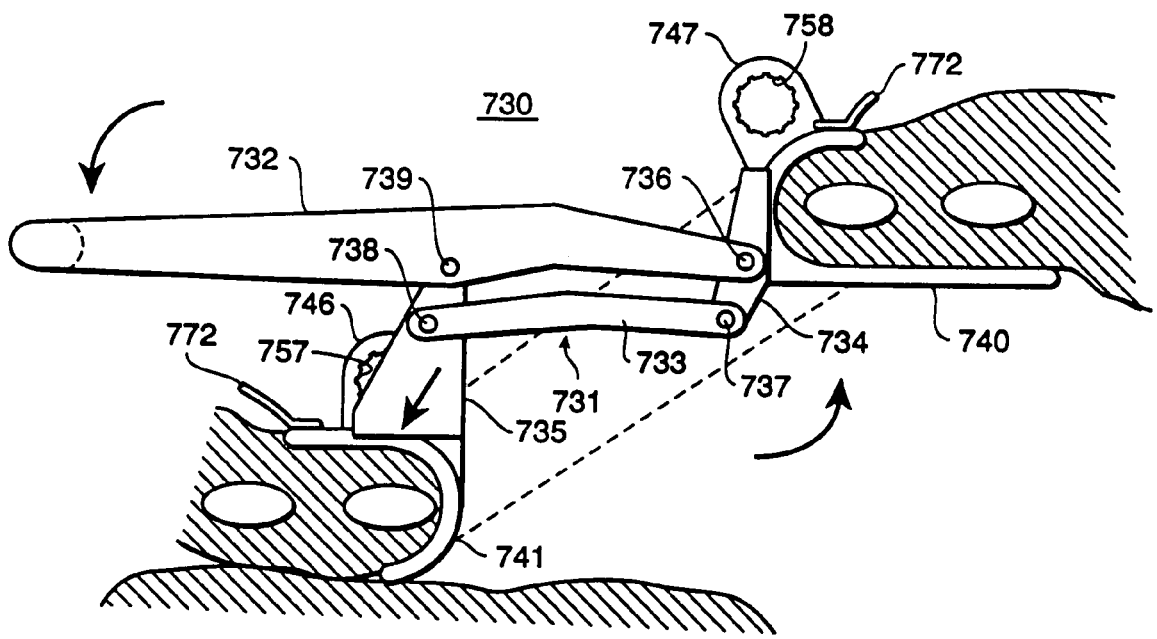
FIG. 43 is a front elevation view of the access platform in FIG. 41 in an open mode positioned between a patient's ribs.
Figure 44:
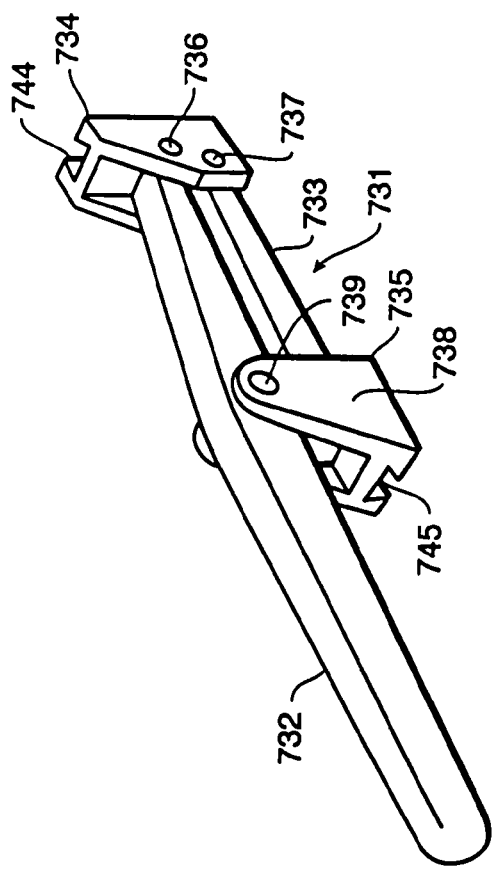
FIG. 44 is an isometric view of a removable offset spreader assembly utilized with the access platform in FIG. 41.
Figure 45:
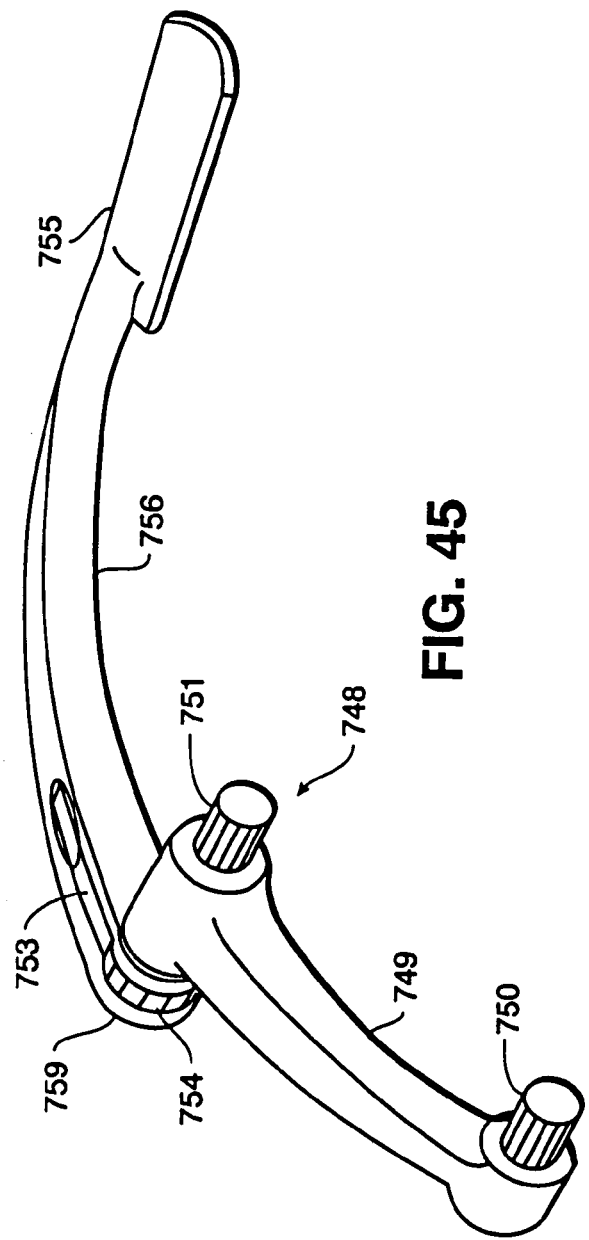
FIG. 45 is an isometric view of an offset positioning assembly utilized with the access platform in FIG. 41.
Figure 46:
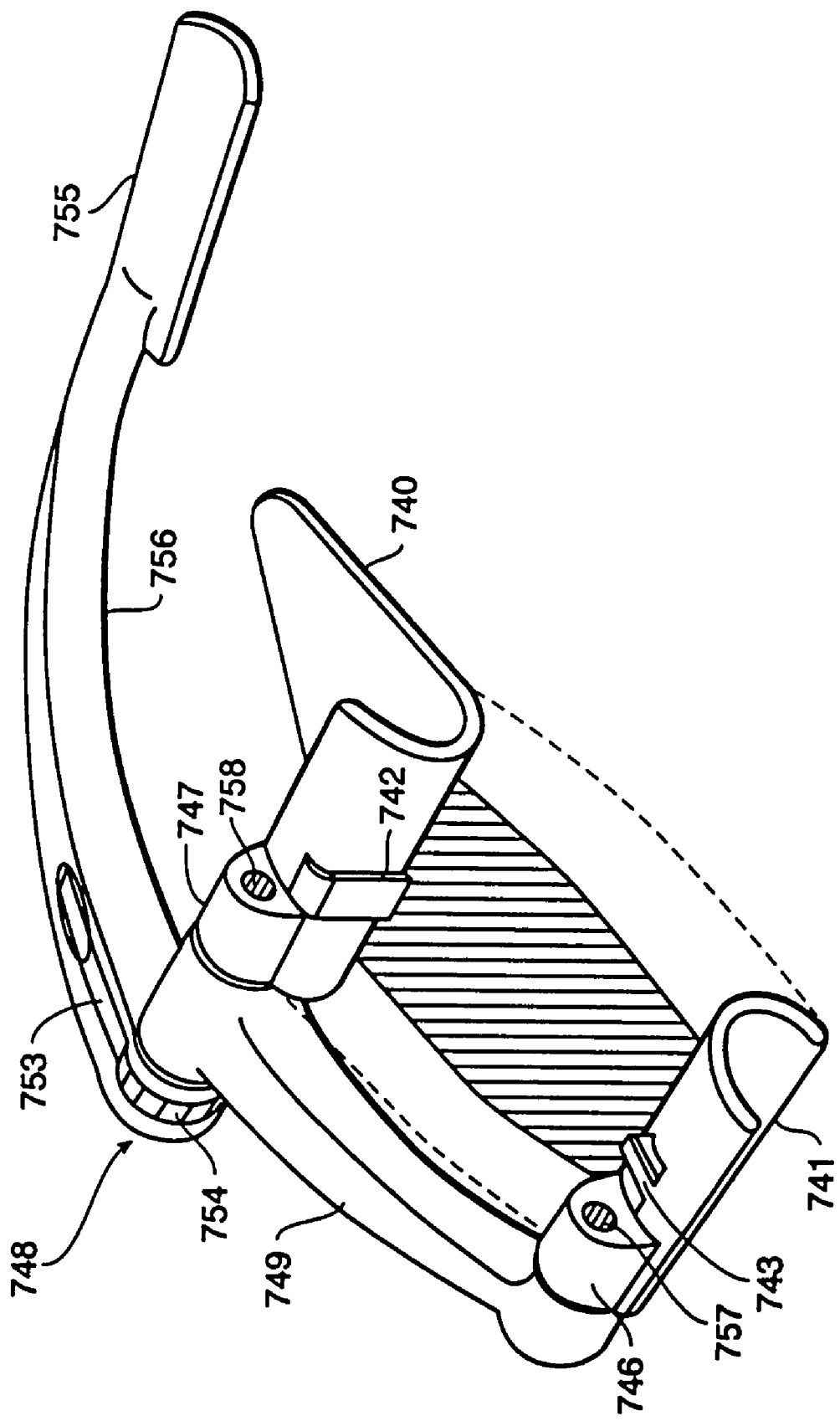
FIG. 46 is an isometric view of the access platform in FIG. 41 with the offset spreader assembly in FIG. 44 removed and the offset positioning assembly in FIG. 45 attached.
Figure 47:
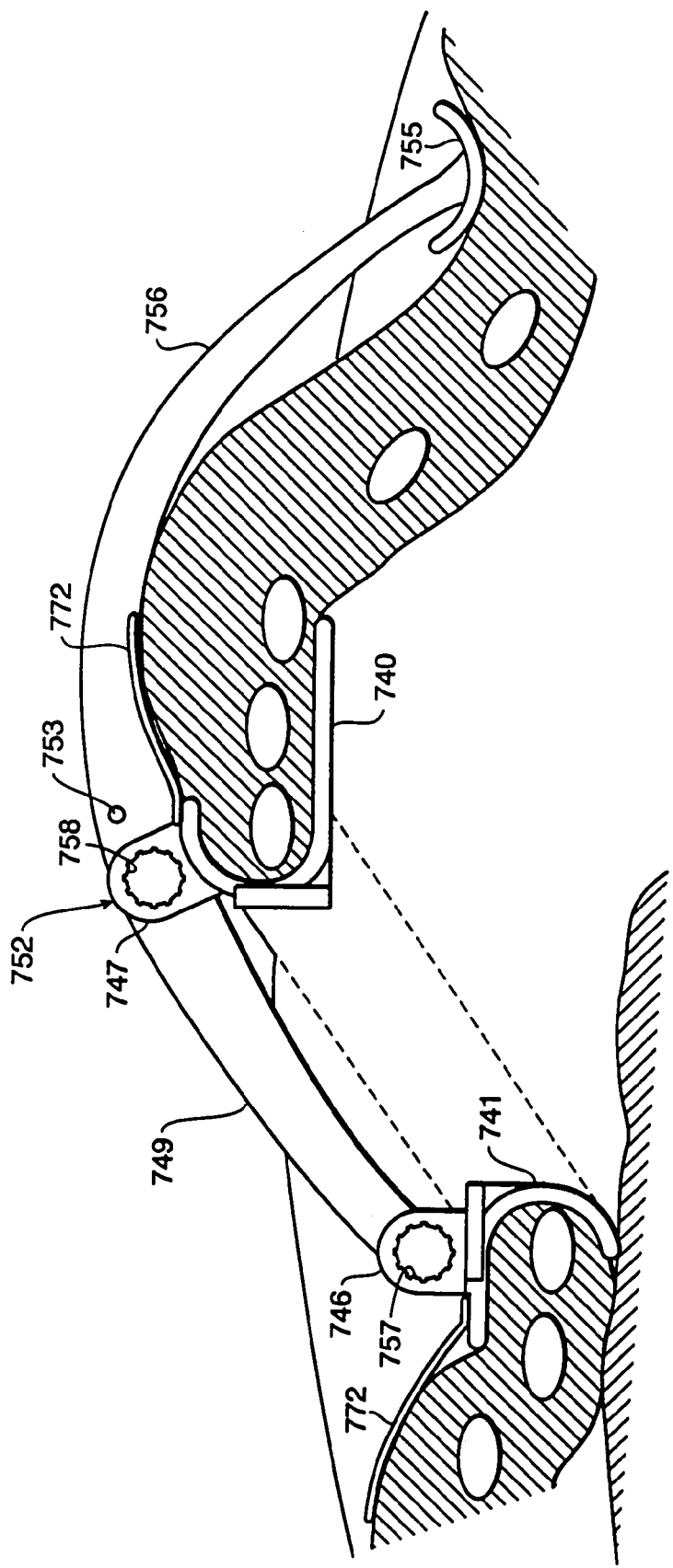
FIG. 47 is a front elevation view of the access platform in FIG. 46 in an engaged position maintaining the lift and separation of a patient's ribs.

Turning to FIG. 42, the access platform 730 is shown in a closed position with the superior and inferior blades 740 and 741 engaging the superior and inferior ribs, respectively. Force is applied to a free second end of the handle 732 to rotate the handle 732 in a counterclockwise rotation about pivot 739 (see FIG. 43). As a result, the first end of the handle 732 that is pivotally attached to the superior blade mount 734 at pivot 736, lifts and separates the superior blade 740 and ribs in a single motion from the inferior blade 741 and ribs.

Turning to FIGS. 44-47, the offset spreader assembly 731 of the access platform 730 is removable. An offset positioning assembly 748 is utilized to maintain the lift and separation between the blades 740 and 741 and advantageously open up the surgeon's access to dissect the IMA. The removable offset spreader assembly 731 incorporates a dovetail type assembly to mate the blade mounts 734 and 735 with the blades 740 and 741, respectively. Pins 742 and 743 which protrude from the back side of the superior blade 740 and the top side of the inferior blade 741 mate with tails 744 and 745 formed in the blade mounts 734 and 735, respectively.

The offset positioning assembly 748 comprises a positioning arm 749 having shafts 750 and 751 extending therefrom at opposing ends. The shafts 750 and 751 mate with holes 757 and 756 formed in positioning mounts 746 and 747 extending up from the inferior and superior blades 741 and 740. The shafts 750 and 751 and the holes 757 and 758 include finely cut splines to maintain the discreet positions of the blades 740 and 741 relative to one another. An arcuate pad arm 756 terminates into a forked hub 759 at one end and a sternal pad 755 at another end. The hub 759 rotatably captures the shaft 751 on a side of the positioning arm 749 opposite the positioning mount 774. A pawl 753 pivotally captured in a recess in the pad arm 756 engages a ratchet 754 mounted on the shaft 751. The sternal pad 755, pad arm 756 and hub 759 are free to rotate about the shaft 751 in a clockwise direction. To rotate the sternal pad 755, pad arm 756 and hub 759 in a counterclockwise direction, the pawl 753 is depressed at an end opposite the ratchet 754 to disengage the pawl 753 from the ratchet 754. With the pawl 753 disengaged, the hub 759 is free to rotate about the shaft 751 in a counterclockwise direction.

In operation, the handle 732 is first rotated in a counterclockwise direction to lift and separate the superior blade 740 and ribs from the inferior blade 741 and ribs. Once in the offset position, the offset positioning assembly 748 is engaged by sliding the shafts 750 and 751 into the holes 757 and 758 of the positioning mounts 746 and 747 on the inferior and superior blades 741 and 740. The pad arm 756 is rotated downwardly until the sternal pad 755 contacts the patient's chest (see FIG. 47). The offset spreader assembly 731 is then removed by sliding the tails 744 and 745 of the blade mounts 734 and 735 off of the pins 742 and 743 of the blades 740 and 741. With the offset spreader assembly 731 removed, the offset positioning assembly 748 holds the blades 740 and 741 apart and applies the necessary torque against the patient's upper sternal-costal area to maintain the lift on the superior blade 740 and ribs. While in the offset position, the access to dissect the IMA is wide open.

Figure 48:
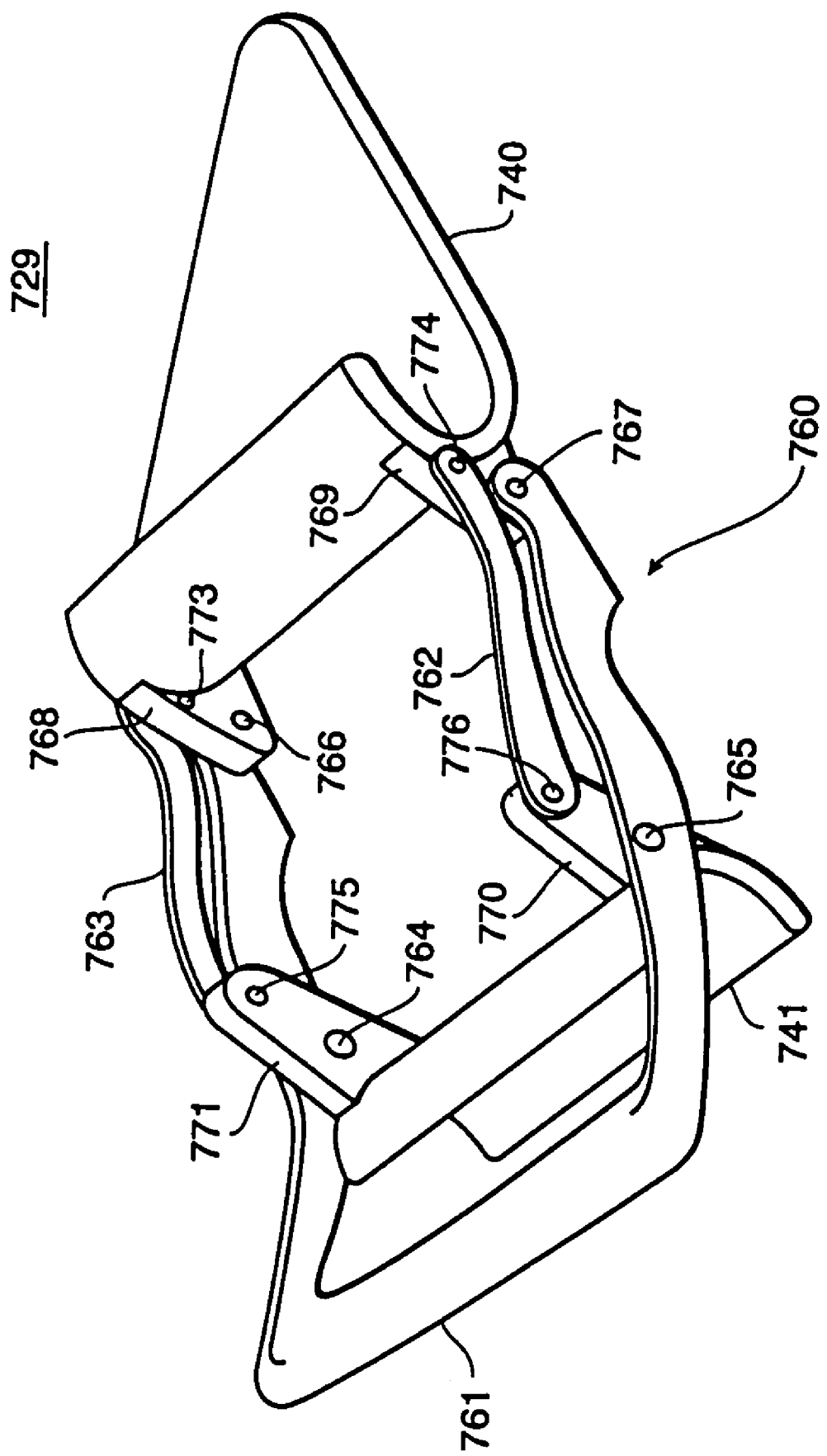
FIG. 48 is an isometric view of a nineteenth embodiment of an access platform of the present invention.
Figure 50:
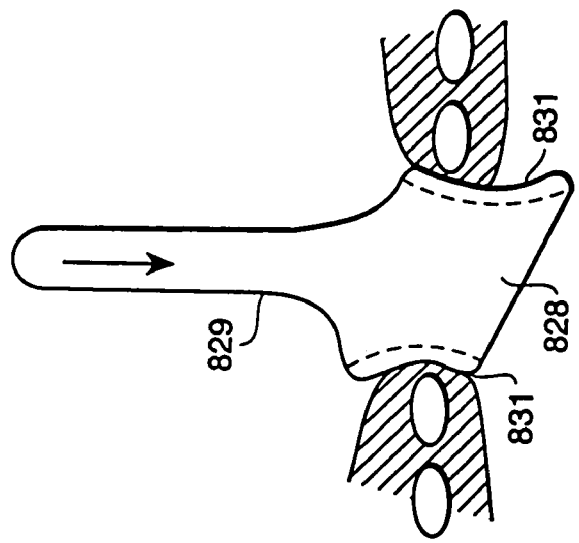
FIG. 50 is a partial sectional isometric view of the access platform in FIG. 49.
Figure 49:
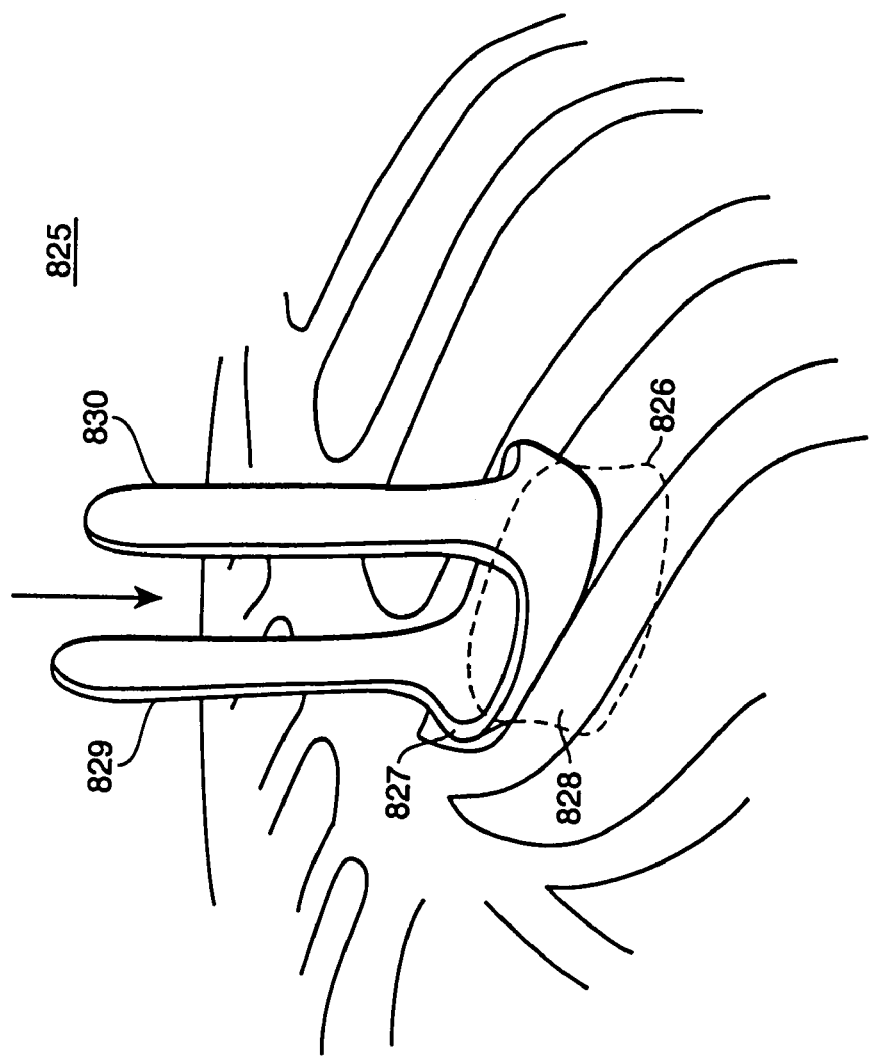
FIG. 49 is an isometric view of a twentieth embodiment of the access platform of the present invention positioned between a patient's ribs.
Figure 52:
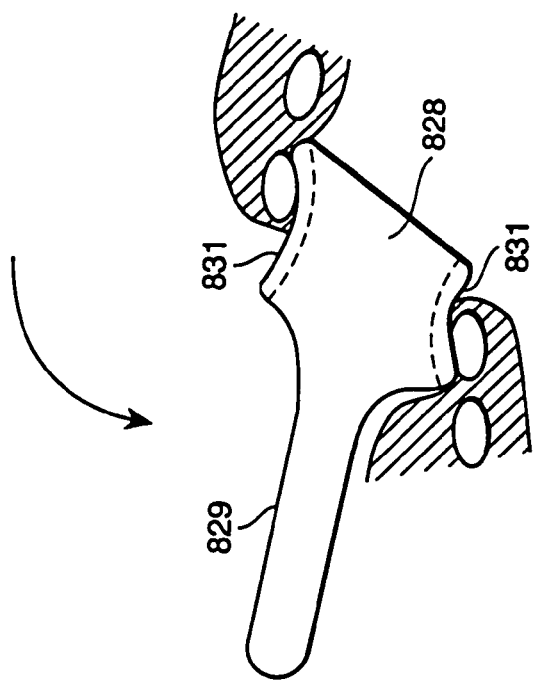
FIG. 52 is a partial sectional isometric view of the access platform in FIG. 51.
Figure 51:
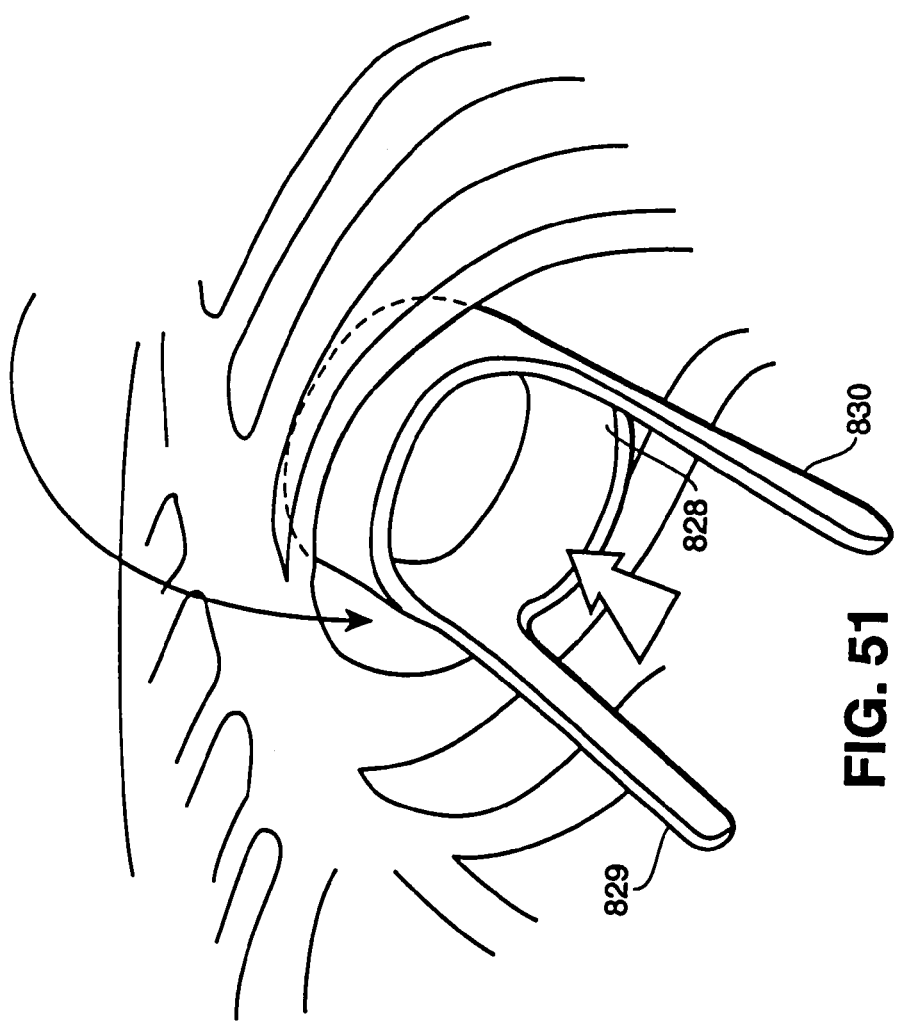
FIG. 51 is an isometric view of the access platform in FIG. 49 rotated to access the IMA.
Figure 54:
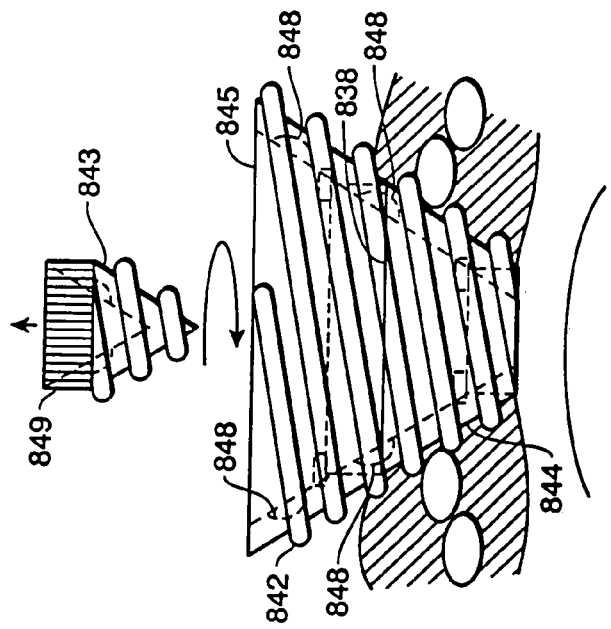
FIG. 54 is an elevation view of the access platform in FIG. 53 in an intermediately engaged position.
Figure 56:
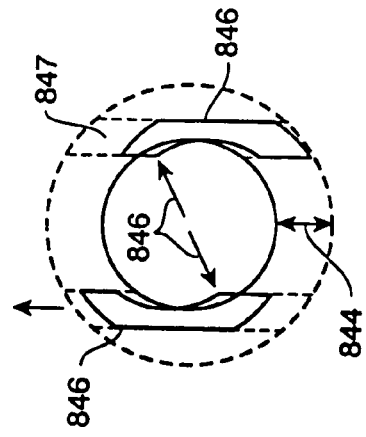
FIG. 56 is a top view of a locking assembly of the access platform in FIG. 53.
Figure 53:
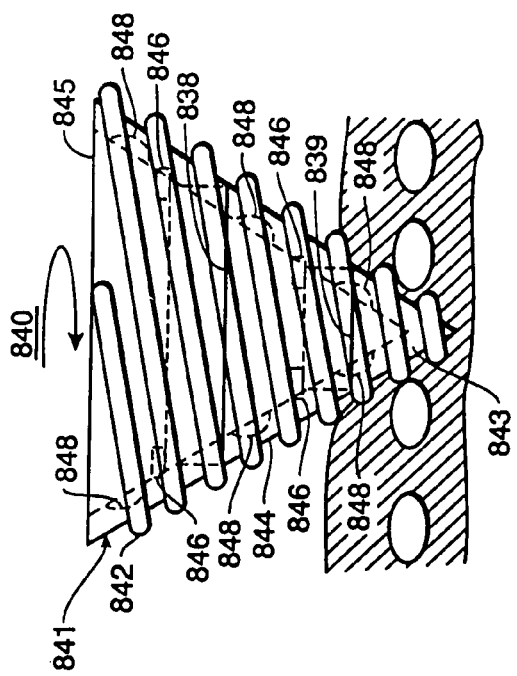
FIG. 53 is an elevation view of a twenty-first embodiment of the access platform of the present invention entering a patient's chest cavity.
Figure 55:
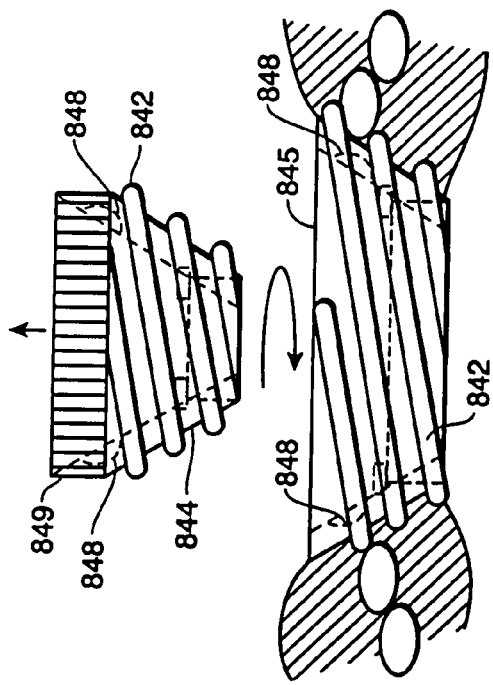
FIG. 55 is an isometric view of the access platform in FIG. 53 in a final engaged position.

Referring to FIG. 48, an offset spreader assembly 760 of a nineteenth embodiment of the access platform 729 includes a U-shaped handle 761 pivotally connected to inferior blade mounts 771 and 770 at pivots 764 and 765, and superior blade mounts 768 and 769 at pivots 766 and 767. A pair of parallel stabilizing links 762 and 763 are pivotally connected to superior blade mounts 768 and 769 at pivots 773 and 774 and inferior blade mounts 770 and 771 at pivots 775 and 776. The inferior blade mounts 770 and 771 extend upwardly from the inferior blade 741 while the superior blade mounts 768 and 769 extend downwardly from the superior blade 740.

In operation, force is applied to the free end of the handle 761 to rotate the handle 761 in a counterclockwise direction about pivots 764 and 765 on the inferior blade mounts 771 and 770 and lift and separate the superior blade 740 in a single motion from the inferior blade 741. The U-shaped handle 761 and stabilizing links 762 and 763 facilitate the lateral stability of the access platform 729. In the offset position, the handle 761 and links 762 and 763 advantageously remain clear of the access space, and thus provide the surgeon with open access to dissect the IMA.

Turning to FIGS. 49-52, a bladeless twentieth embodiment of the access platform 825 comprises a tubular retractor body 828 having concave shaped sidewalls 831 extending between a top edge 827 and a bottom edge 826 of the body 828. Extending vertically from the top edge 827 of the tubular body 828 is a pair of elongated handles 829 and 830. The handles 829 and 830 may be formed integrally with the body 828 or removably or hingedly coupled to the body 828.

In operation, the tubular body 828 with its advantageously sloped bottom edge 826, is wedged between the inferior and superior ribs. Once in position, the handles are used to rotate the tubular body 828 approximately 90° (see FIGS. 51 and 52) to offset the superior and inferior ribs. While in the offset position, the surgeon can dissect the IMA. While in the upright position, the surgeon can perform such surgical procedures as an arteriotomy and an anastomosis. Preferably, the access platform 825 is formed from a resilient polymer or stainless steel, and can be easily constructed as a single piece.

Referring to FIGS. 53-56, a bladeless twenty-first embodiment of the access platform 840 is formed as a three-piece hollow cone 841 having threads 842 wrapped about the full exterior of the cone 841. The cone 841 includes a hollow frustum shaped intermediate member 844 interconnected to a conically shaped tip member 843 and a hollow frustum shaped top member 845. The top and tip members 845 and 843 are connected to the intermediate member 844 at parting lines 838 and 839, respectively, and locked in place with locking tabs 846. The locking tabs 846 are slidably received in locking grooves 847 (see FIG. 56). The locking tabs 846 prevent upward vertical movement of the tip member 843 relative to the intermediate member 844 and upward vertical movement of the intermediate member 844 relative to the top member 845. Relative rotational movement between coupled members is prevented by splined connections 849. Finger or driving tool pockets 848 are included in the interior of the top, intermediate and tip members 845, 844 and 843 to aid in the manipulation of the cone 841.

In operation, the tip member 843 pierces the tissue and draws the intermediate member 844 downward toward the ribs as the cone 841 is rotated. As the intermediate member 844 is drawn downward it begins to spread the inferior and superior ribs while the threads 842 engage the inferior and superior ribs to maintain the vertical position of the cone 841. With the intermediate member 844 properly in position, the tip member 843 is removed from the cone 841. The cone 841 is rotated until the top member 845 separates the inferior and superior ribs and the threads 842 about the top member 845 engage the inferior and superior ribs. With the top member 845 properly in position, the intermediate member 844 is removed from the cone 841 leaving only the top member 845 in place between the inferior and superior ribs, and thus, providing access to the patient's heart for the surgeon to perform surgical procedures.

A variety of drive mechanisms discussed below (FIGS. 35-38 and 57-65) could be incorporated in the access platform embodiments discussed herein. Referring to FIGS. 35-38, a drive mechanism 970 preferably comprises a modified block and tackle assembly. The drive mechanism 970 includes a pulley 971 mounted in the spreader housing 702 at a first end, two intermediate pulleys 972 and 973 mounted on the drive block 708 which is interconnected to a superior blade and slidably positioned within the housing 702, and a pulley 974 and a clutch 976 mounted in the housing at a second end adjacent the base mount 704 which is interconnected to an inferior blade and fixedly mounted within the housing 702. A cable 988 is conventionally wrapped around the pulleys 971, 972, 973 and 974 and clutch 976 to transversely drive the drive block 708 away from the base mount 704 to spread the superior and inferior ribs. The two ends of the cable 988 are tied to a tensioning spring 987 mounted in the drive block 708. The cable tensioning spring 987 provides a preload force (preferably about three pounds) necessary to maintain a sufficient preload tension on the drive cable 988.

Figure 36:
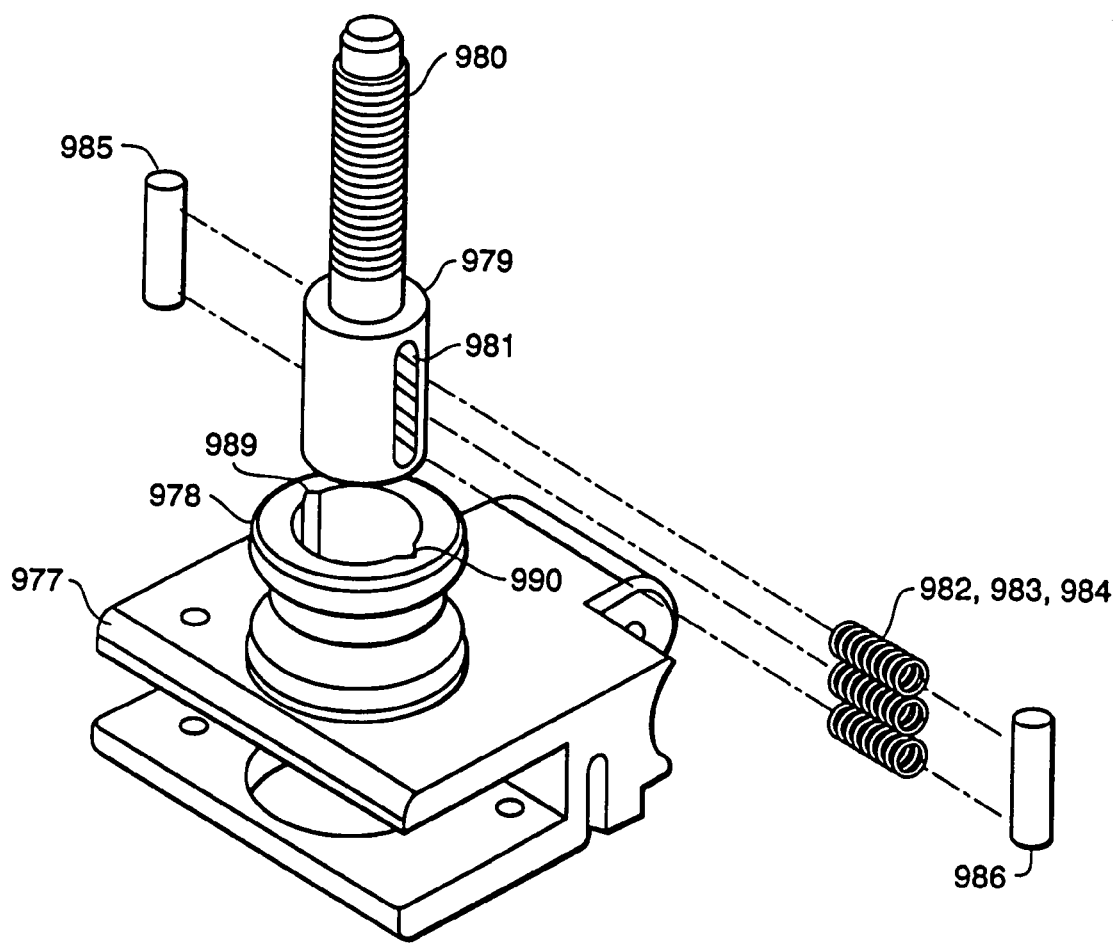
FIG. 36 is an isometric view of a clutch assembly of the drive assembly in FIG. 35.
Figure 37:
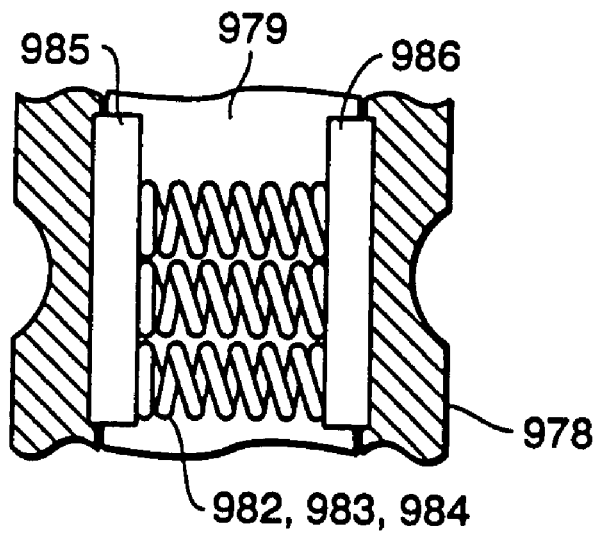
FIG. 37 is a partial cross-sectional view of the clutch assembly in FIG. 36.
Figure 38:
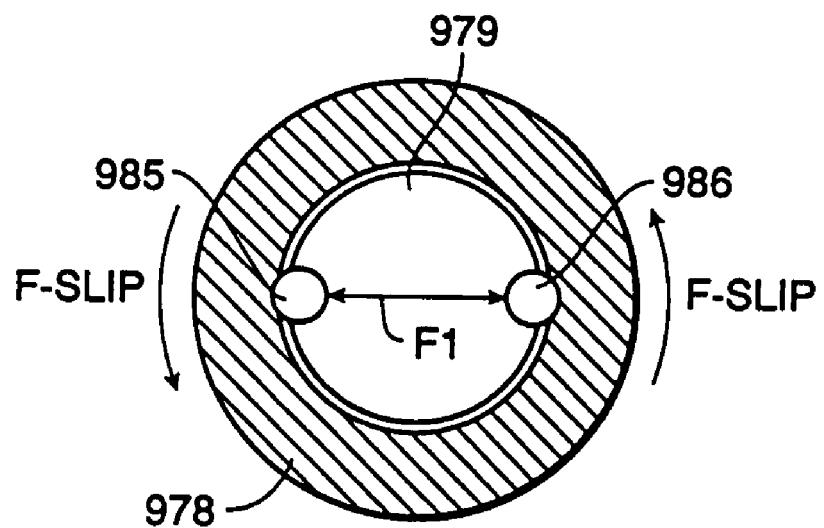
FIG. 38 is a partial top schematic of the clutch assembly in FIG. 36.

Referring to FIGS. 36-38, the clutch mechanism 976 includes a clutch housing 977 having a cylindrical capstand 978 mounted therein and a hub 979 coaxially positioned within the capstand 978. A hub shaft 980 extends upwardly from the hub 979 out of the spreader housing 702 where it is coupled to the lever 701 (see FIG. 33). Two opposing dowel pins 985 and 986 reside longitudinally along the circumference of the hub 979. The dowel pins 985 and 986 are partially captured in longitudinal recesses 989 and 990 formed in the interior of the capstand 978 and in a slot 981 bored through the hub 979. A spring mechanism comprising three parallel springs 982, 983 and 984 resides in the slot 981 and biases the dowel pins 985 and 986 outward with a force F1.

The amount of drive or output force that can be exerted on the superior blade is dictated by the diameter of the capstand 978 and the number of times the cable 988 is wound around the capstand 978. Thus, as the diameter of the capstand 978 is increased, the amount of force that can be exerted by the drive mechanism 970 on the blades is decreased. In addition, as the number of times the cable is wound around the capstand 978 increases, the amount of force that the drive mechanism 970 can exert on the blades is increased.

Preferably, the drive mechanism 970 provides about 50 pounds (±10-15%) of drive force on the blades with a minimum force of preferably about 10 to 20 pounds being applied to the lever 701. Only about 30-40 pounds of drive force is necessary to spread the ribs on the heaviest of patients. The clutch 976 advantageously provides a slip or overdrive mechanism which ceases the drive force on the blades. This slip force (F slip) is preferably about 50 pounds.

At the prescribed slip force, enough torque is transmitted by the capstand 978 on the dowel pins 985 and 986 to overcome the spring bias F1 on the dowel pins 985 and 986 and push the dowel pins 985 and 986 within the slot 981 of the hub 979 such that the hub 979 slips within the capstand 978. As the hub 979 slips within the capstand 978, the blades are prevented from being spread any further and, thus, advantageously prevented from accidentally breaking any of the ribs.

Figure 57:
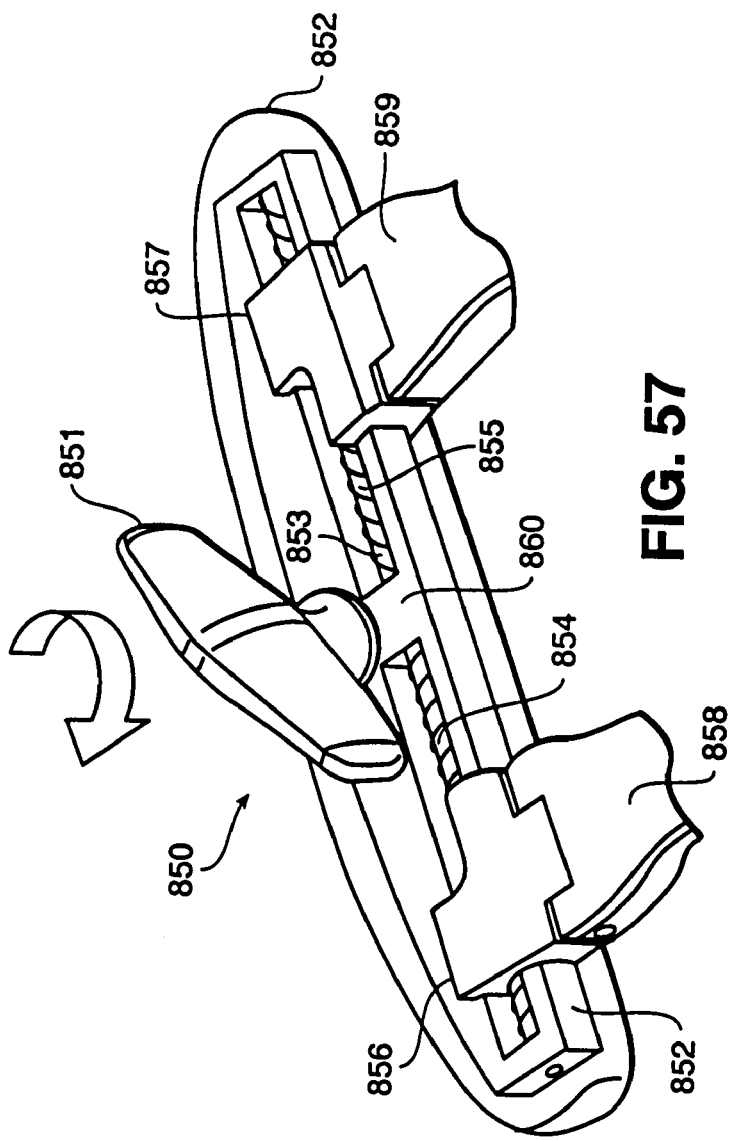
FIG. 57 is an isometric view of a spreader member drive assembly.

Referring to FIG. 57, a drive mechanism 850 comprises a lead screw 853 that is mounted in an elongated carrier 852 and operably coupled to a drive lever 851 at a gear box 860. The lead screw 853 includes oppositely wound threads on first and second portions 854 and 855 of the lead screw 853. The lead screw 853 is operably coupled to a pair of drive blocks 856 and 857 that are slidably mounted on the carrier 852 and coupled to blade arms 858 and 859, respectively. The rotation of the lead screw 853 in a first direction causes the drive blocks 856 and 857 to separate and in turn separate a patient's ribs. The rotation of the lead screw 853 in a second direction draws the drive blocks 856 and 857 together.

Figure 58:
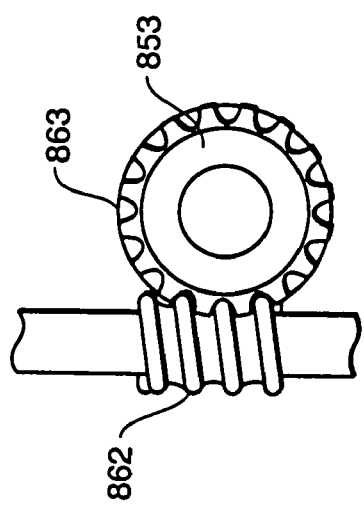
FIG. 58 is a partial detail elevation view of a drive gear assembly for the drive assembly in FIG. 57.
Figure 59:
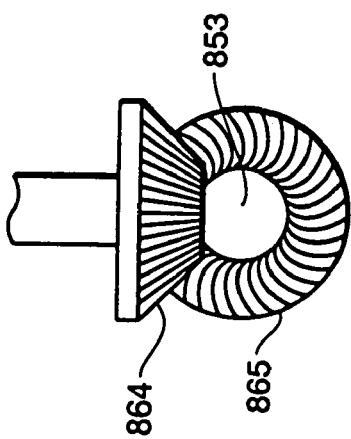
FIG. 59 is a partial detail elevation view of a drive gear assembly for the drive assembly shown in FIG. 57.

Referring to FIGS. 58 and 59, the gear drive of the drive mechanism 850 includes either an assembly of worm gears 862 and 863 or an assembly of bevel gears 864 and 865. The worm gear 862, 863 (FIG. 58) arrangement tends to provide a high ratio drive which results in slow separation of the drive blocks 856 and 857. The threads on the lead screw 853, however, include a long or steep pitch to increase the speed of adjustment of the drive blocks 856 and 857. With a worm-gear drive mechanism 862, 863, back driving of the drive blocks 856 and 857 is inherently prevented.

In the bevel gear 864, 865 (FIG. 59) drive arrangement, the drive ratio is substantially 1:1 which results in a fast separation of the drive blocks 856 and 857. To compensate for this fast adjustment, the lead screw 853 includes shallow or short pitched threads. A pawl (not shown) is operably coupled to the threads of the lead screw 853 to prevent back driving of the drive blocks 856 and 857. If the pitch of the threads is sufficiently shallow or short, back driving will be inherently prevented and, thus, the need for a pawl will be eliminated.

Figure 60:
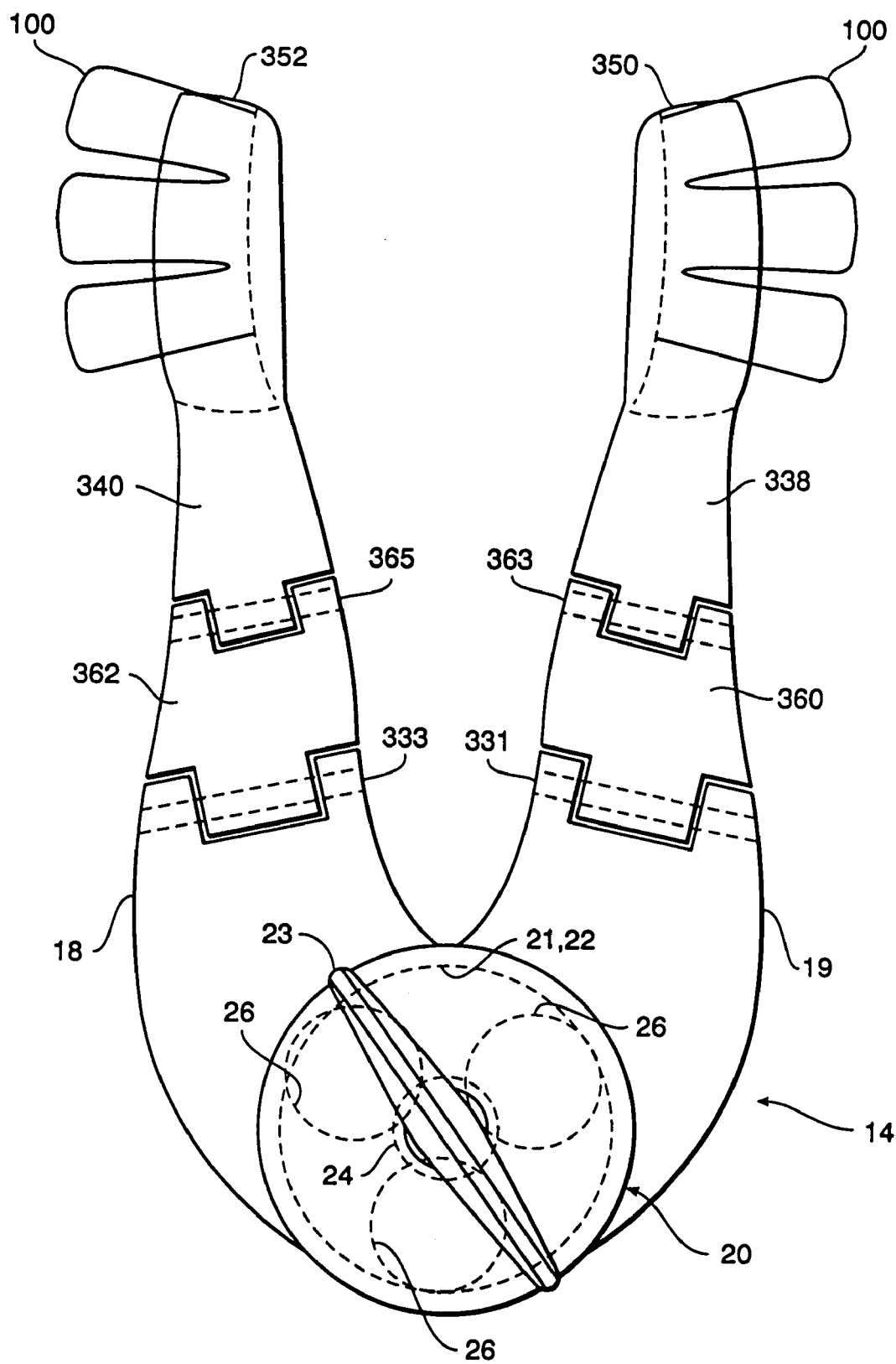
FIG. 60 is a top view of an access platform combining the access platform embodiment in FIG. 19 with the drive gear assembly in FIG. 3.

Referring to FIG. 60, an access platform includes a combination of the harmonic gear drive 20 and spreader assembly of the first embodiment discussed herein (FIGS. 2 and 3) and pivotally coupled blade arms of the fifth embodiment discussed herein (FIG. 19). In addition, the blades 350 and 352 are curved to compensate for the orientation of the access platform relative to the ribs of the patient.

Figure 61:
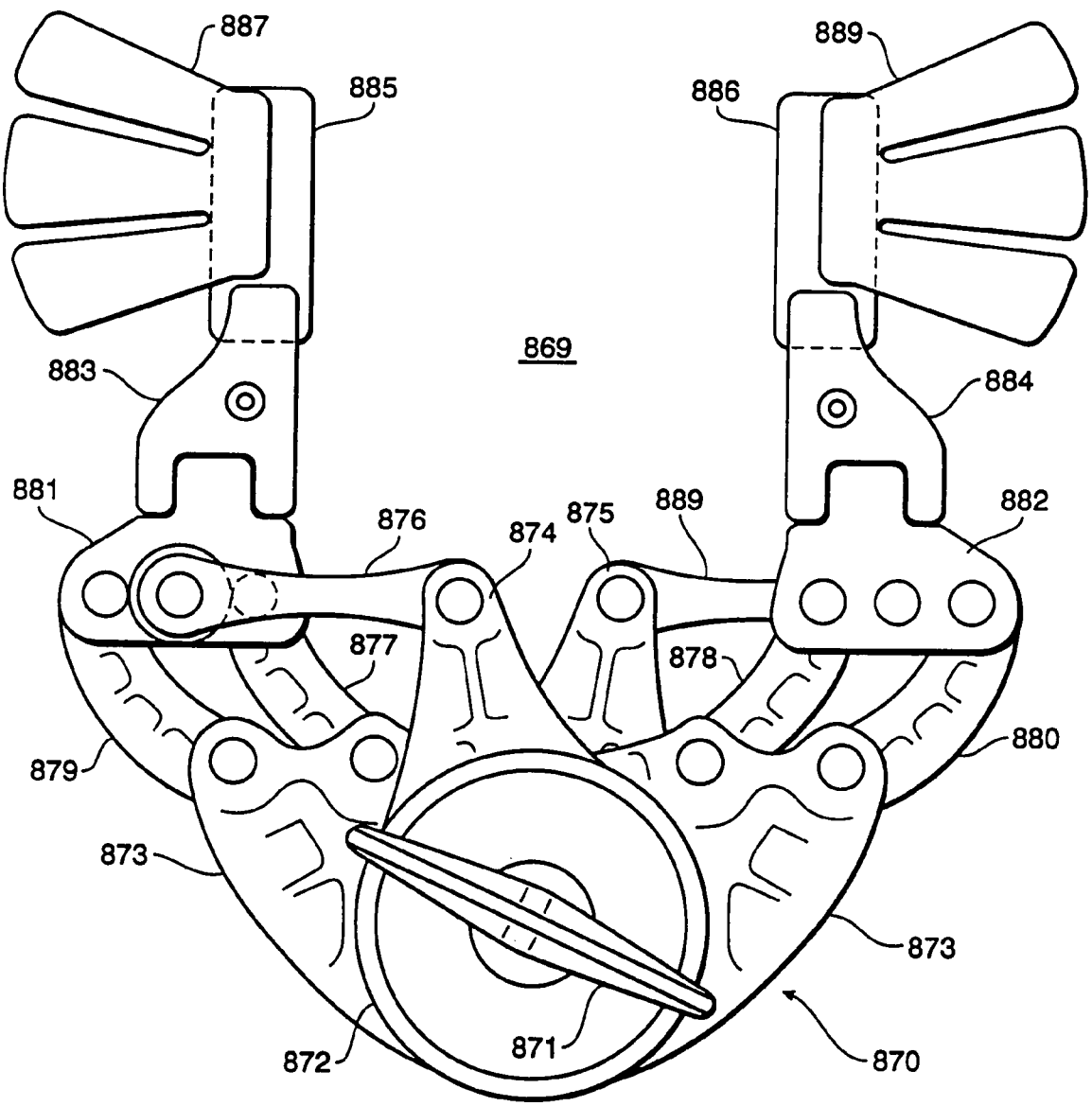
FIG. 61 is a top view of the access platform in FIG. 60 incorporating an alternate spreader member drive assembly.

Turning to FIG. 61, an access platform 869 resembling the fourth embodiment shown in FIG. 18, includes a drive assembly 870 comprising spreader arms 874 and 875 coupled to a drive 872 having a drive lever 871. Spreader links 876 and 889 are pivotally coupled to spreader arms 874 and 875, respectively, and to blade arm mounts 881 and 882, respectively. Blade arms 883 and 884 are pivotally coupled to the blade arm mounts 881 and 882, respectively, and are connected to blades 885 and 886, respectively. The blades 885 and 886 include tissue retractors 887 and 889.

To advantageously maintain a parallel arrangement between the blades as they are separated, inner and outer guide links 877 and 878, 879 and 880, respectively, are pivotally coupled to the blade arm mounts 881 and 882 and a spreader base 873.

Figure 62:
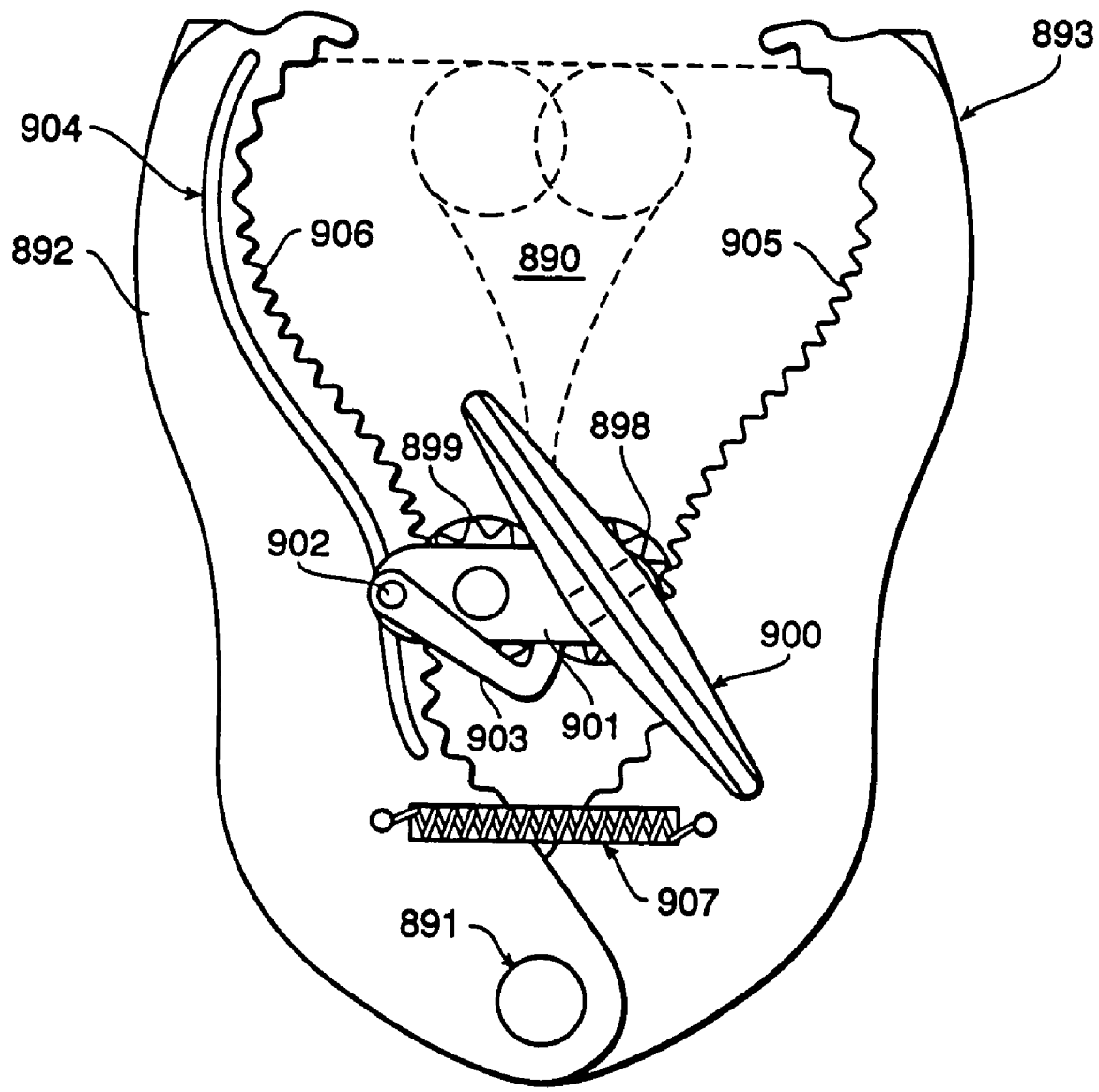
FIG. 62 is a top view of a spreader member drive assembly for an access platform.

Referring to FIG. 62, a drive mechanism 890 comprises a pair of curved gear racks 905 and 906 formed on the interior of blade arms 892 and 893, which are pivotally connected at a main pivot 891. Dual pinion gears 898 and 899 are operably connected to one another and to the curved racks 905 and 906, and are coupled together by a support 901. A handle 909 drives the first pinion 898 which drives the second pinion 899. A pawl 903, pivotally connected to the support 901, engages the teeth of the first pinion 898 to prevent back drive of the dual pinion gears. A common pin 902 used to pivotally mount the pawl 903 on the support 901 follows along a track 904 in the blade arm 892 to maintain contact between the second pinion 899 and the curved rack 906. A tensioning spring 907 attached to the blade arms 893 and 892 acts to maintain contact between the curved rack 905 and the first pinion 898. The curved gear racks 905 and 906 advantageously cause a constant effort to be exerted on the handle 900 as the blade forces on the blades 894 and 895 increase due to the separation of the ribs. More particularly, as the blade forces increase as the pinion gears 898, 899 move closer to the pivot 891, a given rotation of the handle 900 will open the blades a progressively small distance and, thus, keep the forces at the handle 900 relatively constant.

Figure 63:
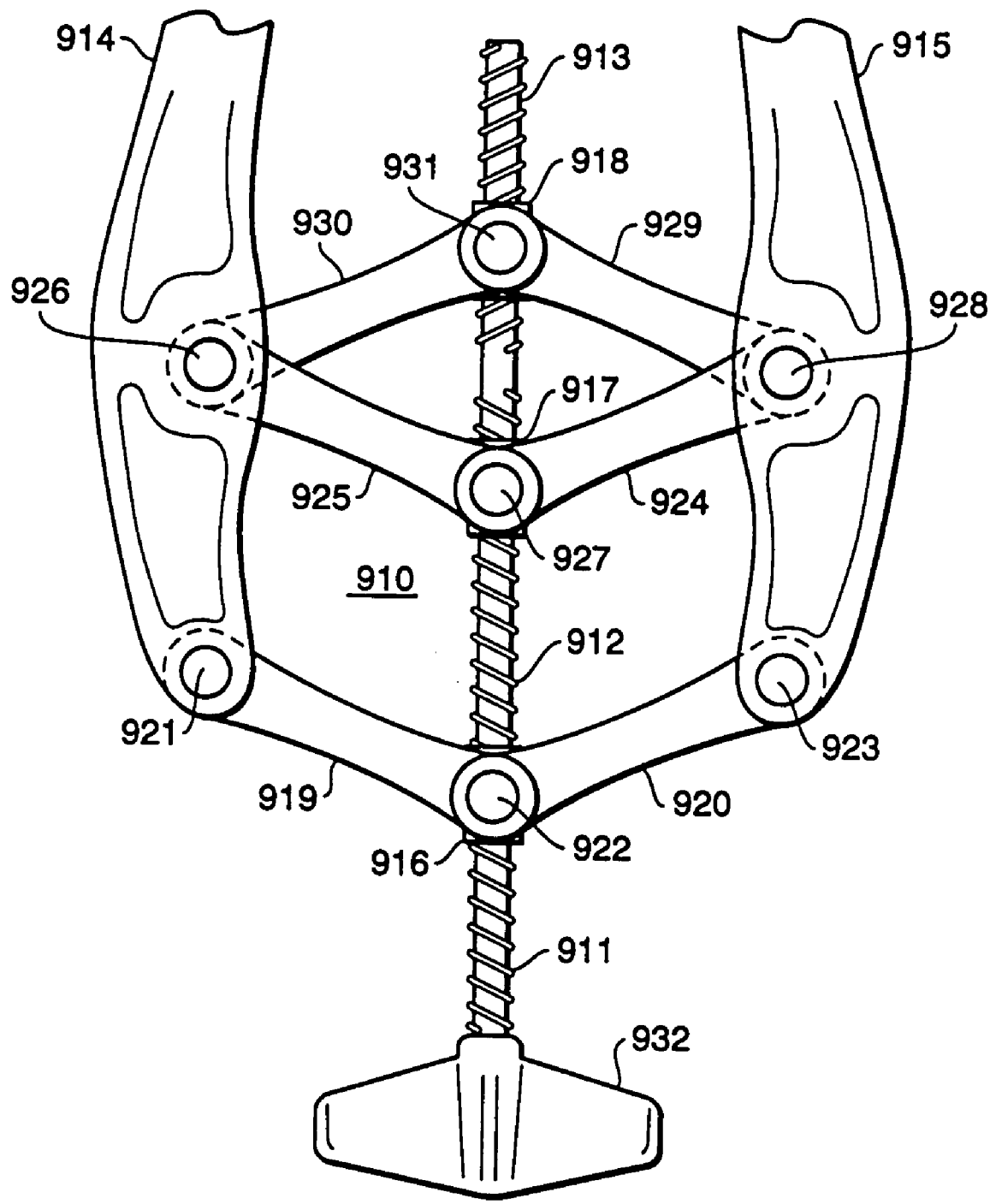
FIG. 63 is a top view of a spreader member drive assembly for an access platform.

Referring to FIG. 63, a drive mechanism 910 is coupled to blade arms 914 and 915. The drive mechanism 910 comprises a lead screw having first and second portions 912 and 913 having oppositely wound threads. A drive handle 932 is attached to one end of the lead screw 911. Drive blocks 917 and 916 are threadably carried on the first portion 912 of the lead screw 911. A drive block 918 is threadably carried on the second portion 913 of the lead screw 911. First and second links 929 and 930 are pivotally connected to the drive block 918 and the blade arms 914 and 915, respectively. Third and fourth links 925 and 924 are pivotally connected to the drive block 917 and the blade arms 914 and 915, respectively, at common pivots 926 and 928. Fifth and sixth links 919 and 920 are pivotally connected to the drive block 916 and blade arms 914 and 915, respectively.

In operation, the lead screw 911 is rotated in a first direction to transversely drive the drive blocks 917 and 916 and the drive block 918 in a direction away from each other, thereby drawing the blade arms 915 and 914 together. As the lead screw 911 is rotated in a second direction, the drive blocks 916 and 917 and the drive block 918 are transversely driven in a direction toward each other, thereby separating the blade arms 914 and 915. The links 919 and 920 operate to keep the blade arms 914 and 915 parallel.

Figure 64:
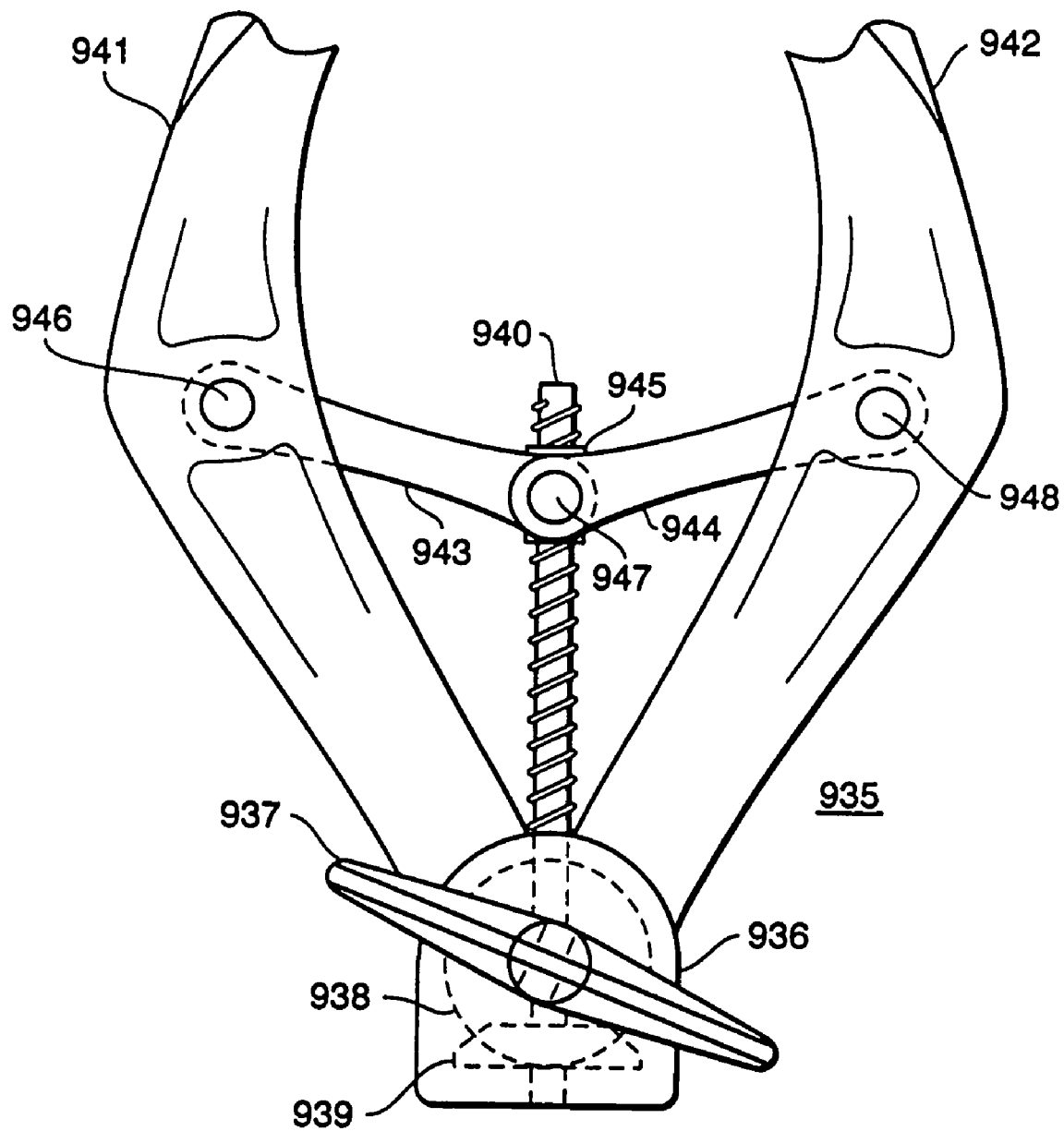
FIG. 64 is a top view of a spreader member drive assembly for an access platform.

Referring to FIG. 64, a drive mechanism 935 is coupled to pivotally connected blade arms 941 and 942. The drive mechanism 935 comprises a gear box 936 having a first bevel gear 939 attached to a lead screw 940 and operably coupled to a second bevel gear 938 attached to a handle 937. First and second links 943 and 944 are pivotally connected to the blade arms 941 and 942, respectively, and to a drive block 945 threadably carried on the lead screw 940. The drive handle 937 may alternatively be mounted more simply on the end of the lead screw 940.

In operation, the handle 937 is rotated to traversely drive the drive block 945 along the lead screw 940 to draw in or push out the blade arms 941 and 942.

Figure 65:
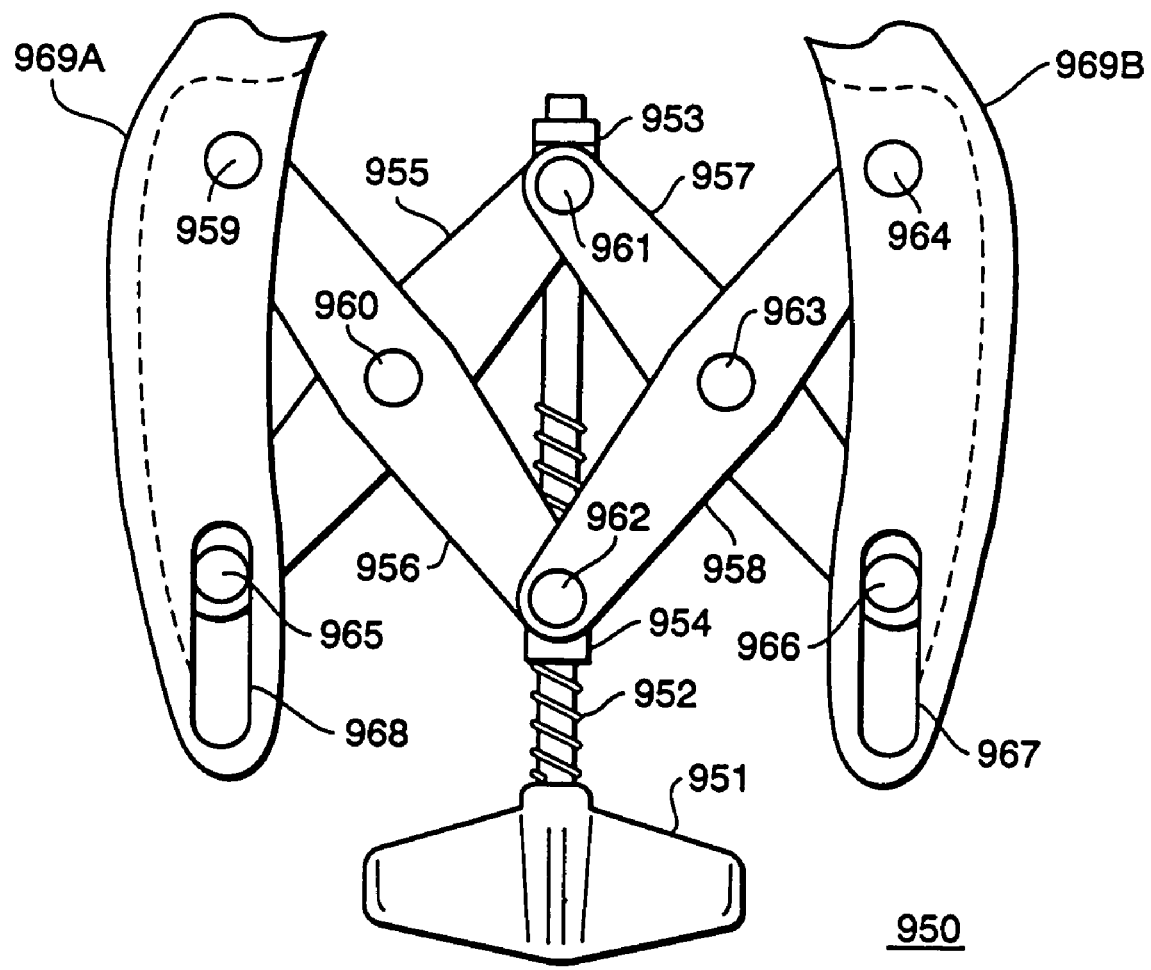
FIG. 65 is a top view of a spreader member drive assembly for an access platform.
Figure 68:
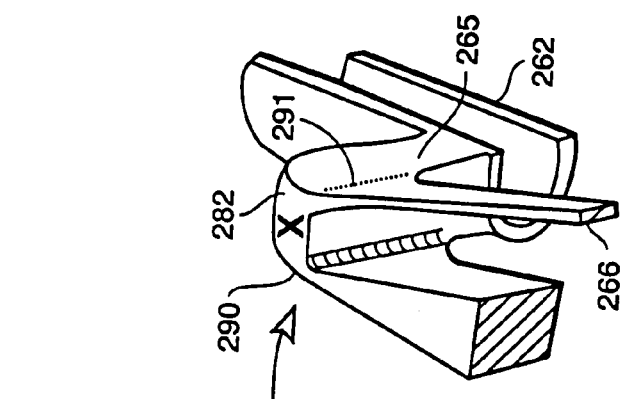
FIG. 68 is a partial isometric view of a blade and blade arm assembly of the access platform in FIG. 66.
Figure 67:
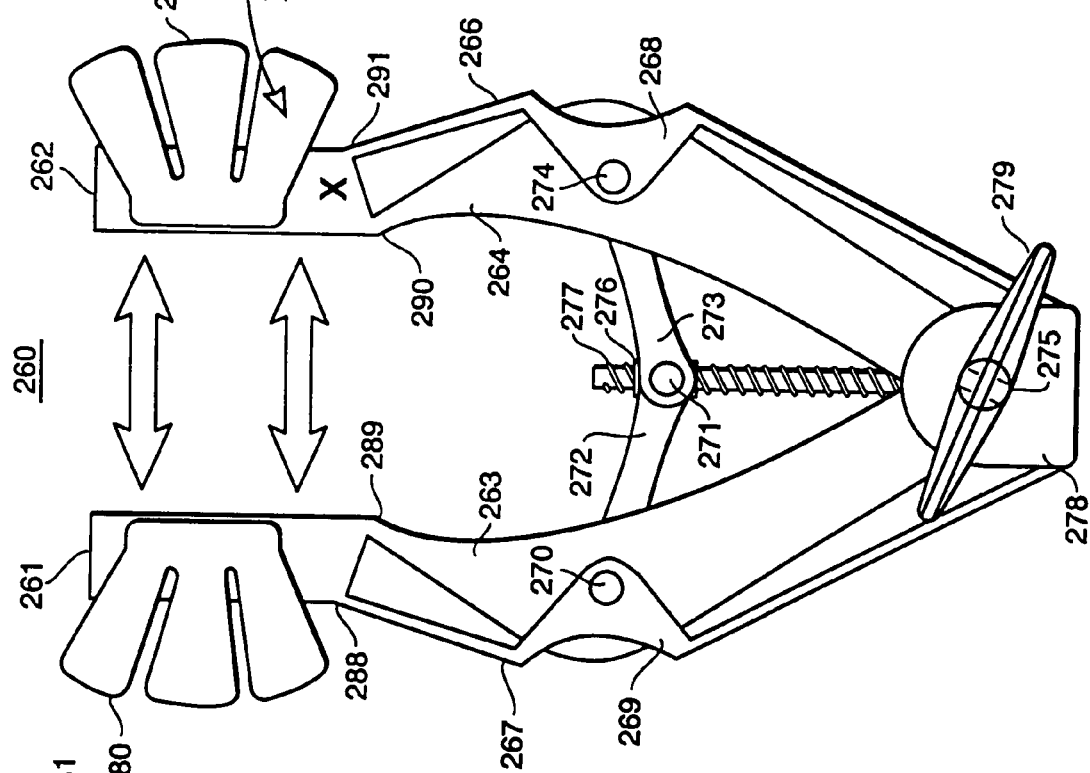
FIG. 67 is a top view of the access platform in FIG. 66 in an engaged position.
Figure 66:
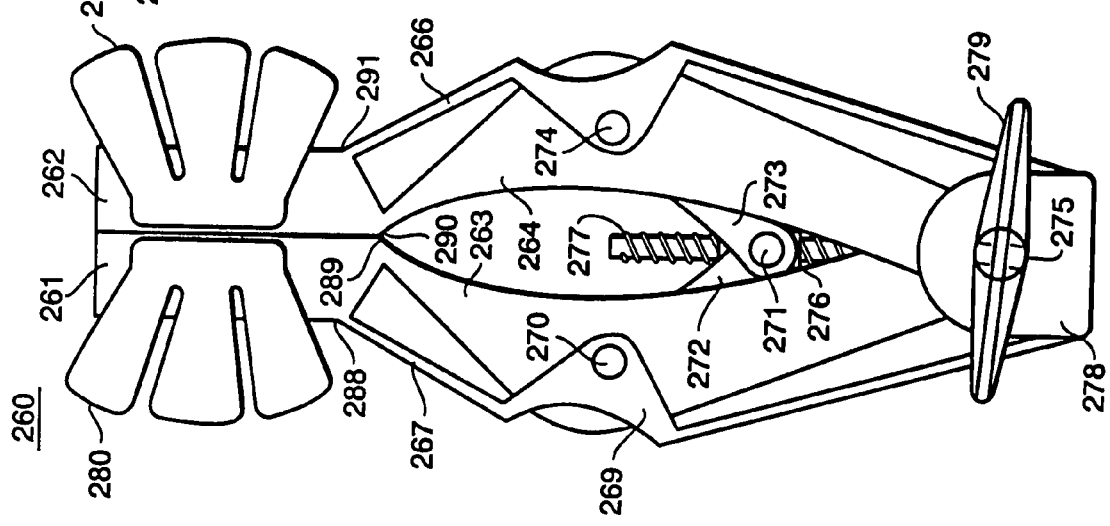
FIG. 66 is a top view of a self-aligning blade embodiment of the access platform of the present invention in a disengaged position.
Figure 69:
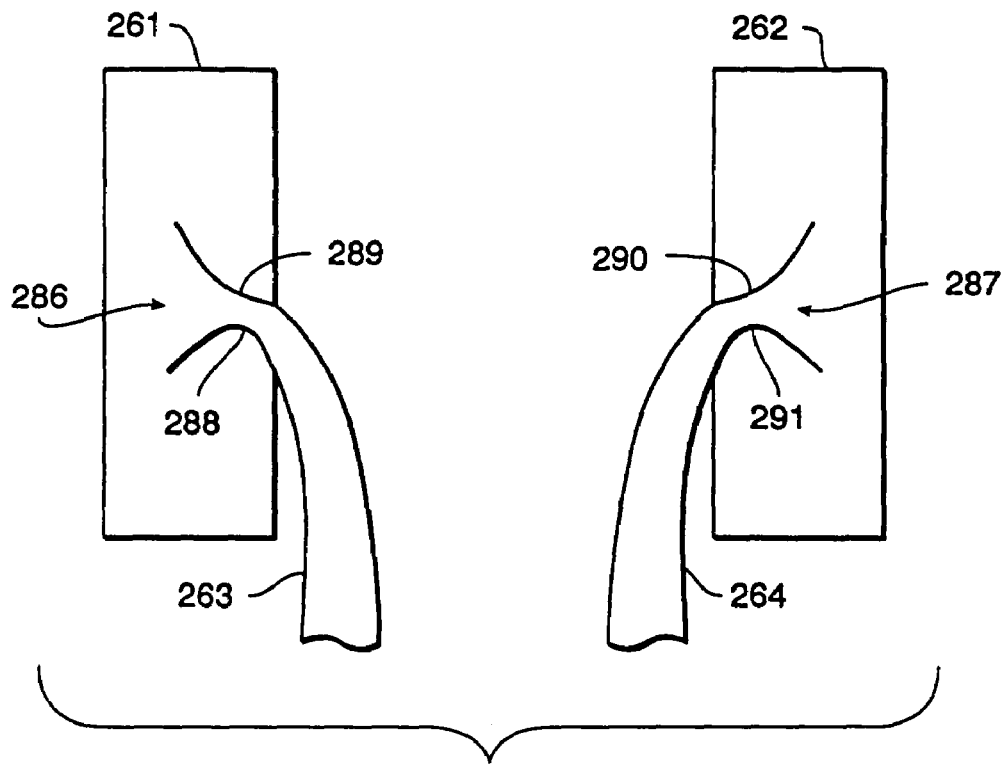
FIG. 69 is a top view of opposing self-aligning blade and blade arm assemblies.
Figure 70:
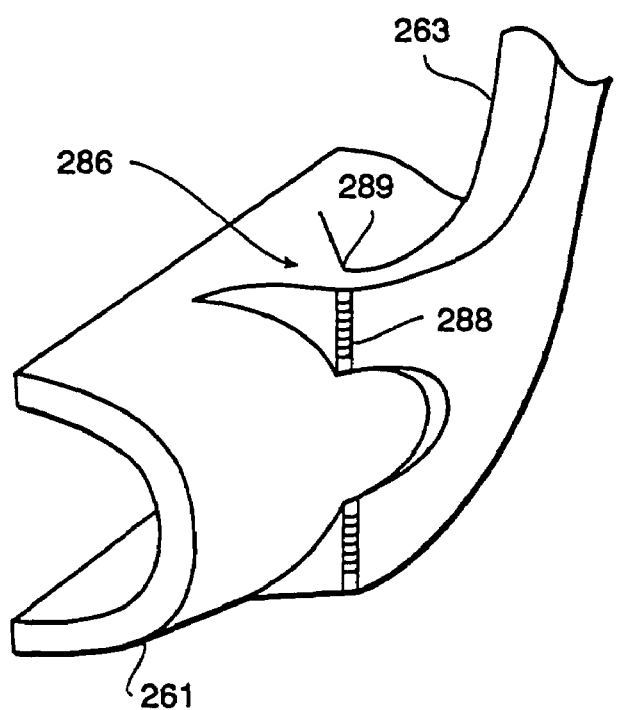
FIG. 70 is a partial isometric view of one of the self-aligning blade and blade arm assemblies in FIG. 69.

Referring to FIG. 65, a double scissor drive linkage 950 is coupled to parallelly disposed blade arms 969A and 969B. The drive mechanism 950 comprises a lead screw 952 having a rotatably captured carrier 953 on one end and a handle 951 attached to the other end. First and second links 956 and 958 are pivotally connected to the blade arms 969A and 969B, respectively, and to a drive block 954 threadably carried on the lead screw 952. Third and fourth links 955 and 957 are pivotally connected at their first ends to the carrier 953 and slidably and pivotally connected at their second ends to the blade arms 969A and 969B. Pivot followers 965 and 966, attached to the third and fourth links 955 and 957, are slidably and pivotally captured in guide slots 967 and 968 formed in the blade arms 969A and 969B. In addition, the first and second links 956 and 958 are pivotally coupled at pivots 960 and 963 to the third and fourth links 955 and 957.

In operation, the lead screw is rotated to either draw in or push out the blade arms 969A and 969B in a parallel fashion.

Referring to FIGS. 66-70, a self-aligning access platform 260 comprises blades 261 and 262 that are mounted to blade arms 263 and 264, respectively, and include tissue retractors 280 and 281 extending therefrom. The blade arms 263 and 264 are pivotally connected at a pivot 275 and driven apart or together by a drive mechanism 278. The drive mechanism 278 includes a handle 279 operably coupled to a lead screw 277. First and second links 272 and 273 are pivotally coupled to the blade arms 263 and 264, respectively, and a drive block 276 threadably carried on the lead screw 277.

The blade arms 263 and 264 comprise a branch (shown at 265 in FIG. 68) that extends upwardly from the blades 261 and 262 to an elbow (shown at 282 in FIG. 68) where the blade arms 263 and 264 bend and extend away from the blades 261 and 262. The blade arms 263 and 264 narrow down to a thin section at flexures 289 and 290 adjacent the blade arm elbows. Thin elongated tension members 266 and 267 extend between the drive member 278 and the blade arm elbows in a spaced relation with the blade arms 263 and 264. The tension members 266 and 267 include knuckles 268 and 269 coupled to the blade arms 263 and 264 at pivots 270 and 274. Thin flexures 288 and 291 are formed at the intersection between the tension members 266 and 267 and the blade arm elbows. As the drive member is operated to spread the ribs apart, the blades 261 and 262 will advantageously flex about flexures 288 and 289 and 290 and 291, respectively, to compensate for the alignment of the blade arms 263 and 264 relative to the retracted ribs.

Alternatively, blades 261 and 262 are coupled to the blade arms 263 and 264 which have V-shaped mounts 286 and 287 with opposing flexures 288 and 289, 290 and 291, respectively. As the ribs are separated, the blades 261 and 262 will flex at flexures 288, 289, 290 and 291 and, thus, advantageously apply a force at the center of effort through the flexures 288, 289, 290 and 291.

Figure 71:
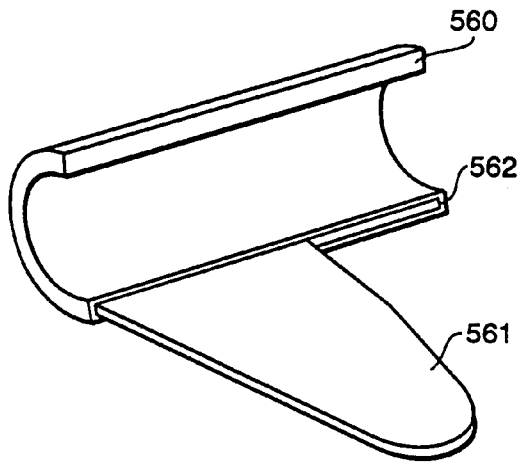
FIG. 71 is an isometric view of a spreader blade with a foldable vane for offset.
Figure 72:
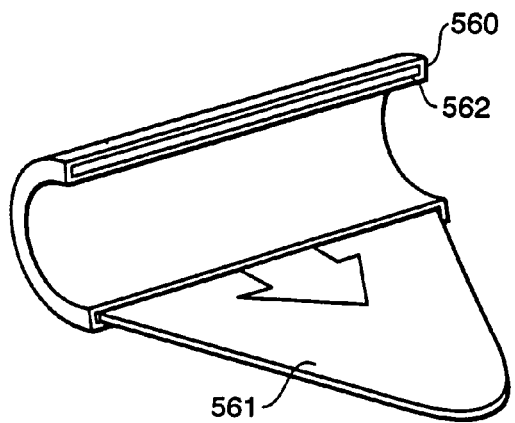
FIG. 72 is an isometric view of a spreader blade with a extensible vane for offset or tissue retraction.

Referring to FIGS. 71-74, the blades utilized with the access platform embodiments described herein are preferably interchangeable from a spreader-type blade to an offsetting-type blade. In FIG. 71, an elongated vane member 561 folds like a pocket knife into a slot 562 formed in a spreader blade 560. In FIG. 72, an elongated member 561 is extensible and flexible. The elongated member 561 can be hidden substantially within a slot 562 formed in a spreader blade 560, or extended out the top or bottom of the slot 562 for rib lifting or tissue retraction. The elongated member 561 is flexible in concavity but is prevented by straps or hinges from flexing in the opposite direction past straight.

Figure 73:
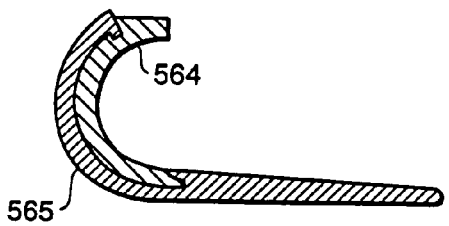
FIG. 73 is an elevation view of a spreader blade and detachable offset blade assembly.
Figure 74:
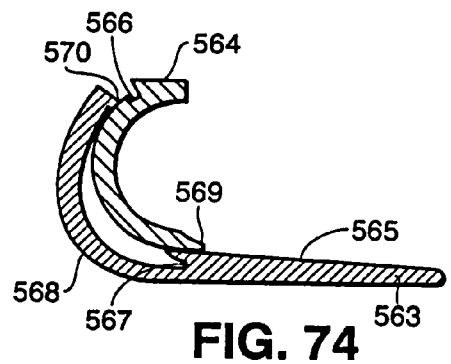
FIG. 74 is an elevation view of the spreader blade and vane assembly in FIG. 73 in a disengaged position.

In FIGS. 73 and 74, an offset type blade 565 is shown to comprise an elongated vane 563 and a recess in the throat area 568 sized to receive a spreader blade 564. A groove 567 is cut into the offset blade 565 at one end of the recess and a tongue 570 extending from the offset type blade 565 is formed at the other end of the recess. A tongue 569 extending from the lower portion of the spreader blade 564 mates with the groove 567 in the offset blade 565. A groove 566 formed in the top part of the spreader blade 564 mates with the tongue 570 of the offset-type blade 565. This tongue and groove assembly detachably couples the spreader and offset-type blades together to interchange a spreader blade 564 into an offset-type blade 565.

Figure 75:
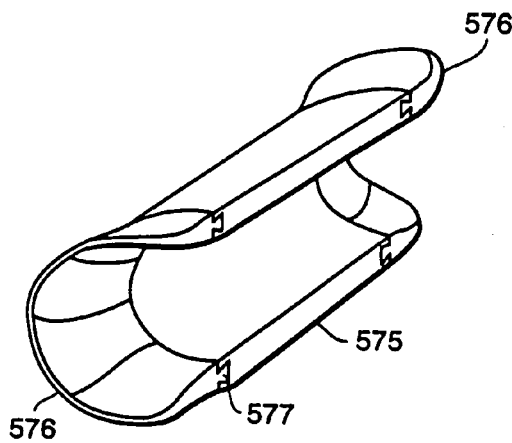
FIG. 75 is an isometric view of a retractor blade with detachable flexible edges.
Figure 76:
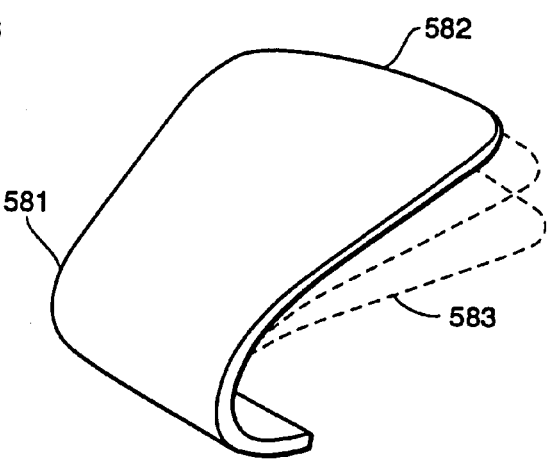
FIG. 76 is an isometric view of a retractor blade with an integral tissue retractor.

Referring to FIG. 75, a spreader blade 575 comprises force-tapering (reducing) flexible edges 576 extending outwardly from either end. The flexible edges 576 are coupled to the spreader blade 575 via a dove-tail assembly 577. In FIG. 76, a spreader blade 581 is formed integrally with a tissue retractor 582 to advantageously allow for automatic tissue retraction. The un-engaged position of the tissue retractor 582 is shown in phantom at 583. Once engaged, the tissue forces the tissue retractor 582 upwardly.

Figure 78:
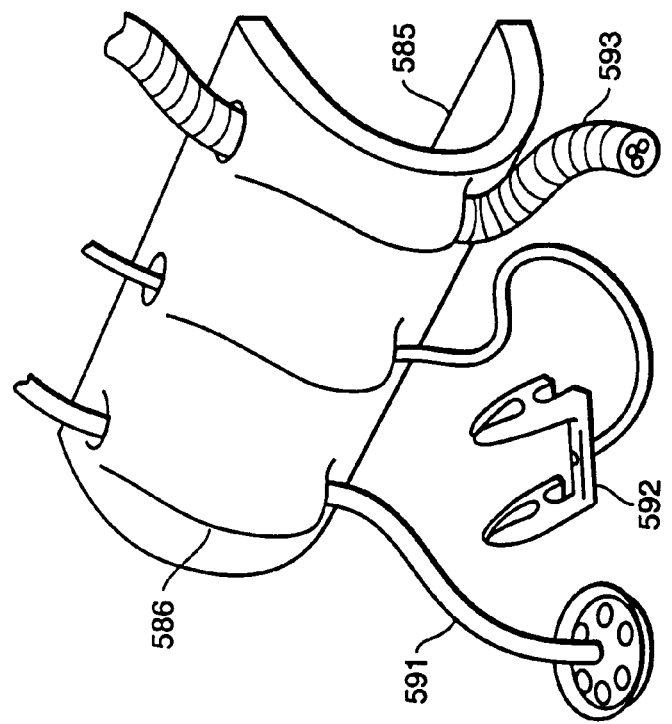
FIG. 78 is an isometric view of a spreader blade with surgical tools mounted through access mounts formed integrally with the spreader blade.
Figure 79:
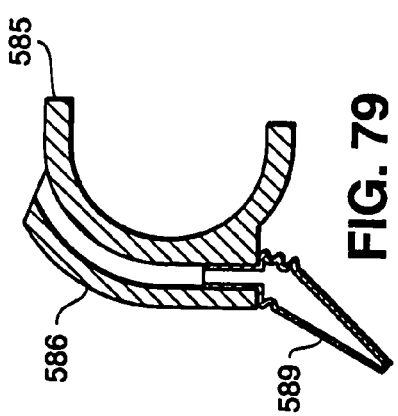
FIG. 79 is a cross-sectional view of the spreader blade and flexible blower assembly in FIG. 77.
Figure 77:
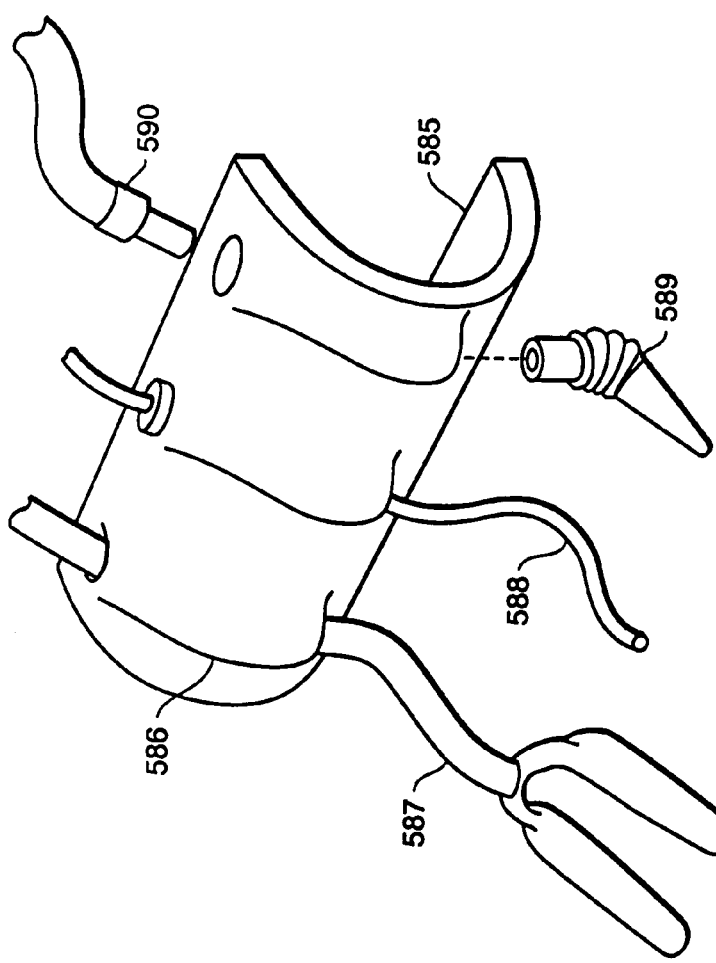
FIG. 77 is an isometric view of a spreader blade with surgical tools mounted through access mounts formed integrally with the spreader blade.

Referring to FIGS. 77-79, a blade 585 comprises a plurality of access mounts 586 formed integrally in the back side of the blade 585. A number of different surgical tools such as a stabilizer 587, malleable shaft blower 588, a flexible blower 589 and hose 590, a suction boot 591, a clip 592, or a light source 593 can be retained in the access mounts 586 of the blade 585 to facilitate use of these instruments during a surgical procedure in a minimally sized access area in the patient's chest. In addition, retaining the surgical instruments in these access mounts 586 advantageously eliminates the need for additional sets of hands in the surgeon's working space.

Figure 80:
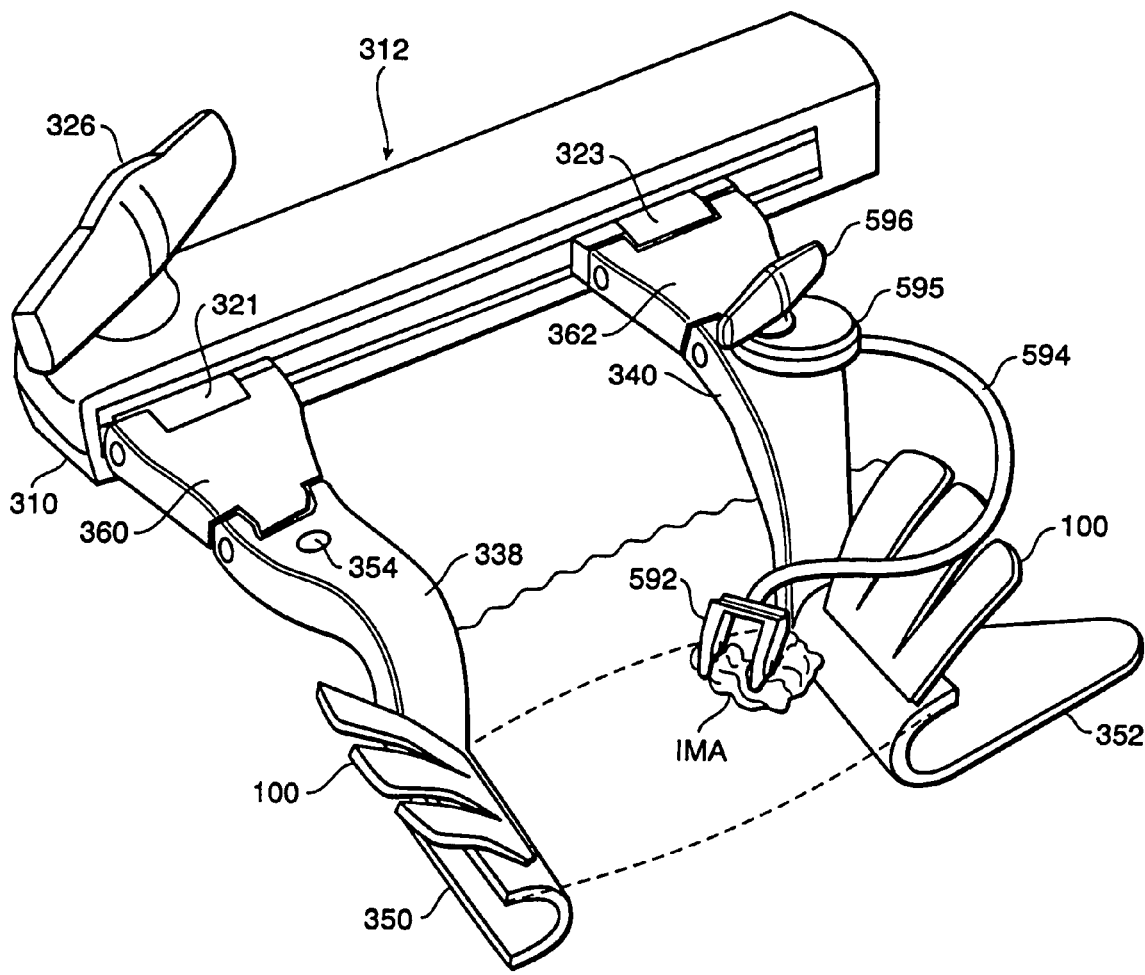
FIG. 80 is an isometric view of the access platform in FIG. 23 less the offsetting assembly and having a surgical clip mounted thereto.
Figure 81:
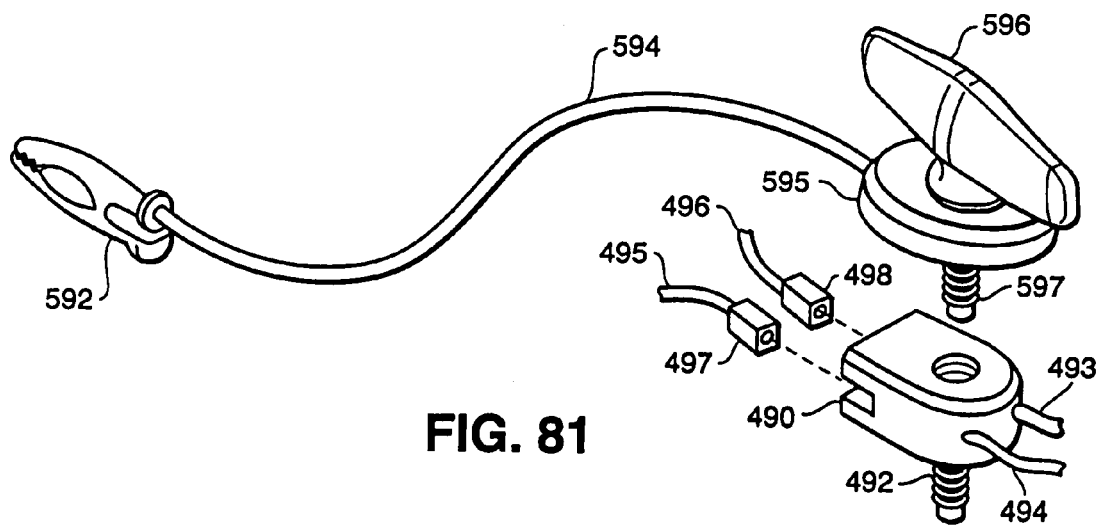
FIG. 81 is an isometric exploded view of a surgical clip, mount and intermediate mounting block assembly.

Similarly, in FIG. 80, a double clip 592 is attached to a stem 594 which is coupled via a mount 595 with a lever 596 to a blade arm 340 of an access platform 310 described in regard to FIG. 23. The double clip 592 is positioned within the working space to hold the IMA and eliminate the need for another set of hands in the working space. Alternatively, as shown in FIG. 81, a shaft 597 of the mount 595 can be screwed into the intermediate mounting block 490. A stem 594 extends from the mount 595 to a single clip 592. The shaft 492 of the intermediate mounting block 490 is in turn screwed into a port such as the port 354 in the blade arm 338 of the access platform 310 in FIG. 80. The intermediate mounting block 490 advantageously includes input ports 493 and 494 for suction, aeration, electrical power, etc. Output lumens 495 and 496 with plugs 497 and 498 are coupled to the mounting block 490 to access the electrical power, suction or aeration, etc. for an attached surgical tool.

Figure 82:
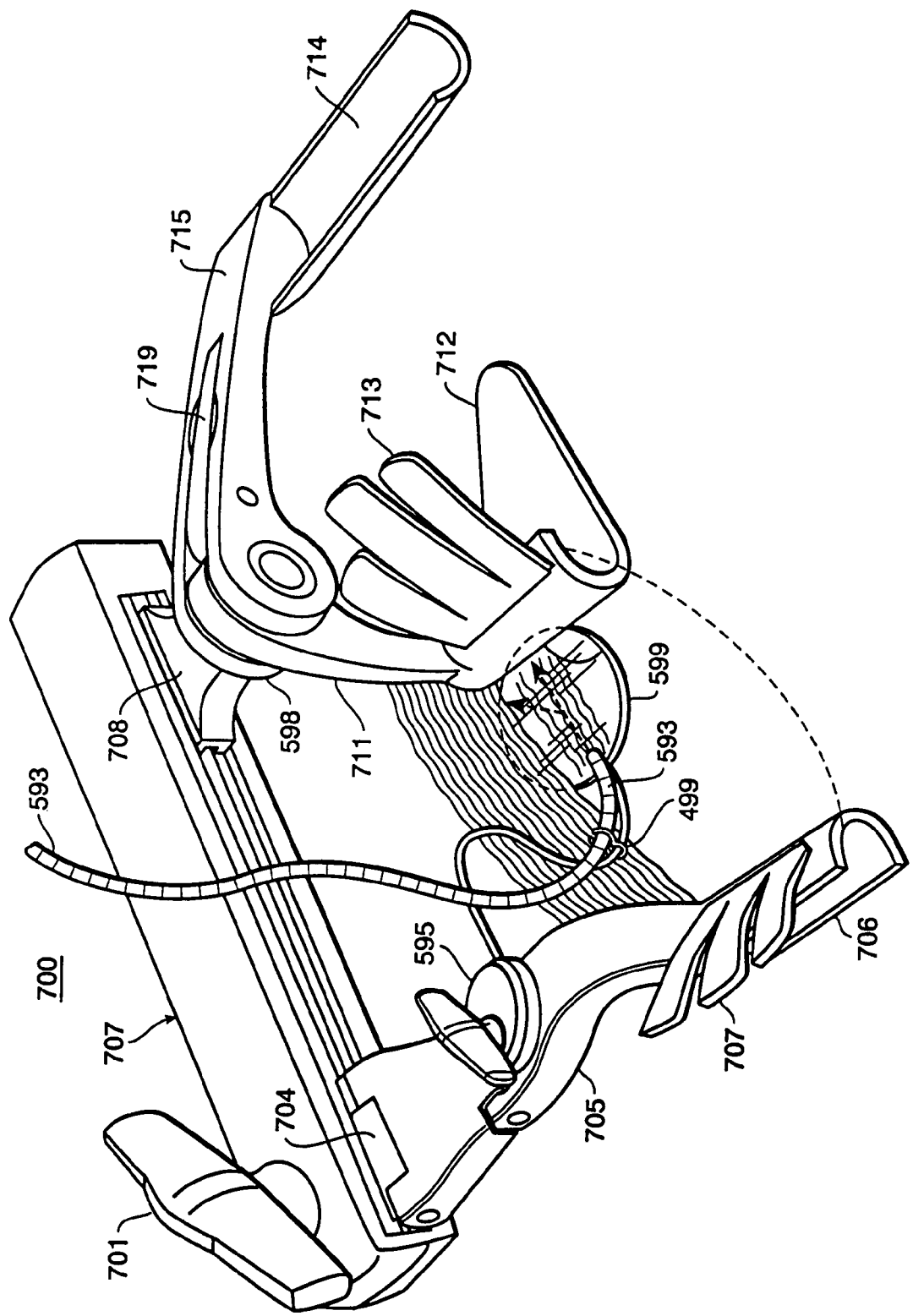
FIG. 82 is an isometric view of the access platform in FIG. 35 having a mirror, a light source and clip assembly mounted thereto.

In FIG. 82, a mirror 599 extends on a malleable shaft 598 from a mount 596 that is coupled to a blade arm 705 of an access platform 700 previously described herein with regard to FIG. 33. In addition, a light source 593 is coupled to the malleable shaft 598 by a clip 499 to direct light toward the mirror 599 to further illuminate the working space within the patient's chest. The light 593 is advantageously positioned out of the critical cone of operation.

Figure 83:
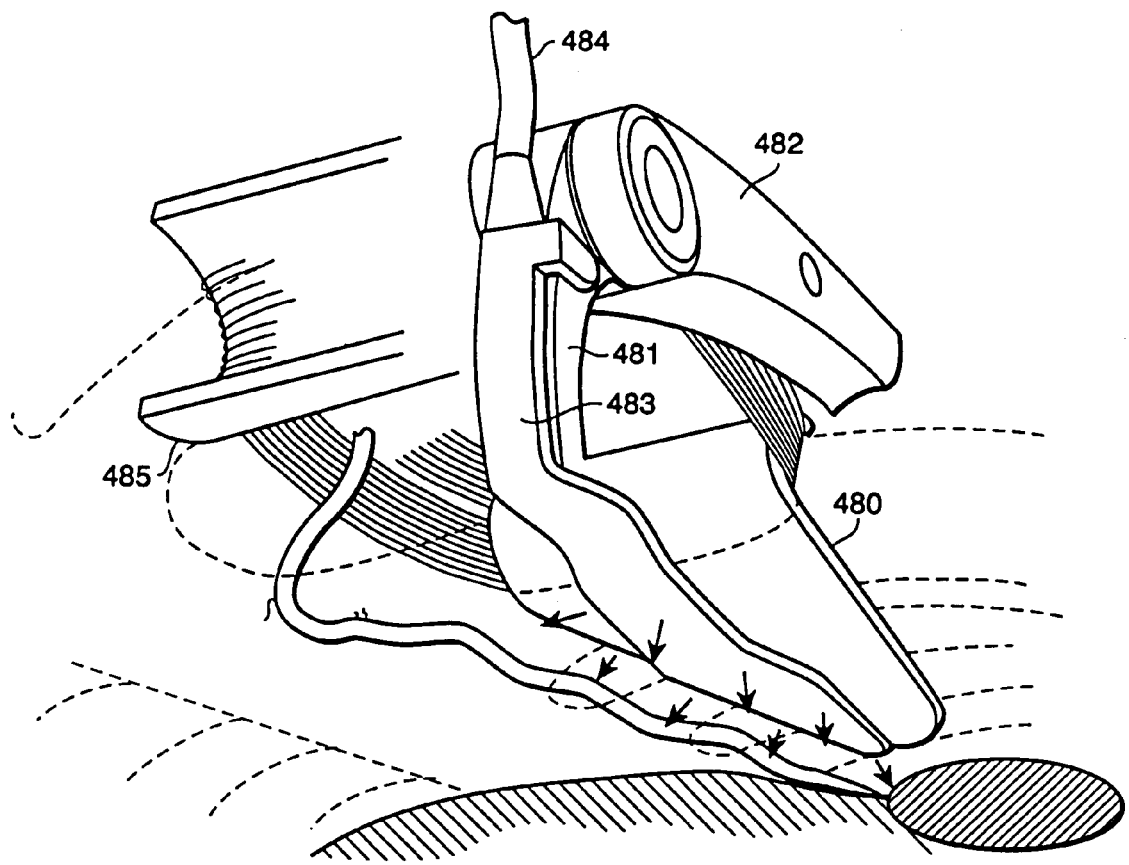
FIG. 83 is a partial isometric view of an access platform in an engaged position with the superior blade having a light panel mounted thereto.
Figure 84:
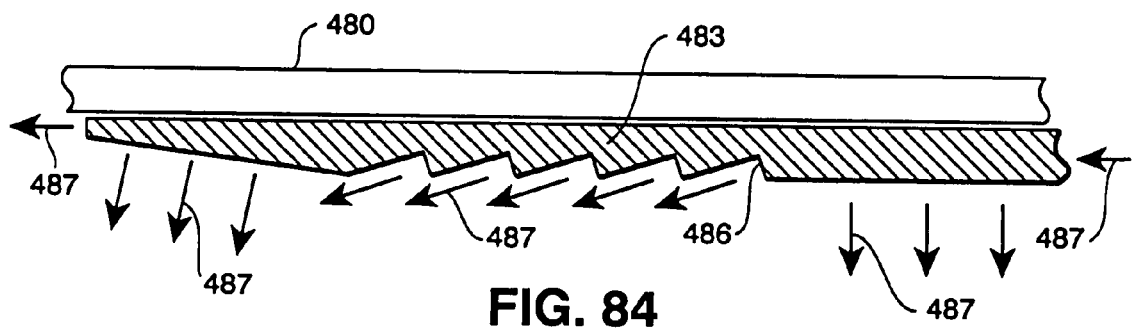
FIG. 84 is a partial elevation view of a directional light source mounted to the bottom of a superior blade.

Referring to FIG. 83, a light source 484 is coupled to a light panel 483 that is mounted on a superior blade 480 and a blade arm 481 which is pivotally coupled to a sternal pad arm 482. The light panel 483 is used to illuminate the working space created by the superior blade 480 and inferior blade 485. The light panel 483 may preferably include a contoured surface 486 to direct the light as noted by directional arrows 487 (see FIG. 84).

Figure 85:
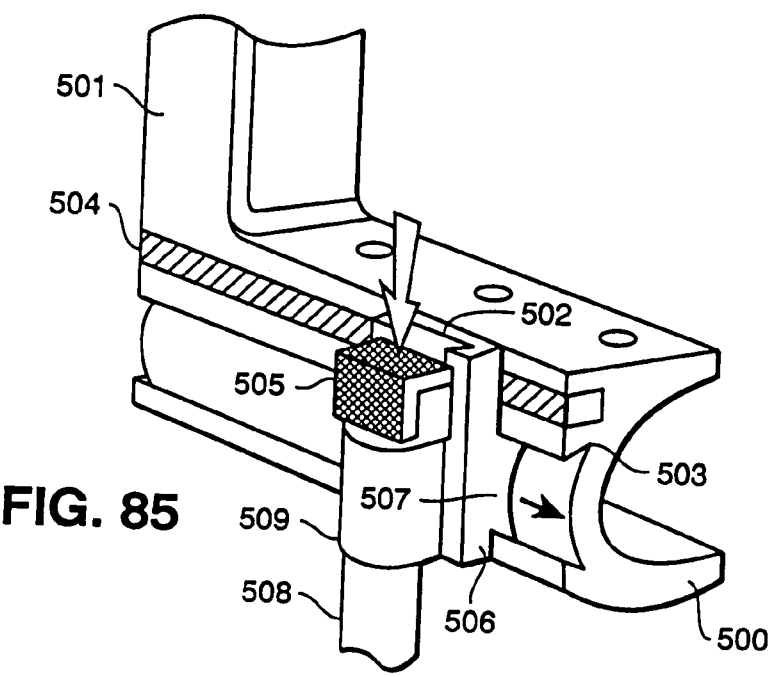
FIG. 85 is an isometric view of a spreader blade assembly.

Turning to FIG. 85, a blade 500 includes a horizontal dove-tail slot 503 extending the length of the back side of the blade 500. A slide 506 includes a tail 507 slidably received in the slot 503. A connector 509 of a surgical tool is detachably received in a vertical dove-tail slot 502 cut into the slide 506. The connector 509 includes a push button 505 that acts to lock the slide 506 in place along the horizontal bevel slot 503 and electrically couple the connector to the embedded electrical source 504 that extends along the back side of the blade 500.

Figure 86:
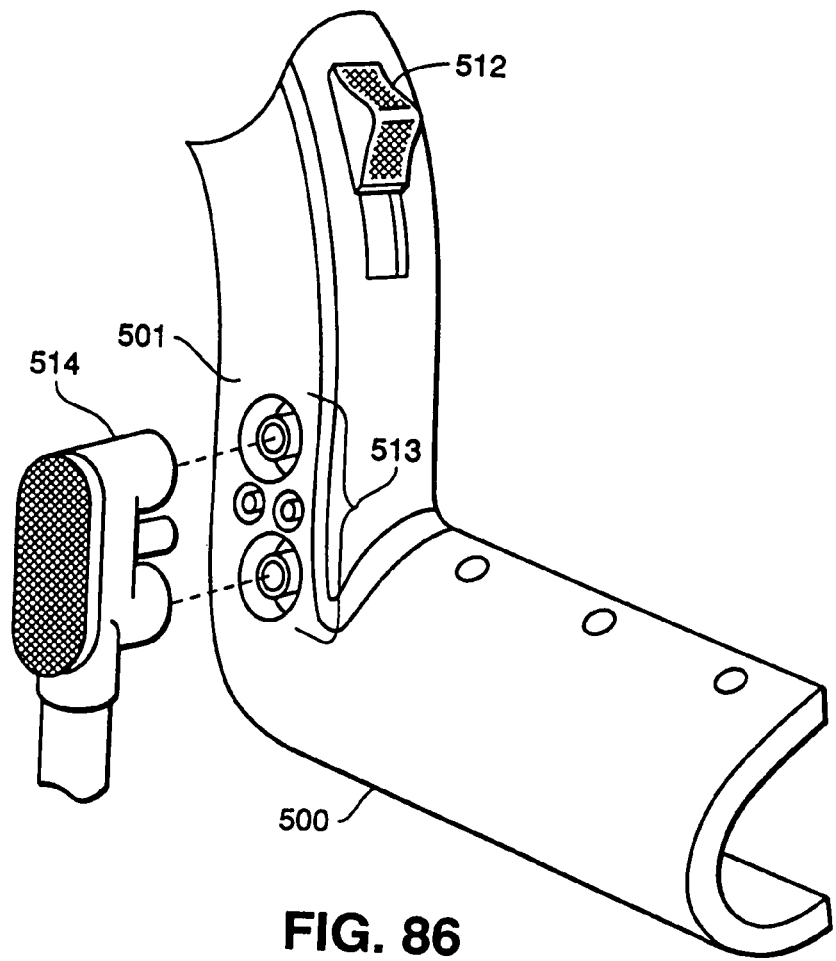
FIG. 86 is an isometric view of a spreader blade assembly.

In FIG. 86, a blade arm 501 connected to a blade 500 includes a universal port 513 which provides access to sources of electrical power, aeration, suction, etc. A universal plug 514 on the end of a surgical tool couples to the universal port 513. An on/off lock-in switch 512 is provided on the blade arm 501 to either open or close access to the sources of electrical power, suction, aeration, etc. and/or lock the universal plug 514 in the universal port 513.

Figure 87:
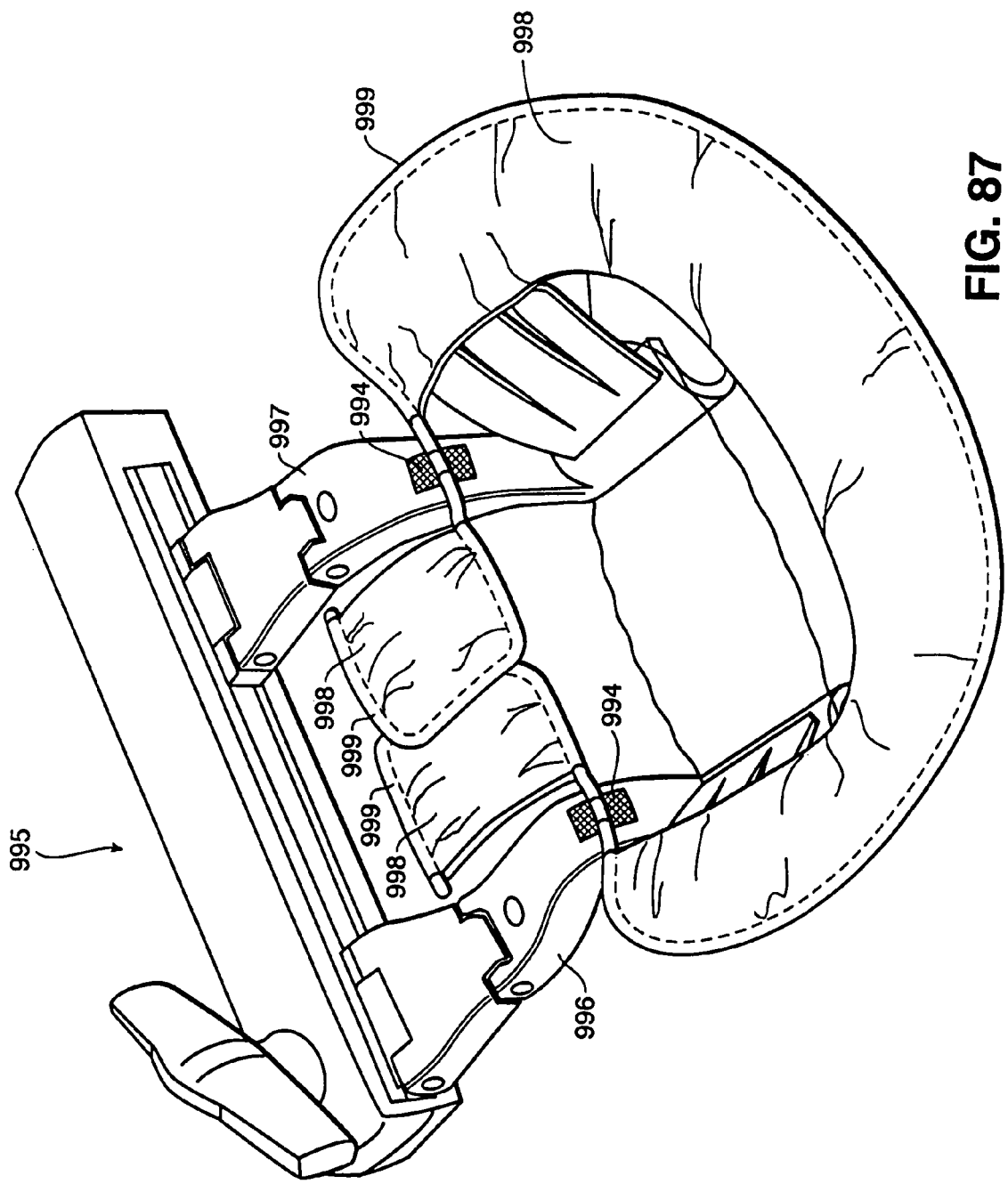
FIG. 87 is an isometric view of an access platform and suture holder assembly.

Referring to FIG. 87, an access platform 995 includes a suture holder 998 connected to the blade arms 996 and 997. The suture holder 998 is preferably made from felt, foam, or rubber, or any other material that will substantially not shed particulates. The suture holder 998 includes an internal stiffener 999 to drape the suture holder 998 about the access area in the patient's chest. The suture holder 998 facilitate suturing during a surgical procedure.

The embodiments of the access platform and accessories described herein are preferably first bulk sterilized and packaged in a container completely enclosing the access platform and its accessories, wherein the container prevents microorganisms from reaching the access platform. Alternatively, the access platform and accessories would be sterilized after enclosing the access platform in the container. Methods of sterilization could include gamma radiation.

When packaged in this manner, the surgeon can withdraw the access platform ready-for-use in the surgical procedure and operate the access platform in a manner described herein.

While the above description contains many specificities, these should not be construed as limitations on the scope of the invention, but rather as an exemplification of one preferred embodiment thereof. Other variations are possible.

Accordingly, the scope of the present invention should be determined not by the embodiments illustrated above, but by the appended claims and their legal equivalents.

What is claimed is:

1. A device for use in a surgical procedure in which an incision is made between two juxtaposed ribs of a patient, the device comprising:
a first arm member having a proximal end portion and a distal end portion, the distal end portion having a rib engaging blade;
a second arm member having a proximal end portion and a distal end portion, the distal end portion having a rib engaging blade;
a mechanism interposed between the first and the second arm members and arranged to mechanically drive the arm members toward and away from each other, wherein operation of the mechanism to drive said arm members away from each other in a first direction relative to one another, when said rib engaging blades are each respectively engaged with a rib on opposite sides of the incision, also drives movement of one of said arm members and one of said rib engaging blades in a second direction relative to the other of said arm members different from said first direction.

2. The device of claim 1 wherein the mechanism includes a rack bar fixedly attached to the first arm member at one end and at another end movably engages the proximal end portion of the second arm member such that the second arm member moves away and toward the first arm member along the rack bar.

3. The device of claim 1 wherein the distal end portion of the first arm member further includes a plurality of fingers extending away from the blade for retaining fatty tissue away from the incision.

4. The device of claim 1 wherein the arm member further having the rib engaging blade attached thereto that is moved in the second direction is rotatably mounted with respect to the mechanism and is rotatable during use.

5. A device for use in a surgical procedure for spreading an incision, said device comprising:
a base portion,
a first arm member fixedly attached to said base portion and having a distal end portion extending away from said base portion, said distal end portion having a first rib engaging blade;
a second arm member movably mounted with respect to said base portion, said second arm member having a second rib engaging blade; and
a driving mechanism mechanically interconnecting between said first and second arm members and operably providing a driving action to drive said second arm member away from said first arm member in a first relative direction between said first and second arm members, and, with the same driving action, to drive said second rib engaging blade and said second arm in a second relative direction between said first and second arm members, different from said first direction when said first and second rib engaging blades are engaged with ribs on opposite sides of the incision.

6. The device of claim 5, further comprising a support arm rotatably mounted with respect to said base portion, said support arm adapted to rest against the surface of a body of a patient during driving by said mechanism.

7. The device of claim 6, wherein said support arm is fixed with respect to said second arm in one direction of rotation and rotates with said second arm with respect to said base portion during driving by said mechanism.

8. The device of claim 6, wherein said support arm ratchets with respect to said second arm.

9. The device of claim 6, wherein said support arm comprises a sternal pad at a distal end thereof.

10. A retractor for opening the chest during surgery, said retractor comprising:
first and second substantially opposed retractor blades adapted to engage opposite incision edges of a chest incision;
first and second arms connecting said first and second retractor blades to a frame structure; and
adjusting means associated with the frame and interconnected between said first and second arms for adjusting the relative distance in a first direction between the first and second arms, wherein said adjusting at the same time drives one of the first and second retractor blades in a second direction different from said first direction to alter a relative height between said first and second retractor blades.

11. The retractor of claim 10, wherein said second arm is rotatably and translationally movable with respect to said frame, and wherein driving of said second arm by said adjusting means to increase the relative distance between the first and second arms also rotates the second arm with respect to said frame, thereby lifting said second retractor blade relative to said first retractor blade.

12. The retractor of claim 11, wherein said second retractor blade is attached to said second arm and rotates with said second arm during said lifting.

13. The retractor of claim 11, further comprising a support arm rotatably coupled to said second arm.

14. A device for use in a surgical procedure for spreading an incision, said device comprising:

a base portion, a first arm member fixedly attached to said base portion and having a distal end portion extending away from said base portion, said distal end portion having a first rib engaging blade;

a second arm member movably mounted with respect to said base portion, said second arm member having a second rib engaging blade;

a support arm rotatably coupled to said second arm; and a mechanism operable to drive said second arm member away from said first arm member and to drive said second rib engaging blade vertically with respect to said first rib engaging blade when said support arm contacts an external chest wall and first and second rib engaging blades are engaged with ribs on opposite sides of the incision, said support arm transferring lifting force to said second arm.

15. The device of claim 14, further comprising an offset positioning assembly that allows said support arm to rotate with respect to said second arm in one direction of rotation and prevents rotation of said support arm in an opposite direction of rotation.

16. The device of claim 15, wherein said offset positioning-assembly comprises a pawl mounted in one of said support arm and said second arm, and a ratchet mounted in the other of said support arm and said second arm.

17. A device for use in a surgical procedure for spreading an incision, said device comprising:

a base portion extending substantially horizontally;

a first blade arm fixedly attached to said base portion and extending outwardly and downwardly therefrom to a first distal end portion having a first rib engaging blade;

a second blade arm rotatably and translationally mounted with respect to said base portion and extending downwardly therefrom to a second distal end portion having a second rib engaging blade;

a support arm rotatably coupled to said second blade arm; and a mechanism operable to drive said second blade arm away from said first arm member in a translational direction relative to said first arm member and to drive said second blade arm rotationally relative to said first blade arm to drive said second rib engaging blade vertically with respect to said first rib engaging blade when said first and second rib engaging blades are engaged with ribs on opposite sides of the incision.

18. A retractor for opening the chest during surgery, said retractor comprising:

first and second substantially opposed retractor blades adapted to engage opposite incision edges of a chest incision;

first and second arms connecting said first and second retractor blades to a frame structure;

a support arm adjustably mounted to said first arm, said support arm being adjustable for contact with an external surface of a patient's body prior to spreading the incision edges;

first adjusting means associated with the frame structure; and second adjusting means arranged to allow adjustment of the support arm prior to said spreading;

wherein adjustment by said first adjusting means adjusts the relative distance between the first and second arms drives rotation of said first arm relative to said frame.

19. The retractor of claim 18, wherein said support arm comprises a pad arm having a sternal pad at a distal end thereof.

20. The retractor of claim 18, wherein said first arm is rotatably and translationally movable with respect to said frame, and wherein adjustment by said first adjustment means comprise driving of said first arm by said adjusting means to increase the relative distance between the first and second arms, thereby also rotating the first arm with respect to said frame, thereby lifting said first retractor blade relative to said second retractor blade.

21. A device for use in a surgical procedure for spreading an incision, said device comprising:

a base portion, a first arm member fixedly attached to said base portion and having a distal end portion extending away from said base portion, said distal end portion having a first rib engaging blade;

a second arm member movably and rotatably mounted with respect to said base portion, said second arm member having a second rib engaging blade;

a mechanism operable to drive said second arm member away from said first arm member and to drive said second rib engaging blade vertically with respect to said first rib engaging blade when said first and second rib engaging blades are engaged with ribs on opposite sides of the incision; and a support arm rotatably mounted with respect to said base portion, said support arm adapted to rest against the surface of a body of a patient during driving by said mechanism.

22. A retractor for opening the chest during surgery, said retractor comprising:

first and second substantially opposed retractor blades adapted to engage opposite incision edges of a chest incision;

first and second arms connecting said first and second retractor blades to a frame structure; and adjusting means associated with the frame for adjusting the relative distance between the first and second arms and for adjusting the relative height between the first and second retractor blades, wherein said second arm is rotatably and translationally movable with respect to said frame, and wherein driving of said second arm by said adjusting means to increase the relative distance between the first and second arms also rotates the second arm with respect to said frame, thereby lifting said second retractor blade relative to said first retractor blade and relative to said frame.

23. A device for use in a surgical procedure for spreading an incision, said device comprising:

a base portion, a first arm member fixedly attached to said base portion and having a distal end portion extending away from said base portion, said distal end portion having a first rib engaging blade;

a second arm member movably mounted with respect to said base portion, said second arm member having a second rib engaging blade;

a driving mechanism mechanically interconnecting between said first and second arm members and operably providing a driving action to drive said second arm member away from said first arm member and, with the same driving action, to drive said second rib engaging blade and said second arm vertically with respect to said base portion and with respect to said first rib engaging blade when said first and second rib engaging blades are engaged with ribs on opposite sides of the incision, wherein the vertical driving direction is different from the direction in which the second arm member is driven away from the first arm member; and a support arm rotatably mounted with respect to said base portion, said support arm adapted to rest against the surface of a body of a patient during driving by said mechanism, wherein said support arm comprises a sternal pad at a distal end thereof.

24. A device for use in a surgical procedure for spreading an incision, said device comprising:

a base portion, a first arm member fixedly attached to said base portion and having a distal end portion extending away from said base portion, said distal end portion having a first rib engaging blade;

a second arm member movably mounted with respect to said base portion, said second arm member having a second rib engaging blade;

a support arm rotatably coupled to said second arm;

a mechanism operable to drive said second arm member away from said first arm member and to drive said second rib engaging blade vertically with respect to said first rib engaging blade when said support arm contacts an external chest wall and said first and second rib engaging blades are engaged with ribs on opposite sides of the incision, said support arm transferring lifting force to said second arm; and an offset positioning assembly that allows said support arm to rotate with respect to said second arm in one direction of rotation and prevents rotation of said support arm in an opposite direction of rotation, wherein said offset positioning assembly comprises a pawl mounted in one of said support arm and said second arm, and a ratchet mounted in the other of said support arm and said second arm.

25. A retractor for opening the chest during surgery, said retractor comprising:

first and second substantially opposed retractor blades adapted to engage opposite incision edges of a chest incision;

first and second arms connecting said first and second retractor blades to a frame structure;

a support arm adjustably mounted to said first arm, said support arm being adjustable for contact with an external surface of a patient's body prior to spreading the incision edges, and wherein said support arm comprises a pad arm having a sternal pad at a distal end thereof;

first adjusting means associated with the frame structure; and second adjusting means arranged to allow adjustment of the support arm prior to said spreading;

wherein adjustment by said first adjusting means drives the relative distance between the first and second arms as well as the relative height between the first and second retractor blades.

26. The device of claim 14, wherein said support arm applies torque against the external chest wall to maintain lift by said second arm.

* * * * *